(12) United States Patent
Chu et al.

(10) Patent No.: US 7,166,745 B1
(45) Date of Patent: Jan. 23, 2007

(54) TRANSFECTION REAGENTS

(75) Inventors: Yongliang Chu, Rockville, MD (US); Malek Masoud, Gaithersburg, MD (US); Gulilat Gebeyehu, Potomac, MD (US)

(73) Assignee: Invitrogen Corporation, Carlsbad, CA (US)

( * ) Notice: Subject to any disclaimer, the term of this patent is extended or adjusted under 35 U.S.C. 154(b) by 0 days.

(21) Appl. No.: 09/438,365

(22) Filed: Nov. 12, 1999

Related U.S. Application Data

(60) Provisional application No. 60/108,117, filed on Nov. 12, 1998.

(51) Int. Cl.
| | | |
|---|---|---|
| C07C 233/00 | (2006.01) | |
| C07C 235/00 | (2006.01) | |
| C07C 237/00 | (2006.01) | |
| C07C 239/00 | (2006.01) | |
| C07C 277/00 | (2006.01) | |

(52) U.S. Cl. .................. 564/155; 564/158; 564/159; 564/236; 564/290; 564/292; 564/295; 564/346; 564/355; 564/372; 564/503; 564/504; 564/505; 564/507; 564/509; 564/511; 564/512; 546/186; 546/264

(58) Field of Classification Search ............... 435/458, 435/238; 424/450; 514/7, 2, 44; 530/358; 540/467; 544/357; 546/186, 264; 564/155, 564/159, 158, 236, 290, 292, 295, 346, 355, 564/372, 503, 504, 506, 507, 509, 511, 512
See application file for complete search history.

(56) References Cited

U.S. PATENT DOCUMENTS 2,654,785 A 10/1953 Miescher et al.

(Continued)

FOREIGN PATENT DOCUMENTS

AU 158967 2/1952

(Continued)

OTHER PUBLICATIONS

McCluskie, M. et al., abstract No. 91045k, "Direct gene transfer to the respiratory tract of mice with pure plasmid and lipid-formulated DNA," *Chem. Abst. 130*:151 (Feb. 1999).

(Continued)

Primary Examiner—Brian Davis

(57) ABSTRACT

Disclosed are compounds capable of facilitating transport of biologically active agents or substances into cells having the general structure:

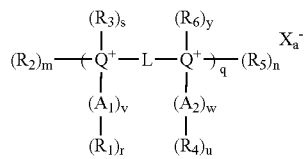

wherein

Q is selected from the group consisting of N, O and S; L is any bivalent organic radical capable of linking each Q, such as C, CH, $(CH_2)_1$, or $\{(CH_2)_i-Y-(CH_2)_j\}_k$, wherein Y is selected from the group consisting of $CH_2$, an ether, a polyether, an amide, a polyamide, an ester, a sulfide, a urea, a thiourea, a guanidyl, a carbamoyl, a carbonate, a phosphate, a sulfate, a sulfoxide, an imine, a carbonyl, and a secondary amino group and wherein Y is optionally substituted by $-X_1-L'-X_2-Z$ or $-Z$; $R_1-R_6$, independently of one another, are selected from the group consisting of H, $-CH_2)_p-D-Z$, an alkyl, an alkenyl, an aryl, and an alkyl or alkyl ether optionally substituted by one or more of an alcohol, an aminoalcohol, an amine, an amide, an ether, a polyether, a polyamide, an ester, a mercaptan, an alkylthio, a urea, a thiourea, a guanidyl, or a carbamoyl group, and wherein at least one of $R_1$, $R_3$, $R_4$ and $R_6$ is a straight chain or branched, cyclic, alkyl, alkenyl, alkynyl or aryl group; and any one of $R_1$, $R_3$, $R_4$ and/or $R_6$ may optionally be covalently linked with each other, with Y or with L when L is C or CH to form a cyclic moiety; Z is selected from the group consisting of amine, spermiyl, carboxyspermiyl, guanidyl, spermidinyl, putricinyl, diaminoalkyl, pyridyl, piperidinyl, pyrrolidinyl, polyamine, amino acid, peptide, and protein; $X_1$ and $X_2$, independently of one another, are selected from the group consisting of NH, O, S, alkylene, and arylene; L' is selected from the group consisting of alkylene, alkenylene, alkynylene, arylene, alkylene ether, and polyether; D is Q or a bond; $A_1$ and $A_2$, independently of one another, are selected from the group consisting of $CH_2O$, $CH_2S$, $CH_2NH$, $C(O)$, $C(NH)$, $C(S)$ and $(CH_2)_t$; X is a physiologically acceptable anion; m, n, r, s, u, v, w and y are 0 or 1, with the proviso that when both m and n are 0 at least one of r, s, u and y is other than 0; i, j, k, l, p and t are integers from 0 to about 100; q is an integer from 1 to about 1000; and a is the number of positive charge divided by the valence of the anion.

101 Claims, 4 Drawing Sheets

U.S. PATENT DOCUMENTS

| | | | |
|---|---|---|---|
| 2,695,314 A | 11/1954 | Kosmin | 260/584 |
| 2,867,665 A | 1/1959 | Dornfield | |
| 2,901,461 A | 8/1959 | Auerbach et al. | 260/47 |
| 3,152,188 A | 10/1964 | Kirkpatrick | 260/584 |
| 3,324,182 A | 6/1967 | De Brunner et al. | |
| 3,369,905 A | 2/1968 | Jones et al. | |
| 4,143,003 A | 3/1979 | Haas et al. | |
| 4,235,871 A | 11/1980 | Papahadjopoulos et al. | |
| 4,501,728 A | 2/1985 | Geho et al. | |
| 4,683,195 A | 7/1987 | Mullis et al. | |
| 4,683,202 A | 7/1987 | Mullis | |
| 4,737,323 A | 4/1988 | Martin et al. | |
| 4,767,699 A | 8/1988 | Vary et al. | |
| 4,800,159 A | 1/1989 | Mullis et al. | |
| 4,812,449 A | 3/1989 | Rideout | |
| 4,837,028 A | 6/1989 | Allen | |
| 4,889,818 A | 12/1989 | Gelfand et al. | |
| 4,889,953 A | 12/1989 | Inoue et al. | |
| 4,897,355 A | 1/1990 | Eppstein et al. | 435/240.2 |
| 4,946,787 A | 8/1990 | Eppstein et al. | |
| 4,962,022 A | 10/1990 | Fleming et al. | |
| 4,965,188 A | 10/1990 | Mullis et al. | |
| 4,967,008 A | 10/1990 | Friedli et al. | |
| 5,047,342 A | 9/1991 | Chatterjee | |
| 5,049,386 A | 9/1991 | Eppstein et al. | |
| 5,079,352 A | 1/1992 | Gelfand et al. | |
| 5,091,576 A | 2/1992 | Bergeron | |
| 5,165,925 A | 11/1992 | Leong | |
| 5,166,320 A | 11/1992 | Wu et al. | |
| 5,171,678 A | 12/1992 | Behr et al. | 435/172.3 |
| 5,186,923 A | 2/1993 | Piwnica-Worms et al. | |
| 5,187,085 A | 2/1993 | Lee | |
| 5,198,423 A | 3/1993 | Taguchi et al. | |
| 5,208,036 A | 5/1993 | Eppstein et al. | 424/450 |
| 5,244,797 A | 9/1993 | Kotewicz et al. | |
| 5,264,423 A | 11/1993 | Cohen et al. | |
| 5,264,618 A | 11/1993 | Felgner et al. | |
| 5,266,106 A | 11/1993 | Winnik et al. | |
| 5,270,179 A | 12/1993 | Chatterjee | |
| 5,276,019 A | 1/1994 | Cohen et al. | |
| 5,277,897 A | 1/1994 | Piwnica-Worms et al. | |
| 5,279,833 A | 1/1994 | Rose | 424/450 |
| 5,283,185 A | 2/1994 | Epand et al. | 435/172.3 |
| 5,286,717 A | 2/1994 | Cohen et al. | |
| 5,328,470 A | 7/1994 | Nabel et al. | |
| 5,328,984 A | 7/1994 | Pastan et al. | |
| 5,334,761 A | 8/1994 | Gebeyehu et al. | 564/197 |
| 5,338,532 A | 8/1994 | Tomalia et al. | |
| 5,350,672 A | 9/1994 | Oberst et al. | |
| 5,354,844 A | 10/1994 | Beug et al. | |
| 5,374,553 A | 12/1994 | Gelfand et al. | |
| 5,409,818 A | 4/1995 | Davey et al. | |
| 5,436,149 A | 7/1995 | Barnes | |
| 5,455,166 A | 10/1995 | Walker | |
| 5,455,335 A | 10/1995 | Kahne et al. | 536/5 |
| 5,459,127 A | 10/1995 | Felgner et al. | 514/7 |
| 5,484,702 A | 1/1996 | Ludwig | |
| 5,498,522 A | 3/1996 | Porter | |
| 5,498,523 A | 3/1996 | Tabor et al. | |
| 5,500,356 A | 3/1996 | Li et al. | |
| 5,506,212 A | 4/1996 | Hoke et al. | |
| 5,510,239 A | 4/1996 | Baracchini, Jr. et al. | |
| 5,510,476 A | 4/1996 | Ravikumar et al. | |
| 5,512,438 A | 4/1996 | Ecker | |
| 5,512,462 A | 4/1996 | Cheng | |
| 5,514,577 A | 5/1996 | Draper et al. | |
| 5,514,787 A | 5/1996 | Atkinson | |
| 5,519,134 A | 5/1996 | Acevedo et al. | |
| 5,521,291 A | 5/1996 | Curiel et al. | |
| 5,521,302 A | 5/1996 | Cook | |
| 5,527,524 A | 6/1996 | Tomalia et al. | |
| 5,527,928 A | 6/1996 | Nantz | |
| 5,532,142 A | 7/1996 | Johnston et al. | |
| 5,541,307 A | 7/1996 | Cook et al. | |
| 5,543,507 A | 8/1996 | Cook et al. | |
| 5,545,412 A | 8/1996 | Eppstein et al. | 424/450 |
| 5,545,540 A | 8/1996 | Mian | |
| 5,547,932 A | 8/1996 | Curiel et al. | |
| 5,550,289 A | 8/1996 | Eppstein et al. | 564/293 |
| 5,554,746 A | 9/1996 | Ravikumar et al. | |
| 5,560,929 A | 10/1996 | Hedstrand et al. | |
| 5,574,142 A | 11/1996 | Meyer, Jr. et al. | |
| 5,578,475 A | 11/1996 | Jessee | |
| 5,580,859 A | 12/1996 | Felgner et al. | |
| 5,583,198 A | 12/1996 | Whittaker | |
| 5,587,441 A | 12/1996 | Frechet et al. | |
| 5,587,446 A | 12/1996 | Frechet et al. | |
| 5,589,392 A | 12/1996 | Short | |
| 5,589,466 A | 12/1996 | Felgner et al. | 514/44 |
| 5,595,096 A | 1/1997 | Coffman | |
| 5,595,897 A | 1/1997 | Midoux et al. | |
| 5,596,091 A | 1/1997 | Switzer | |
| 5,602,240 A | 2/1997 | De Mesmaeker et al. | |
| 5,614,365 A | 3/1997 | Tabor et al. | |
| 5,627,159 A | 5/1997 | Shih et al. | |
| 5,631,329 A | 5/1997 | Yin et al. | |
| 5,635,487 A | 6/1997 | Wolff et al. | |
| 5,641,662 A | 6/1997 | Debs et al. | |
| 5,650,096 A | 7/1997 | Harris et al. | |
| 5,658,776 A | 8/1997 | Flotte et al. | |
| 5,661,025 A | 8/1997 | Szoka, Jr. et al. | |
| 5,667,774 A | 9/1997 | Figuly | 424/78.08 |
| 5,670,347 A | 9/1997 | Gopal | |
| 5,674,908 A | 10/1997 | Haces et al. | 514/642 |
| 5,676,954 A | 10/1997 | Brigham | |
| 5,681,944 A | 10/1997 | Crooke et al. | |
| 5,691,460 A | 11/1997 | Duvic et al. | |
| 5,693,509 A | 12/1997 | Cotten et al. | |
| 5,693,773 A | 12/1997 | Kandimalla et al. | |
| 5,703,055 A | 12/1997 | Felgner et al. | 514/44 |
| 5,705,385 A | 1/1998 | Bally et al. | 435/320.1 |
| 5,714,166 A | 2/1998 | Tomalia et al. | |
| 5,719,131 A | 2/1998 | Harris et al. | 514/44 |
| 5,726,298 A | 3/1998 | Hirai et al. | |
| 5,736,387 A | 4/1998 | Paul et al. | |
| 5,736,392 A | 4/1998 | Hawley-Nelson | 435/320.1 |
| 5,744,335 A | 4/1998 | Wolff et al. | 435/172.3 |
| 5,744,625 A | 4/1998 | Nantz | |
| 5,753,613 A | 5/1998 | Ansell et al. | 514/2 |
| 5,756,353 A | 5/1998 | Debs | |
| 5,759,778 A | 6/1998 | Li et al. | |
| 5,759,805 A | 6/1998 | Feldhaus et al. | |
| 5,773,527 A | 6/1998 | Tomalia et al. | |
| 5,780,053 A | 7/1998 | Ashley et al. | |
| 5,783,565 A | 7/1998 | Lee et al. | 514/44 |
| 5,783,566 A | 7/1998 | Mislick | 514/44 |
| 5,785,992 A | 7/1998 | Ansell et al. | 424/450 |
| 5,795,587 A | 8/1998 | Gao et al. | 424/450 |
| 5,824,812 A | 10/1998 | Nantz | |
| 5,827,703 A | 10/1998 | Debs et al. | |
| 5,830,430 A | 11/1998 | Unger et al. | 424/1.21 |
| 5,830,878 A | 11/1998 | Gorman et al. | 514/44 |
| 5,834,439 A * | 11/1998 | Haces et al. | 514/42 |
| 5,837,092 A | 11/1998 | Grieves et al. | |
| 5,837,283 A | 11/1998 | McDonald et al. | 424/450 |
| 5,837,533 A | 11/1998 | Boutin | |
| 5,840,710 A | 11/1998 | Lee et al. | 514/44 |
| 5,854,224 A | 12/1998 | Lockett et al. | |
| 5,861,397 A | 1/1999 | Wheeler | |
| 5,866,613 A | 2/1999 | Bergeron | |
| 5,869,606 A | 2/1999 | Whittaker | |
| 5,869,715 A | 2/1999 | Nantz | |
| 5,871,929 A | 2/1999 | Barnes | |
| 5,877,309 A | 3/1999 | McKay et al. | |

| | | | | | | |
|---|---|---|---|---|---|---|
| 5,885,970 | A | 3/1999 | Bennett et al. | EP | 0 846 680 A1 | 6/1998 |
| 5,886,165 | A | 3/1999 | Kandimalla et al. | FR | 1567214 * | 5/1969 |
| 5,892,071 | A | 4/1999 | Nantz | GB | 892413 | 3/1962 |
| 5,906,922 | A | 5/1999 | Whittaker et al. | WO | WO 87/02061 A1 | 4/1987 |
| 5,908,635 | A | 6/1999 | Thierry ............... 424/450 | WO | WO 90/09180 A1 | 8/1990 |
| 5,908,777 | A | 6/1999 | Lee et al. | WO | WO 90/09786 A1 | 9/1990 |
| 5,916,807 | A | 6/1999 | Bennett et al. | WO | WO 90/11092 A1 | 10/1990 |
| 5,919,772 | A | 7/1999 | Szyf et al. | WO | WO 91/04668 A1 | 4/1991 |
| 5,925,623 | A | 7/1999 | Nantz | WO | WO 91/04753 A1 | 4/1991 |
| 5,929,226 | A | 7/1999 | Padmapriya et al. | WO | WO 91/07947 A1 | 6/1991 |
| 5,935,936 | A | 8/1999 | Fasbender et al. ............ 514/44 | WO | WO 91/15501 A1 | 10/1991 |
| 5,948,614 | A | 9/1999 | Chatterjee | WO | WO 91/16024 A1 | 10/1991 |
| 5,948,767 | A | 9/1999 | Scheule et al. ............... 514/44 | WO | WO 91/17424 A1 | 11/1991 |
| 5,948,925 | A | 9/1999 | Keynes et al. .............. 552/540 | WO | WO 92/06188 A2 | 4/1992 |
| 5,962,533 | A | 10/1999 | Bergeron, Jr. ................ 514/674 | WO | WO 92/06200 A1 | 4/1992 |
| 5,976,567 | A | 11/1999 | Wheeler et al. | WO | WO 92/13570 A2 | 8/1992 |
| 5,977,084 | A | 11/1999 | Szoka | WO | WO 92/20697 A1 | 11/1992 |
| 5,977,306 | A | 11/1999 | Grieve et al. | WO | WO 92/21752 A1 | 12/1992 |
| 5,985,558 | A | 11/1999 | Dean et al. | WO | WO 92/22635 A1 | 12/1992 |
| 6,013,448 | A | 1/2000 | Braxton et al. | WO | WO 93/03709 A1 | 3/1993 |
| 6,020,202 | A | 2/2000 | Jessee ........................ 435/458 | WO | WO 93/05162 | 3/1993 |
| 6,022,874 | A | 2/2000 | Wheeler | WO | WO 93/05162 A1 | 3/1993 |
| 6,022,950 | A | 2/2000 | Murphy | WO | WO 93/07282 A1 | 4/1993 |
| 6,030,626 | A | 2/2000 | Kolattukudy et al. | WO | WO 93/07283 A1 | 4/1993 |
| 6,031,086 | A | 2/2000 | Switzer | WO | WO 93/08130 A1 | 4/1993 |
| 6,051,429 | A | 4/2000 | Hawley-Nelson et al. | WO | WO 93/14778 | 8/1993 |
| 6,054,439 | A | 4/2000 | Szyf et al. | WO | WO 93/19768 A1 | 10/1993 |
| 6,056,938 | A | 5/2000 | Unger et al. | WO | WO 94/02499 A1 | 2/1994 |
| 6,074,826 | A | 6/2000 | Hogan et al. | WO | WO 94/04696 A1 | 3/1994 |
| 6,075,012 | A | 6/2000 | Gebeyehu et al. | WO | WO 94/05624 A1 | 3/1994 |
| 6,086,913 | A | 7/2000 | Tam et al. | WO | WO 94/07899 A1 | 4/1994 |
| 6,090,627 | A | 7/2000 | Kemp et al. | WO | WO 94/08004 A1 | 4/1994 |
| 6,093,564 | A * | 7/2000 | Budowsky et al. ......... 435/238 | WO | WO 91/08191 A1 | 6/1994 |
| 6,103,492 | A | 8/2000 | Yu | WO | WO 94/14475 A1 | 7/1994 |
| 6,110,662 | A | 8/2000 | Foung et al. | WO | WO 94/17093 A1 | 8/1994 |
| 6,110,916 | A | 8/2000 | Haces et al. | WO | WO 94/23751 A1 | 10/1994 |
| 6,126,965 | A | 10/2000 | Kasid et al. | WO | WO 94/27435 | 12/1994 |
| 6,180,784 | B1 | 1/2001 | Wolff et al. | WO | WO 94/27435 | 12/1994 |
| 6,211,140 | B1 | 4/2001 | Sivik et al. | WO | WO 95/02397 A1 | 1/1995 |
| 6,214,804 | B1 | 4/2001 | Felgner et al. | WO | WO 95/16028 A1 | 6/1995 |
| 6,251,390 | B1 | 6/2001 | Harman et al. | WO | WO 95/17373 | 6/1995 |
| 6,287,817 | B1 | 9/2001 | Davis et al. | WO | WO 95/20682 A1 | 8/1995 |
| 6,333,433 | B1 | 12/2001 | Banerjee | WO | WO 95/21259 A1 | 8/1995 |
| 6,335,199 | B1 | 1/2002 | Bischoff et al. | WO | WO 95/24221 A1 | 9/1995 |
| 6,346,516 | B1 | 2/2002 | Banerjee | WO | WO 95/31557 A1 | 11/1995 |
| 6,376,248 | B1 | 4/2002 | Hawley-Nelson et al. | WO | WO 96/01841 A1 | 1/1996 |
| 6,387,395 | B1 | 5/2002 | Eppstein et al. | WO | WO 96/05218 A1 | 2/1996 |
| 6,399,663 | B1 | 6/2002 | Haces et al. ................. 514/642 | WO | WO 96/08723 A1 | 3/1996 |
| 6,503,945 | B1 | 1/2003 | Banerjee | WO | WO 96/10038 A1 | 4/1996 |
| 6,541,649 | B1 | 4/2003 | Banerjee | WO | WO 96/10640 A1 | 4/1996 |
| 6,733,777 | B1 | 5/2004 | Erbacher | WO | WO 96/15811 A1 | 5/1996 |
| 2002/0028447 | A1 | 3/2002 | Li et al. | WO | WO 96/22321 A1 | 7/1996 |
| 2002/0062044 | A1 | 5/2002 | Banerjee | WO | WO 96/22765 A1 | 8/1996 |
| 2002/0077305 | A1 | 6/2002 | Jessee et al. | WO | WO 96/29337 A1 | 9/1996 |
| 2002/0086849 | A1 | 7/2002 | Gebeyehu et al. ............ 514/44 | WO | WO 96/31549 A1 | 10/1996 |
| 2002/0156049 | A1 | 10/2002 | Haces et al. | WO | WO 96/32474 A1 | 10/1996 |
| 2003/0069173 | A1 | 4/2003 | Hawley-Nelson ............... 514/8 | WO | WO 96/35706 A1 | 11/1996 |
| 2005/0014962 | A1 | 1/2005 | Gebeyehu et al. | WO | WO 96/40961 | 12/1996 |
| | | | | WO | WO 97/05265 A1 | 2/1997 |
| | | FOREIGN PATENT DOCUMENTS | | WO | WO 97/09451 A1 | 3/1997 |
| | | | | WO | WO 97/42819 | 11/1997 |
| AU | B-26526/92 | | 5/1993 | WO | WO 9742819 * | 11/1997 |
| DE | 290 877 A5 | | 6/1991 | WO | WO-9742819 A1 * | 11/1997 |
| DE | 44 11 588 C1 | | 9/1995 | WO | WO 98/02190 | 1/1998 |
| DE | 44 11 594 C1 | | 12/1995 | WO | WO 98/06736 A1 | 2/1998 |
| EP | 0 187 702 B1 | | 7/1986 | WO | WO 98/14439 A1 | 4/1998 |
| EP | 0 329 822 A2 | | 8/1989 | WO | WO 98/19709 | 5/1998 |
| EP | 0 304 111 B1 | | 10/1991 | WO | WO 98/32866 A1 | 7/1998 |
| EP | 0 359 347 B1 | | 12/1992 | WO | WO-9829541 A1 * | 7/1998 |
| EP | 0 544 292 A2 | | 6/1993 | WO | WO 98/40499 | 9/1998 |
| EP | 0 684 315 B1 | | 11/1995 | WO | WO 98/40502 | 9/1998 |
| EP | 0 394 111 B1 | | 6/1997 | WO | WO 98/47912 A1 | 10/1998 |
| EP | 0 821 059 A2 | | 1/1998 | WO | WO 99/02190 | 1/1999 |

| WO | WO 99/05302 A1 | 2/1999 |
| WO | WO 99/11809 A1 | 3/1999 |
| WO | WO 99/24559 A2 | 5/1999 |
| WO | WO 99/29712 | 6/1999 |
| WO | WO 99/41410 A1 | 8/1999 |
| WO | WO 99/46400 A1 | 9/1999 |
| WO | WO 00/12454 | 3/2000 |
| WO | WO 00/58488 | 10/2000 |
| WO | WO 00/58488 A2 | 10/2000 |
| WO | WO 00/58488 A3 | 1/2001 |
| WO | WO01/07548 | 2/2001 |
| WO | WO 02/34879 | 5/2002 |
| WO | WO04/083342 | 7/2004 |
| WO | WO04/105697 | 12/2004 |

OTHER PUBLICATIONS

International Search Report for International Application No. PCT/US99/26825, mailed Feb. 22, 2000.

Henkel und Cie. G.m.b.H., abstract No. 68522p, "Low-foaming deteregents containing bisquaternary compounds," *Chem. Abst.* 72(14):116 (Apr. 1970).

Felgner et al. (1993) Keystone Symposium on Genetic Targeted Research and Therapeutics: Antisense and Gene Therapy, Keystone, CO; J. Cell. Biochem. Suppl. 0(17 Part E), p. 206, S306.

Gao, X. and Huang, L. (1993), "Cationic Liposomes and Polymers for Gene Transfer," J. Liposome Res. 3(1):17-30.

Albarella, J.P. et al., "Monoadduct forming photochemical reagents for labeling nucleic acids for hydridization," *Chemical Abstracts* 111:385-386, Abstract No. 130176h, American Chemical Society (1989).

Aumailley, M., et al., "Cell Attachment Properties of Collagen Type VI and Arg-Gly-Asp Dependent Binding to its α2(VI) and α3(VI) Chains," *Exp. Cell Res.* 181:463-474, Academic Press, Inc. (1989).

Barthel, F., et al., "Laboratory Methods: Gene Transfer Optimization with Lipospermine-Coated DNA," *DNA Cell Biol.* 12:553-560, Mary Ann Liebert, Inc. (1993).

Behr, J-P., "Synthetic Gene-Transfer Vectors," *Acc. Chem. Res.* 26:274-278, American Chemical Society (1993).

Bielinska, A., et al., "Regulation of in vitro gene expression using antisense oligonucleotides or antisense expression plasmids transfected using starburst PAMAM dendrimers," *Nucleic Acids Res.* 24:2176-2182, Oxford University Press (1996).

Bonifaci, N., et al., "Nuclear translocation of an exogenous fusion protein containing HIV Tat requires unfolding," *AIDS* 9:995-1000, Rapid Science Publishers (1995).

Braunlin, W.H., et al., "Equilibrium Dialysis Studies of Polyamine Binding to DNA," *Bioploymers* 21:1301-1314, John Wiley & Sons, Inc. (1982).

Budker, V., et al., "Protein/Amphipathic Polyamine Complexes Enable Highly Efficient Transfection with Minimal Toxicity," *Biotechniques* 23:139-147, Eaton Publishing Company (Jul. 1997).

Caminati, G., et al., "Photophysical Investigation of Starburst Dendrimers and Their Interactions with Anionic and Cationic Surfactants," *J. Am. Chem. Soc.* 112:8515-8522, American Chemical Society (1990).

Carrasco, L., "Modification of Membrane Permeability Induced by Animal Viruses Early in Infection," *Virology* 113:623-629, Academic Press, Inc. (1981).

Carrasco, L., and Esteban, M., "Modification of Membrane Permeability in Vaccinia Virus-Infected Cells," *Virology* 117:62-69, Academic Press, Inc. (1982).

Ciccarone, V., et al., "Cationic liposome-mediated transfection of eukaryotic cells: High efficiency nucleic acid delivery with lipofectin®, lipofectace™, and lipofectamine™reagents," *FASEB J.* 7:A1131, Abstract No. 454, Federation of American Societies for Experimental Biology (1993).

Ciccarone, V., et al., "DMRIE-C reagent for transfection of suspension cells and for RNA transfections," *Focus* 17:84-87, Life Technologies, Inc. (1995).

Citovsky, V., et al., "Nuclear Localization of *Agrobacterium* VirE2 Protein in Plant Cells," *Science* 256:1802-1805, American Association for the Advancement of Science (1992).

Cotten, M., et al., "Transferrin-polycation-mediated introduction of DNA into human leukemic cells: Stimulation by agents that affect the survival of transfected DNA or modulate transferrin receptor levels," *Proc. Natl. Acad. Sci. USA* 87:4033-4037, National Academy Press (1990).

Cotten, M., et al., "High-efficiency receptor-mediated delivery of small and large (48 kilobase gene constructs using the endosome-disruption activity of defective or chemically inactivated adenovirus particles," *Proc. Natl. Acad. Sci. USA* 89:6094-6098, National Academy Press (1992).

Curiel, D.T., et al., "Adenovirus enhancement of transferrin-polylysine-mediated gene delivery," *Proc. Natl. Acad. Sci. USA* 88:8850-8854, National Academy Press (1991).

Curiel, D.T. et al., "High-Efficiency Gene Transfer Mediated by Adenovirus Coupled to DNA-Polylysine Complexes," *Hum. Gene. Ther.* 3:147-154, Mary Ann Liebert, Inc. (1992).

Curiel, D.T. et al., "Gene Transfer to Respiratory Epithelial Cells via the Receptor-mediated Endocytosis Pathway," *Am. J. Respir. Cell Mol. Biol.* 6:247-252, American Thoracic Society (1992).

Dattagupta, N., and Albarella, J.P., "Photochemical nucleic acid-labeling reagent having a polyalkylamine spacer," *Chemical Abstracts* 114:383, Abstract No. 114:78227w, American Chemical Society (1991).

Dayhoff, M.o., et al., "A Model of Evolutionary Change in Proteins," in *Atlas of Protein Sequence and Structure*, vol. 5, Suppl. 3, Dayhoff, M.O., ed., National Biomedical Research Foundation, Washington, D.C. pp. 345-352 (1978).

De Robertis, E.M., et al., "Intracellular migration of nuclear proteins in *Xenopus* oocytes," *Nature* 272:254-256, Macmillan Journals, Ltd. (1978).

Dedhar, S., et al., "A Cell Surface Receptor Complex for Collagen Type I Recognizes the Arg-Gly-Asp Sequence," *J. Cell. Biol.* 104:585-593, The Rockefeller University Press (1987).

Demeneix, B.A., et al., "Gene transfer into intact vertebrate embryos," *Int. J. Dev. Biol.* 35:481-484, UBC Press (1991).

Dingwall, C., and Laskey, R.A., "Nuclear targeting sequences—a consensus?" *Trends Biochem. Sci.* 16:478-481, Elsevier Science Publishers, (UK) (1991).

Dingwall, C., et al., "Human immunodeficiency virus 1 tat protein binds trans-activation-responsive region (TAR) RNA in vitro," *Proc. Natl. Acad. Sci. USA* 86:6925-6929, National Academy Press (1989).

Düzgünes, N., et al., "Fusion of Liposomes Containing a Novel Cationic Lipid, N-[2,3-(Dioleyloxy)propyl]-N,N,N-trimethylammonium: Induction by Multivalent Anions and Asymmetric Fusion with Acidic Phospholipid Vesicles," *Biochemistry* 28:9179-9184, American Chemical Society (1989).

Dwarki, V.J., et al., "Cationic Liposome-Mediated RNA Transfection," *Methods Enzymol.* 217:644-654, Academic Press, Inc. (1993).

Epand, R.M., et al., "Peptide Models for the Membrane Destabilizing Actions of Viral Fusion Proteins," *Biopolymers* 32:309-314, John Wiley & Sons, Inc. (1992).

Eytan, G.D., "Use of Liposomes for reconstitution of biological functions," *Biochim. Biophys. Acta* 694:185-202, Elsevier Biomedical Press (1982).

Fawell, S., et al., "Tat-mediated delivery of heterologous proteins into cells," *Proc. Natl. Acad. Sci. USA* 91:664-668, National Academy Press (1994).

Felgner, P.L., and Ringold, G.M., "Cationic liposome-mediated transfection," *Nature* 337:387-388, Nature Publishing Group (1989).

Finlay, D.R., et al., "Nuclear transport in vitro," *J. Cell Sci. Suppl.* 11:225-242, The Company of Biologists Ltd. (1989).

FitzGerald, D.J.P., et al., "Adenovirus-Induced Release of Epidermal Growth Factor and Pseudomonas Toxin into the Cytosol of KB Cells during Receptor-Mediated Endocytosis," *Cell* 32:607-617, Cell Press (1983).

Frankel, A.D., et al., "Activity of synthetic peptides from the Tat protein of human immunodeficiency virus type 1," *Proc. Natl. Acad. Sci. USA* 86:7397-7401, National Academy Press (1989).

Friedlander, D.R., et al., "Functional Mapping of Cytotactin: Proteolytic Fragments Active in Cell-Substrate Adhesion," *J. Cell Biol.* 107:2329-2340, The Rockefeller University Press (1988).

Gao, X., and Huang, L., "Potentiation of Cationic Liposome-Mediated Gene Delivery by Polycations," *Biochemistry* 35:1027-1036, American Chemical Society (1996).

Garcia-Bustos, J., et al., "Nuclear protein localization," *Biochim. Biophys. Acta 1071*:83-101, Elsevier Science Publishers B.V. (1991).

Gardner, J.M., and Hynes, R.O., "Interaction of Fibronectin with Its Receptor on Platelets," *Cell 42*:439-448, Cell Press (1985).

Garrigues, B., and Vidaud, L., "Synthesis of spermine and spermidine selectively substituted on the secondary amine functions," *Chemical Abstracts 111*:593, Abstract No. 23282t, American Chemical Society (1989).

Goldfarb, D.S., et al., "Synthetic peptides as nuclear localization signals," *Nature 322*:641-644, Nature Publishing Group (1986).

Goldfarb, D., and Michaud, N., "Pathways for the nuclear transport of proteins and RNAs," *Trends Cell Biol. 1*:20-24, Elsevier Science Publishers, Ltd (UK) (1991).

Gould-Fogerite, S., et al., "Chimerasome-mediated gene transfer in vitro and in vivo," *Gene 84*:429-438, Elsevier (1989).

Grant, D.S., et al., "Two Different Laminin Domains Mediate the Differentiation of Human Endothelial Cells into Capillary-like Structures In Vitro," *Cell 58*:933-943, Cell Press (1989).

Hackh's Chemical Dictionary, 4th ed., Grant, J., ed., McGraw-Hill Book Company, New York, NY p. 391 (1969).

Haensler, J., and Szoka Jr., F.C., "Polyamidoamine Cascade Polymers Mediate Efficient Transfection of Cells in Culture," *Bioconjug. Chem. 4*:372-379, American Chemical Society (1993).

Hagstrom, J.E., et al., "Complexes of non-cationic liposomes and histone H1 mediate efficient transfection of DNA without encapsulation," *Biochim. Biophys. Acta 1284*:47-55, Elsevier Science B.V. (1996).

Hamana, K., et al., "$N^4$-Methylthermospermine in leguminous seeds," *Chemical Abstracts 117*:427, Abstract No. 117:86723g, American Chemical Society (1992).

Harbottle, R.C., et al., "RGD-mediated gene delivery and expression in epthelial cells," Gene Therapy and Molecular Medicine. Keystone symposium, Steamboat Springs, CO., Mar. 26-Apr. 1, 1995, *J. Cell Biochem. Suppl. 21A*:394, Abstract No. C6-321, Wiley-Liss (1995).

Haverstick, D.M., et al., "Inhibition of Platelet Adhesion to Fibronectin, Fibrinogen, and von Willebrand Factor Substrates by a Synthetic Tetrapeptide Derived From the Cell-Binding Domain of Fibronectin," *Blood 66*:946-952, Harcourt Brace Jovanovich (1985).

Hawley-Nelson, P., et al., "LipofectAMINE™ reagent: A new, higher efficiency polycationic liposome transfection reagent," *Focus 15*:73-79, Life Technologies, Inc. (1993).

Hetschko, M., and Gosselck, J., "Reaktionen von sulfoniumsalzen des 1,3-dithiolans und seiner 2,2-substitutionsprodukte," *Tetrahedron Lett. 17*:1691-1692, Pergamon Press (1972).

Huckett, B., et al., "Evidence for targeted gene transfer by receptor-mediated endocytosis," *Biochem. Pharmacol. 40*:253-263, Pergamon Press (1990).

Humphries, M.J., et al., "Identification of an Alternatively Spliced Site in Human Plasma Fibronectin That Mediates Cell Type-specific Adhesion," *J. Cell Biol. 103*:2637-2647, The Rockefeller University Press (1986).

Humphries, M.J., et al., "Identification of Two Distinct Regions of the Type III Connecting Segment of Human Plasma Fibronectin That Promote Cell Type-specific Adhesion," *J. Biol. Chem. 262*:6886-6892, American Society for Biochemistry and Molecular Biology (1987).

Ito, A., et al., "Synthetic cationic amphiphiles for liposome-mediated DNA transfection," *Biochem. Intl. 22*:235-241, Academic Press Australia (1990).

Kalderon, D., et al., "A Short Amino Acid Sequence Able to Specify Nuclear Location," *Cell 39*:499-509, Cell Press (1984).

Kamata, H., et al., "Amphiphilic peptides enhance the efficiency of liposome-mediated DNA transfection," *Nucleic Acids Res. 22*:536-537, Oxford University Press (1994).

Kaneda, Y., et al., "The Improved Efficient Method for Introducing Macromolecules into Cells Using HVJ (Sendai Virus) Liposomes with Gangliosides," *Exp. Cell Res. 173*:56-69, Academic Press, Inc. (1987).

Kaneda, Y., et al., "Introduction and Expression of the Human Insulin Gene in Adult Rat Liver," *J. Biol. Chem. 264*:12126-12129, The American Society for Biochemistry and Molecular Biology, Inc. (1989).

Kaneda, Y., et al., "Increased Expression of DNA Cointroduced with Nuclear Protein in Adult Rat Liver," *Science 243*:375-378, American Association for the Advancement of Science (1989).

Karlsson, S., et al., "Transfer of genes into hematopoietic cells using recombinant DNA viruses," *Proc. Natl. Acad. Sci. USA 82*:158-162, National Academy Press (1985).

Kielian, M., and Helenius, A., "Entry of Alphaviruses" in *The Togaviridae and Flaviviridae*, Schlesinger, S., and Schlesinger, M.J., eds., Plenum Press, New York, NY, pp. 91-119 (1986).

Kirsch, T., et al., "Cloning, High-Yield Expression in *Escherichia coli*, and Purification of Biologically Active HIV-1 Tat Protein," *Protein Expr. Purif. 8*:75-84, Academic Press, Inc. (1996).

Klappe, K., et al., "Parameters Affecting Fusion between Sendai Virus and Liposomes. Role of Viral Proteins, Liposome Composition, and pH," *Biochemistry 25*:8252-8260, American Chemcial Society (1986).

Knodis, Z., and Valiuliene, S., "New reactions of 1,1-diamines," *Chemical Abstracts 120*:1056, Abstract No. 270276b, American Chemical Society (1994).

Konopka, K., et al., "Enhancement of human immunodeficiency virus type 1 infection by cationic liposomes: the role of CD4, serum and liposome-cell interactions," *J. Gen. Virol. 72*:2685-2696, Society for General Microbiology (1991).

Kraaijeveld, C.A., et al., "The effect of liposomal charge on the neutralizing antibody response against inactivated encephalomyocarditis and Semliki Forest viruses," *Clin. Exp. Immunol. 56*:509-514, Blackwell Scientific Publications (1984).

Kukowska-Latallo, J.F., et al., "Efficient transfer of genetic material into mammalian cells using Starburst polyamidoamine dendrimers," *Proc. Natl. Acad. Sci. USA 93*:4897-4902, National Academy Press (1996).

Lanford, R.E., et al., "Comparison of Diverse Transport Signals in Synthetic Peptide-Induced Nuclear Transport," *Exp. Cell Res. 186*:32-38, Academic Press, Inc. (1990).

Lanford, R.E., et al., "Induction of Nuclear Transport with a Synthetic Peptide Homologous to the SV40 T Antigen Transport Signal," *Cell 46*:575-582, Cell Press (1986).

Lapidot, M., and Loyter, A., "Fusion-Mediated Microinjection of Liposome-Enclosed DNA into Cultured Cells with the Aid of Influenza Virus Glycoproteins," *Exp. Cell Res. 189*:241-246, Academic Press, Inc. (1990).

Lawler, J., et al., "Cell Attachment to Thrombospondin: The Role of ARG-GLY-ASP, Calcium, and Integrin Receptors," *J. Cell. Biol. 107*:2351-2361, The Rockefeller University Press (1988).

Ledley, F.D., "Clinical Considerations in the Design of Protocols for Somatic Gene Therapy," *Hum. Gene Ther. 2*:77-83, Mary Ann Liebert, Inc. (1991).

Legendre, J-Y., et al., "Delivery of Plasmid DNA into Mammalian Cell Lines Using pH-Sensitive Liposomes: Comparison with Cationic Liposomes," *Pharm. Res. 9*:1235-1242, Plenum Publishing Corporation (1992).

Legendre, J-Y., et al., "Cyclic amphipathic peptide-DNA complexes mediate high-efficiency transfection of adherent mammalian cells," *Proc. Natl. Acad. Sci. USA 90*:893-897, National Academy Press (1993).

Life Technologies 1993-1994 Catalog and Reference Guide, pp. 9-19 to 9-21, I-66, R-48 to R-51, Life Technologies, Inc. (1993).

Liljeström, P., and Garoff, H., "A new generation of animal cell expression vectors based on the Semliki Forest virus replicon," *Biotechnology (N Y) 9*:1356-1361, Nature Publishing Company (1991).

Loeffler, J-P., and Behr, J-P., "Gene Transfer into Primary and Established Mammalian Cell Lines with Lipopolyamine-Coated DNA," *Methods Enzymol. 217*:599-618, Academic Press, Inc. (1993).

Loyter, A., et al., "Mechanisms of DNA uptake by mammalian cells: Fate of exogenously added DNA monitored by the use of fluorescent dyes," *Proc. Natl. Acad. Sci. USA 79*:422-426, National Academy Press (1982).

Malone, R.W. et al., "Cationic liposome-mediated RNA transfection," *Proc. Natl. Acad. Sci. USA 86*:6077-6081, National Academy Press (1989).

Mann, D.A., and Frankel, A.D., "Endocytosis and targeting of exogenous HIV-1 Tat protein," *EMBO J. 10*:1733-1739, Oxford University Press (1991).

Marsh, M., et al., "Interactions of Semliki Forest Virus Spike Glycoprotein Rosettes and Vesicles with Cultured Cells," *J. Cell Biol. 96*:455-461, The Rockefeller University Press (1983).

Mason, P.W., et al., "RGD sequence of foot-and-mouth disease virus is essential for infecting cells via the natural receptor but can be bypassed by an antibody-dependent enhancement pathway," *Proc. Natl. Acad. Sci. USA 91*:1932-1936, National Academy Press (1994).

Mazur, W., et al., "The Efficiency of Lipofectin-Mediated Gene Transfer into Porcine and Human Coronary Smooth Muscle Cells is Dramatically Improved by the Influenza Virus Hemagglutinin Antigen," *J. Am. Coll. Cardiol. Suppl. 21*:186A, Abstract No. 889-31, Elsevier (1993).

Miyanohara, A., et al., "Partial Cell-Free Assembly of VSV-G Pseudotyped Retrovirus Particles," Molecular and Cell Biology of Gene Therapy, Keystone, Colorado, meeting date Jan. 19-25, 1998, Abstract No. 007, p. 34, Keystone Symposia (Dec. 1997).

Murata, M., et al., "Modification of the N-terminus of membrane fusion-active peptides blocks the fusion activity," *Biochem. Biophys. Res. Commun. 179*:1050-1055, Academic Press, Inc. (1991).

Neugebauer, J.M., "Detergents: An Overview," *Methods Enzymol. 182*:239-253, Academic Press, Inc. (1990).

Otero, M.J., and Carrasco, L., "Proteins are Cointernalized with Virion Particles during Early Infection," *Virology 160*:75-80, Academic Press, Inc. (1987).

Parente, R.A., et al., "Association of a pH-Sensitive Peptide with Membrane Vesicles: Role of Amino Acid Sequence," *Biochemistry 29*:8713-8719, American Chemical Society (1990).

Parente, R.A., et al., "Mechanism of Leakage of Phospholipid Vesicle Contents Induced by the Peptide GALA," *Biochemistry 29*:8720-8728, American Chemical Society (1990).

Pastan, I.H., and Willingham, M.C., "Journey to the Center of the Cell: Role of the Receptosome," *Science 214*:504-509, American Association for the Advancement of Science (1981).

Pepinsky, R.B., et al., "Specific Inhibition of a Human Papillomavirus E2 Trans-Activator by Intracelluar Delivery of Its Repressor," *DNA Cell Biol. 13*:1011-1019, Mary Ann Liebert, Inc. (1994).

Phalen, T., and Kielian, M., "Cholesterol Is Required for Infection by Semliki Forest Virus," *J. Cell Biol. 112*:615-623, The Rockefeller University Press (1991).

Pierschbacher, M.D., and Ruoslahti, E., "Cell attachment activity of fibronectin can be duplicated by small synthetic fragments of the molecule," *Nature 309*:30-33, Nature Publishing Group (1984).

Pierschbacher, M.D., and Ruoslahti, E., "Influence of Stereochemistry of the Sequence Arg-Gly-Asp-Xaa on Binding Specificity in Cell Adhesion," *J. Biol. Chem. 262*:17294-17298, The American Society for Biochemistry and Molecular Biology, Inc. (1987).

Pinnaduwage, P., et al., "Use of a quaternary ammonium detergent in liposome mediated DNA transfection of mouse L-cells," *Biochim. Biophys. Acta 985*:33-37, Elsevier (1989).

Poste, G., et al., "Lipid Vesicles as Carriers for Introducing Biologically Active Materials into Cells," *Methods Cell Biol. 14*:33-71, Academic Press, Inc. (1976).

"Eukaryotic transcription and Reporter Systems", 1993/94 Promega Catalog, p. 251 Promega Corporation (1993).

Remy, J-S., et al., "Targeted gene transfer into hepatoma cells with lipopolyamine-condensed DNA particles presenting galactose ligands: A stage toward artificial virus," *Proc. Natl. Acad. Sci. USA 92*:1744-1748, National Academy Press (1995).

Rihs, H-P., et al., "The rate of nuclear cytoplasmic protein transport is determined by the casein kinase II site flanking the nuclear localization sequence of the SV40 T-antigen," *EMBO J. 10*:633-639, Oxford University Press (1991).

Rihs, H-P., and Peters, R., "Nuclear transport kinetics depend on phosphorylation-site-containing sequences flanking the karyophilic signal of the Simian virus 40 T-antigen," *EMBO J. 8*:1479-1484, IRL Press (1989).

Rose, J.K., et al., "A New Cationic Liposome Reagent Mediating Nearly Quantitative Transfection of Animal Cells," *Biotechniques 10*:520-525, Eaton Publishing Company (1991).

Rosenkranz, A.A., et al., "Receptor-Mediated Endocytosis and Nuclear Transport of a Transfecting DNA Construct," *Exp. Cell Res. 199*:323-329, Academic Press, Inc. (1992).

Ruoslahti, E., and Pierschbacher, M.D., "New Perspectives in Cell Adhesion: RGD and Integrins," *Science 238*:491-497, American Association for the Advancement of Science (1987).

Sands, J.A., "Virucidal activity of cetyltrimethylammonium bromide below the critical micelle concentration," *FEMS Microbiol. Lett. 36*:261-263, Elsevier (1986).

Schlegel, R., et al., "Inhibition of VSV Binding and Infectivity by Phosphatidylserine: Is Phosphatidylserine a VSV-Binding Site?" *Cell 32*:639-646, Cell Press (1983).

Schlegel, R., and Wade, M., "Biologically Active Peptides of the Vesicular Stomatitis Virus Glycoprotein," *J. Virol. 53*:319-323, American Society for Microbiology (1985).

Scheule, R.K., "Novel Preparation of Functional Sindbis Virosomes," *Biochemistry 25*:4223-4232, American Chemical Society (1986).

Schmid, N., and Behr, J-P., "Location of Spermine and Other Polyamines on DNA As Revealed by Photoaffinity Cleavage with Polyaminobenzenediazonium Salts," *Biochemistry 30*:4357-4361, American Chemical Society (1991).

Seth, P., et al., "Pathway of Adenovirus Entry into Cells," in *Virus Attachment and Entry into Cells*, Crowell, R.L., and Lonberg-Holm, K., eds., American Society for Microbiology, Washington, D.C., pp. 191-195 (1986).

Silver, P.A., "How Proteins Enter the Nucleus," *Cell 64*:489-497, Cell Press (1991).

Smull, C.E., and Ludwig, E.H., "Enhancement of the plaque-forming capacity of poliovirus ribonucleic acid with basic proteins," *J. Bacteriol. 84*:1035-1040, The Williams & Wilkins Company (1962).

Stegmann, T., et al., "Protein-mediated membrane fusion," *Annu. Rev. Biophys. Biophys. Chem. 18*:187-211, Annual Reviews, Inc. (1989).

Sugawa, H., et al., "Large Macromolecules Can Be Introduced into Cultured Mammalian Cells Using Erythrocyte Membrane Vesicles," *Exp. Cell Res. 159*:410-418, Academic Press, Inc. (1985).

Suzuki, S., et al., "Complete amino acid sequence of human vitronectin deduced from cDNA. Similarity of cell attachment sites in vitronectin and fibronectin," *EMBO J. 4*:2519-2524, IRL Press, Ltd. (1985).

Tang, M.X., et al., "In Vitro Gene Delivery by Degraded Polyamidoamine Dendrimers," *Bioconjug. Chem. 7*:703-714, American Chemical Society (1996).

Tikchonenko, T.I., et al., "Transfer of condensed viral DNA into eukaryotic cells using proteoliposomes," *Gene 63*:321-330, Elsevier (1988).

"Transfection Reagent" in *Genetic Engineering News*, Mary Ann Liebert, Inc., p. 12, column 3, (Jun. 1993).

Trubetskoy, V.S., et al., "Use of N-terminal Modified Poly(L-lysine)-Antibody Conjugate as a Carrier for Targeted Gene Delivery in Mouse Lung Endothelial Cells," *Bioconjug. Chem. 3*:323-327, American Chemical Society (1992).

Väänänen, P., and Kääriäinen, L., "Fusion and Haemolysis of Erythrocytes caused by Three Togaviruses: Semliki Forest, Sindbis and Rubella," *J. Gen. Virol. 46*:467-475, Cambridge University Press (1980).

van Zee, K., et al., "A Hydrophobic Protein Sequence Can Override a Nuclear Localization Signal Independently of Protein Context," *Mol. Cell. Biol. 11*:5137-5146, American Society for Microbiology (1991).

Vivès, E., et al., "A Truncated HIV-1 Tat Protein Basic Domain Rapidly Translocates through the Plasma Membrane and Accumulates in the Cell Nucleus," *J. Biol. Chem.* 272:16010-16017, The American Society for Biochemistry and Molecular Biology, Inc. (Jun. 1997).

Wagner, E., et al., "Coupling of adenovirus to transferrin-polylysine/DNA complexes greatly enhances receptor-mediated gene delivery and expression of transfected genes," *Proc. Natl. Acad. Sci. USA* 89:6099-6103, National Academy Press (1992).

Wagner, E., et al., "Transferrin-polycation conjugates as carriers for DNA uptake into cells," *Proc. Natl. Acad. Sci. USA* 87:3410-3414, National Academy Press (1990).

Wagner, E., et al., "Influenza virus hemagglutinin HA-2 N-terminal fusogenic peptides augment gene transfer by transferrin-polylysine-DNA complexes: Toward a synthetic virus-like gene-transfer vehicle," *Proc. Natl. Acad. Sci. USA* 89:7934-7938, National Academy Press (1992).

Wagner, E., et al., "DNA-Binding Transferrin Conjugates as Functional Gene-Delivery Agents: Synthesis by Linkage of Polylysine or Ethidium Homodimer to the Transferrin Carbohydrate Moiety," *Bioconjug. Chem.* 2:226-231, American Chemical Society (1991).

Walker, C., et al., "Cationic lipids direct a viral glycoprotein into the class I major histocompatibility complex antigen-presentation pathway," *Proc. Natl. Acad. Sci. USA* 89:7915-7918, National Academy Press (1992).

Wayner, E.A., et al., "Identification and Characterization of the T Lymphocyte Adhesion Receptor for An Alternative Cell Attachment Domain (CS-1) in Plasma Fibronectin," *J. Cell Biol.* 109:1321-1330, The Rockefeller University Press (1989).

Weinstock, L.T., et al., "Synthesis of New Polyamine Derivatives for Cancer Chemotherapeutic Studies," *J. Pharm. Sci.* 70:956-959, American Pharmaceutical Association (1981).

Wickham, T.J., et al., "Targeting of adenovirus penton base to new receptors through replacement of its RGD motif with other receptor-specific peptide motifs," *Gene Ther.* 2:750-756, Stockton Press (1995).

Wilson, J.M., et al., "Hepatocyte-directed Gene Transfer in Vivo Leads to Transient Improvement of Hypercholesterolemia in Low Density Lipoprotein Receptor-deficient Rabbits," *J. Biol. Chem.* 267:963-967, The American Society for Biochemistry and Molecular Biology, Inc. (1992).

Wolff, J.A., et al., "Direct Gene Transfer into Mouse Muscle in Vivo," *Science* 247:1465-1468, American Association for the Advancement of Science (1990).

Wu, G.Y., and Wu, C.H., "Receptor-mediated Gene Delivery and Expression in Vivo," *J. Biol. Chem.* 263:14621-14624, The American Association for Biochemistry and Molecular Biology, Inc. (1988).

Wu, C.H., et al., "Targeting Genes: Delivery and Persistent Expression of a Foreign Gene Driven by Mammalian Regulatory Elements in Vivo," *J. Biol. Chem.* 264:16985-16987, The American Society for Biochemistry and Molecular Cell Biology, Inc. (1989).

Wu, G.Y., and Wu, C.H., "Evidence for Targeted Gene Delivery to Hep G2 Hepatoma Cells in Vitro," *Biochemistry* 27:887-892, American Chemical Society (1988).

Wu, G.Y., et al., "Receptor-mediated Gene Delivery in Vivo: Partial correction of genetic analbuminemia in nagase rats," *J. Biol. Chem.* 266:14338-14342, The American Society for Biochemistry and Molecular Biology, Inc. (1991).

Yagi, K., et al., "Incorporation of Histone into Liposomes Increases the Efficiency of Liposome-Mediated Gene Transfer," *J. Clin. Biochem. Nutr.* 10:21-25, Institute of Applied Biochemistry (1991).

Yoshimura, K., et al., "Adenovirus-mediated Augmentation of Cell Transfection with Unmodified Plasmid Vectors," *J. Biol. Chem.* 268:2300-2303, The American Association for Biochemistry and Molecular Biology, Inc. (1993).

Young, J.D.-E., et al., "Interaction of Enveloped Viruses with Planar Bilayer Membranes: Observations on Sendai, Influenza, Vesicular Stomatitis, and Semliki Forest Viruses," *Virology* 128:186-194, Academic Press, Inc. (1983).

Zenke, M., et al., "Receptor-mediated endocytosis of transferrin-polycation conjugates: An efficient way to introduce DNA into hematopoietic cells," *Proc. Natl. Acad. Sci. USA* 87:3655-3659, National Academy Press (1990).

Zhou, X., and Huang, L., "DNA transfection mediated by cationic liposomes containing lipopolylysine: characterization and mechanism of action," *Biochim. Biophys. Acta* 1189:195-203, Elsevier Science B.V. (1994).

Zhu, Z., et al., "Transformation of tobacco protoplasts with DNA entrapped in pH-sensitive liposomes," *Plant Cell, Tissue & Organ Cult.* 22:135-145, Kluwer Academic Publishers (1990).

CAPLUS, Acession No. 1972:461856, STNEasy CAPLUS English language abstract for for Hetschko, M., and Gosselck, J., "Reaktionen von sulfoniumsalzen des 1,3-dithiolans und seiner 2,2-substitutionsprodukte," *Tetrahedron Lett.* 17:1691-1692, Pergamon Press (1972) (Document AT23).

Dialog File 351, Accession No. 7672839, Derwent WPI English language abstract for EP 0 304 111 B1 (Document AN4).

Dialog File 351, Accession No. 8628544, Derwent WPI English language abstract for WO 91/04668 A1 (Document AO4).

Dialog File 351, Accession No. 8822189, Derwent WPI English language abstract for DD 290 877 A5 (Document AN5).

Dialog File 351, Accession No. 9150067, Derwent WPI English language abstract for WO 92/13570 A2 (Document AL6).

Dialog File 351, Accession No. 9417386, Derwent WPI English language abstract for WO 93/07282 A1 (Document AL7).

Dialog File 351, Accession No. 9440951, Derwent WPI English language abstract for WO 93/07283 A1 (Document AM7).

Dialog File 351, Accession No. 9483543, Derwent WPI English language abstract for EP 0 544 292 A2 (Document AO7).

Dialog File 351, Accession No. 10073779, Derwent WPI English language abstract for WO 94/23751 A1 (Document AN8).

Dialog File 351, Accession No. 10968033, Derwent WPI English language abstract for WO 96/31549 A1 (Document AO10).

Albrecht, T., et al., "Cationic lipide mediated transfer of c-ab1 and bcr antisense oligonucleotides to immature normal myeloid cells: uptake, biological effects and modulation of gene expression," *Ann. Hematol.* 72:73-79, Springer-Verlag (1996).

Aslanyan, V.M. et al., "Conformation and Thermal Stability of DNA in Aqueous Solutions of $\beta$-Alanine and $\gamma$-Aminobutyric Acid," *Biophysics* 29:615-620, Pergamon Press, Ltd. (1984).

Astatke, M., et al., "How *E. coli* DNA Polymerase I (Klenow fragment) Distinguishes between Deoxy- and Dideoxynucleotides," *J. Mol. Biol.* 278:147-165, Academic Press, Ltd. (Apr. 1998).

Barnes, W.M., "The fidelity of Taq polymerase catalyzing PCR is improved by an N-terminal deletion," *Gene* 112:29-35, Elsevier Science Publishers B.V. (1992).

Baskaran, N., et al., "Uniform Amplification of a Mixture of Deoxyribonucleic Acids with Varying GC Content," *Genome Res.* 6:633-638, Cold Spring Harbor Laboratory Press (1996).

Behr, J-P., "Gene Transfer with Synthetic Cationic Amphiphiles: Prospects for Gene Therapy," *Bioconjug. Chem.* 5:382-389, American Chemical Society (1994).

Benoist, C., et al., "In vivo sequence requirements of the SV40 early promoter region," *Nature* 290:304-310, Macmillan Journals, Ltd. (1981).

Bonfanti, M., et al., "p21$^{WAF1}$-derived Peptides Linked to an Internalization Peptide Inhibit Human Cancer Cell Growth," *Cancer Res.* 57:1442-1446, American Association for Cancer Research (Apr. 1997).

Böttger, M., et al., "Condensation of vector DNA by the chromosomal protein HMG1 results in efficient transfection," *Biochim. Biophys. Acta* 950:221-228, Elsevier Science Publishers B.V. (1988).

Boussif, O., et al., "A versatile vector for gene and oligonucleotide transfer into cells in culture and in vivo: Polyethylenimine," *Proc. Natl. Acad. Sci. USA* 92:7297-7301, National Academy Press (1995).

Brunette, E., et al., "Lipofection does not require the removal of serum," *Nucleic Acids Res.* 20:1151, Oxford University Press (1992).

Buche, A., et al., "Glycine and other amino compounds prevent chromatin precipitation at physiological ionic strength," *FEBS Lett.* 247:367-370, Elsevier Science Publishers B.V. (1989).

Buche, A., et al., "Organic Osmotic Effectors and Chromatin Structure," *J. Biomol. Struct. & Dynam.* 8:601-618, Adenine Press (1990).

Buche, A., et al., "Effect of Organic Effectors on Chromatin Solubility, DNA-Histone H1 Interactions, DNA and Histone H1 Structures," *J. Biomol. Struct. & Dynam.* 11:95-119, Adenine Press (1993).

Cánovas, D., et al., "Osmoprotectants in *Halomonas elongata*: High-Affinity Betaine Transport System and Choline-Betaine Pathway," *J. Bacteriol.* 178:7221-7226, American Society for Microbiology (1996).

Cánovas, D., et al., "Isolation and Characterization of Salt-sensitive Mutants of the Moderate Halophile *Halomonas elongata* and Cloning of the Ectoine Synthesis Genes," *J. Biol. Chem.* 272:25794-25801, The American Society for Biochemistry and Molecular Biology, Inc. (Oct. 1997).

Carninci, P., et al., "Thermostabilization and thermoactivation of thermolabile enzymes by trehalose and its application for the synthesis of full length cDNA," *Proc. Natl. Acad. Sci. USA* 95:520-524, National Academy Press (Jan. 1998).

Chambers, S.T., et al., "Dimethylthetin Can Substitute for Glycine Betaine as an Osmoprotectant Molecule for *Escherichia coli*," *J. Bacteriol.* 169:4845-4847, American Society for Microbiology (1987).

Chen, X., et al., "A self-initiating eukaryotic transient gene expression system based on cotransfection of bacteriophage T7 RNA polymerase and DNA vectors containing a T7 autogene," *Nucleic Acids Res.* 22:2114-2120, Oxford University Press (1994).

Cohen, J., "Naked DNA Points Way to Vaccines," *Science* 259:1691-1692, American Association for the Advancement of Science (1993).

Cotten, M., and Wagner, E., "Non-viral approaches to gene therapy," *Curr. Opin. Biotechnol.* 4:705-710, Current Biology, Ltd. (1993).

Deamer, D.W., and Uster, P.S., "Liposome Preparation: Methods and Mechanisms," in *Liposomes*, Marc J. Ostro, ed., Marcel Dekker, Inc., New York, NY, pp. 27-51 (1983).

Dean, N.M., and McKay, R., "Inhibition of protein kinase C-α expression in mice after systemic administration of phosphorothioate antisense oligodeoxynucleotides," *Proc. Natl. Acad. Sci. USA* 91:11762-11766, National Academy Press (1994).

Elliot, G., and O'Hare, P., "Intercellular trafficking of VP22-GFP fusion proteins," Gene Ther. 6:149-151, Stockton Press (Jan. 1999).

Felgner, P.L., and Holm, M., "Cationic Liposome-Mediated Transfection," *Focus* 11:21-25, Life Technologies, Inc. (1989).

Felgner, P.L., and Rhodes, G., "Gene therapeutics," *Nature* 349:351-352, Macmillan Journals, Ltd. (1991).

Flaman, J-M., et al., "A rapid PCR fidelity assay," *Nucleic Acids Res.* 22:3259-3260, Oxford University Press (1994).

Flock, S., et al., "Osmotic Effectors and DNA Structure: Effect of Glycine on Precipitation of DNA by Multivalent Cations" *J. Biomol. Struct. Dyn.* 13:87-102, Adenine Press (1995).

Flock, S., et al., "Dielectric Constant and Ionic Strength Effects on DNA Precipitation," *Biophys. J.* 70:1456-1465, Biophysical Society (1996).

Flock, S., et al., "$^{23}$Na NMR Study of the Effect of Organic Osmolytes on DNA Counterion Atmosphere," *Biophys. J.* 71:1519-1529, Biophysical Society (1996).

Foecking, M.K., and Hofstetter, H., "Powerful and versatile enhancer-promoter unit for mammalian expression vectors," *Gene* 45:101-105, Elsevier Science Publishers B.V. (1986).

Frackman, S., et al., "Betaine and DMSO: Enhancing Agents for PCR," *Promega Notes* 65:27-29, Promega (Feb. 1998).

Fritz, J.D., et al., "Gene Transfer into Mammalian Cells Using Histone-Condensed Plasmid DNA," *Hum. Gene Ther.* 7:1395-1404, Mary Ann Liebert, Inc. (1996).

Giles, R.V., "Antisense oligonucleotide technology: From EST to therapeutics," *Curr. Opin. Mol. Ther.* 2:238-252, PharmaPress, Ltd. (Jun. 2000).

Goldman, C.K., et al., "In vitro and in vivo gene delivery mediated by a synthetic polycationic amino polymer," *Nat. Biotechnol.* 15:462-466, Nature America Publishing (May 1997).

Gorman, C., "High Efficiency Gene Transfer into Mammalian Cells," in *DNA Cloning*, vol. II, Glover, D.M., ed., IRL Press, Washington, D.C., pp. 143-190 (1985).

Gouesbet, G., et al., "Characterization of the *Erwinia chrysanthemi* Osmoprotectant Transporter Gene ousA," *J. Bacteriol.* 178:447-455, American Society for Microbiology (1996).

Gubler, U., and Hoffman, B.J., "A simple and very efficient method for generating cDNA libraries," *Gene* 25:263-269, Elsevier Science Publishers (1983).

Haensler, J., and Szoka Jr., F.C., "Polyamidoamine Cascade Polymers Mediate Efficient Transfection of Cells in Culture," *Bioconjug. Chem.* 4:372-379, American Chemical Society (1993).

Harrison, G.S., et al., "Optimization of Gene Transfer Using Cationic Lipids in Cell Lines and Primary Human CD4+and CD34+Hematopoietic Cells," *BioTechniques* 19:816-823, Eaton Publishing Company (1995).

Hazinski, T.A., et al., "Localization and Induced Expression of Fusion Genes in the Rat Lung," *Am. J. Respir. Cell Mol. Biol.* 4:206-209, American Thoracic Society (1991).

Hengen, P.N., "Optimizing multiplex and LA-PCR with betaine," *Trends Biochem. Sci.* 22:225-226, Elsevier Science, Ltd. (Jun. 1997).

Henke, W., et al., "Betaine improves the PCR amplification of GC-rich DNA sequences," *Nucl. Acids Res.* 25:3957-3958, Oxford University Press (Oct. 1997).

Heywood, S.M., "tcRNA as a naturally occurring antisense RNA in eukaryotes," *Nucleic Acids Res.* 14:6771-6772, IRL Press (1986).

Hogrefe, H., et al., "Novel PCR Enhancing Factor Improves Performance of Pfu DNA Polymerase," *Strategies* 10:93-96, Stratagene Cloning Systems (Aug. 1997).

Holt, C.E., et al., "Lipofection of cDNAs in the Embryonic Vertebrate Central Nervous System," *Neuron* 4:203-214, Cell Press (1990).

Hope, M.J., et al., "Generation of Multilamellar and Unilamellar Phospholipid Vesicles," *Chem. Phys. Lipids* 40:89-107, Elsevier Scientific Publishers Ireland, Ltd. (1986).

Houssier, C., et al., "Effects of Compensatory Solutes on DNA and Chromatin Structural Organization in Solution," *Comp. Biochem. Physiol.* 117A:313-318, Elsevier Science, Inc. (Jul. 1997).

Houts, G.E., et al., "Reverse Transcriptase from Avian Myeloblastosis Virus," *J. Virol.* 29:517-522, American Society for Microbiology (1979).

Iakobashvili, R., and Lapidot, A., "Low temperature cycled PCR protocol for Klenow fragment of DNA polymerase I in the presence of proline," *Nucleic Acids Res.* 27:1566-1568, Oxford University Press (Mar. 1999).

Innis, M.A., "PCR with 7-Deaza-2'-Deoxyguanosine Triphosphate," in *PCR Protocols: A Guide to Methods and Applications*, Innis, M.A., et al., eds., Academic Press, Inc., San Diego, CA, pp. 54-59 (1990).

Instruction Manual for "GeneTrapper™ cDNA Positive Selection System," Catalog No. 10356-020, GIBCO BRL, Life Technologies, Gaithersburg, MD, pp. 1-26.

Iyer, R.P., et al., "The Automated Synthesis of Sulfur-Containing Oligodeoxyribonucleotides Using 3H-1,2-Benzodithiol-3-one 1,1-Dioxide as a Sulfur-Transfer Reagent," *J. Org. Chem.* 55:4693-4699, American Chemical Society (1990).

Iyer, R.P., et al., "3H-1,2-Benzodithiole-3-one 1,1-Dioxide as an Improved Sulfurizing Reagent in the Solid-Phase Synthesis of Oligodeoxyribonucleoside Phosphorothioates," *J. Am. Chem. Soc.* 112:1253-1254, American Chemical Society (1990).

Jakob, R., and Saenger, W., "Reversed-phase ion-pair chromatographic separation of ribulose 1,5-bisphosphate from 3-phosphoglycerate and its application as a new enzyme assay for RuBP carboxylase/oxygenase," *FEBS Lett.* 183:111-114, Elsevier Science Publishers B.V. (1985).

Johnstone, A., and Thorpe, R., "Production of antibodies," in *Immunochemistry in Practice*, Johnstone, A., and Thorpe, R., eds., Blackwell Scientific Publications, Oxford, Great Britain, pp. 30-47, (1987).

Joung, I., and Engler, J.A., "Mutations in Two Cysteine-Histidine-Rich Clusters in Adenovirus Type 2 DNA Polymerase Affect DNA Binding," *J. Virol.* 66:5788-5796, American Society for Microbiology (1992).

Kondakova, N.V., et al., "Effect of Low-molecular Amines on the Conformation and Stability of the Double Helix," *Mol. Biol. (Mosk.)* 9:742-746, Izdatelstvo Nauka (1975).

English Language Translation for Kondakova, N.V., et al., "Effect of Low-molecular Amines on the Conformation and Stability of the Double Helix," *Mol. Biol. (Mosk.)* 9:742-746, Izdatelstvo Nauka (1975) (Document AR77).

Kotewicz, M.L., et al., "Isolation of cloned Moloney murine leukemia virus reverse transcriptase lacking ribonuclease H activity," *Nucleic Acids Res.* 16:265-277, IRL Press, Ltd. (1988).

Landre, P.A., et al., "The use of cosolvents to enhance amplification by the polymerase chain reaction," in *PCR Strategies*, Innis, M.A., et al., eds., Academic Press, San Diego, CA, pp. 3-16 (1995).

Langel, U., et al., "Cell penetrating PNA constructs," *J. Neurochem.* 69 (suppl):S260, Abstract B, Lippincott-Raven Publishers (Jul. 1997).

Lau, Q.C., et al., "Abrogation of c-Raf expression induces apoptosis in tumor cells," *Oncogene* 16:1899-1902, Stockton Press (Apr. 1998).

Lawyer, F.C., et al., High-level Expression, Purification, and Enzymatic Characterization of Full-Length *Thermus aquaticus* DNA Polymerase and a Truncated Form Deficient in 5' to 3' Exonuclease Activity, *PCR Methods Appl.* 2:275-287, Cold Spring Harbor Laboratory Press (1993).

Le Rudulier, D. et al., "Molecular Biology of Osmoregulation," *Science* 224:1064-1068, American Association for the Advancement of Science (1984).

Li, C.-J., et al., "Nonprotein amino acids from seeds of *Cycas circinalis* and *Phaseolus vulgaris*," *Phytochemistry* 42:443-445, Pergamon Press (1996).

1995-96 GIBCO/BRL Product Catalogue and Reference Guide, pp. 19-10 and 19-12, Life Technologies, Inc. (1995).

Liu, X., et al., "Hypoglycemia-induced c-Jun Phosphorylation Is Mediated by c-Jun N-terminal Kinase 1 and Lyn Kinase in Drug-resistant Human Breast Carcinoma MCF-7/ADR Cells," *J. Biol. Chem.* 272:11690-011693, The American Society for Biochemistry and Molecular Biology, Inc. (May 1997).

Malin, G., and Lapidot, A., "Induction of Synthesis of Tetrahydropyrimidine Derivatives in *Streptomyces* Strains and Their Effect on *Escherichia coli* in Response to Osmotic and Heat Stress," *J. Bacteriol.* 178:385-395, American Society for Microbiology (1996).

Maniatis, T., et al., "The Isolation of Structural Genes from Libraries of Eucaryotic DNA," *Cell* 15:687-701, MIT Press (1978).

Marquet, R. and Houssier, C., "Thermodynamics of Cation-Induced DNA Condensation," *J. Biomol. Struct. & Dynam.* 9:159-167, Adenine Press (1991).

Mizuno, T., et al., "A unique mechanism regulating gene expression: Translational inhibition by a complementary RNA transcript (micRNA)," *Proc. Natl. Acad. Sci. USA* 81:1966-1970, National Academy Press (1984).

Monia, B.P., et al., "Sequence-specific antitumor activity of a phosphorothioate oligodeoxyribonucleotide targeted to human C-raf kinase supports an antisense mechanism of action in vivo," *Proc. Natl. Acad. Sci. USA* 93:15481-15484, National Academy Press (1996).

Murphy, A.L., and Murphy, S.J., "Catch VP22: the hitch-hiker's ride to gene therapy?" *Gene Ther.* 6:4-5, Nature Publishing Group (Jan. 1999).

Mytelka, D.S., and Chamberlin, M.J., "Analysis and suppression of DNA polymerase pauses associated with a trinucleotide consensus," *Nucleic Acids Res.* 24:2774-2781, Oxford University Press (1996).

McCluskie, M.J., et al., "Direct Gene Transfer to the Respiratory Tract of Mice with Pure Plasmid and Lipid-Formulated DNA," *Antisense Nucleic Acid Drug Dev.* 8:401-414, Mary Ann Liebert, Inc. (Oct. 1998).

Nabel, G.J., et al., "Direct gene transfer for treatment of human cancer," *Ann. NY Acad. Sci.* 772:227-231, New York Academy of Sciences (1995).

Nabel, G.J., et al., "Immune responses in human melanoma after transfer of an allogeneic class I major histocompatibility complex gene with DNA-liposome complexes," *Proc. Natl. Acad. Sci. USA* 93:15388-15393, National Academy Press (1996).

Neckers, L.M., "Cellular Internalization of Oligodeoxynucleotides," in *Antisense Research and Applications*, Crooke, S.T. and Lebleu, B., eds., CRC Press, Inc., Boca Raton, FL, pp. 451-460 (1993).

Neurath, A.R. et al., "B cell epitope mapping of human immunodeficiency virus envelope glycoproteins with long (19- to 36-residue) synthetic peptides," *J. Gen. Virol.* 71:85-95, Society for General Microbiology (1990).

Niidome, T., et al., "Binding of Cationic α-Helical Peptides to Plasmid DNA and Their Gene Transfer Abilities into Cells," *J. Biol. Chem.* 272:15307-15312, The American Society for Biochemistry and Molecular Biology, Inc. (Jun. 1997).

Okayama, H., and Berg, P., "High-Efficiency Cloning of Full-Length cDNA," *Mol. Cell. Biol.* 2:161-170, American Society for Microbiology (1982).

Panaccio, M., et al., "FoLT PCR: A Simple PCR Protocol for Amplifying DNA Directly from Whole Blood," *BioTechniques* 14:238-243, Eaton Publishing Company (1993).

Paterson, B.M., et al., "Structural gene identification and mapping by DNA·mRNA hybrid-arrested cell-free translation," *Proc. Natl. Acad. Sci. USA* 74:4370-4374, National Academy Press (1977).

Polesky, A.H., et al., "Identification of Residues Critical for the Polymerase Activity of the Klenow Fragment of DNA Polymerase I from *Escherichia coli*," *J. Biol. Chem.* 265:14579-14591, The American Society for Biochemistry and Molecular Biology, Inc. (1990).

Prochiantz, A., "Getting hydrophilic compounds into cells: lessons from homeopeptides," *Curr. Opin. Neurobiol.* 6:629-634, Current Biology, Ltd. (1996).

Prochiantz, A., "Peptide nucleic acid smugglers," *Nat. Biotechnol.* 16:819-820, Nature America Publishing (Sep. 1998).

Rafferty, J.A., and Fletcher, H.L., "Sequence analysis of a family of highly repeated DNA units in *Stauroderus scalaris* (Orthoptera)" *Intl. J. Genome Res.* 1:1-16, World Scientific Publishing Company (1992).

Rajendrakumar, C.S.V., et al., "DNA helix destabilization by proline and betaine: possible role in the salinity tolerance process," *FEBS Lett.* 410:201-205, Elsevier Science B.V. (Jun. 1997).

Randall, K., et al., "Accumulation of natural and synthetic betaines by a mammalian renal cell line," *Biochem. Cell Biol.* 74:283-287, National Research Council of Canada (1996).

Randall, K., et al., "Natural and synthetic betaines counter the effects of high NaCl and urea concentrations," *Biochim. Biophys. Acta* 1291:189-194, Elsevier Science B.V. (1996).

Rees, W.A., et al., "Betaine Can Eliminate the Base Pair Composition Dependence of DNA Melting," *Biochemistry* 32:137-144, American Chemical Society (1993).

Rothenberg, M., et al., "Oligodeoxynucleotides as Anti-Sense Inhibitors of Gene Expression: Therapeutic Implications," *J. Natl. Cancer Inst.* 81:1539-1544, Oxford University Press (1989).

Saiki, R.K., et at., "Primer-Directed Enzyumatic Amplification of DNA with a Thermostable DNA Polymerase," *Science* 239:487-491, American Association for the Advancement of Science (1988).

Shepard, A.R., and Rae, J.L., "Magnetic bead capture of cDNAs from double-stranded plasmid cDNA libraries," *Nucleic Acids Res.* 25:3183-3185, Oxford University Press (Aug. 1997).

Bioactive Peptides, 1993 Sigma Chemical Company Catalogue, St. Louis, MO, pp. 1028-1034, Sigma Chemical Company (1993).

Soltis, D.A., and Skalka, A.M., "The α and β chains of avian retrovirus reverse transcriptase independently expressed in *Escherichia coli*: Characterization of enzymatic activities," *Proc. Natl. Acad. Sci. USA* 85:3372-3376, National Academy Press (1988).

Stopeck, A.T., et al., "Phase I Study of Direct Gene Transfer of an Allogeneic Histocompatibility Antigen, HLA-B7, in Patients With Metastatic Melanoma," *J. Clin. Oncol.* 15:341-349, American Society of Clinical Oncology (Jan. 1997).

Szoka Jr., F., and Papahadjopoulos, D., "Comparative properties and methods of preparation of lipid vesicles (liposomes)," *Annu. Rev. Biophys. Bioeng.* 9:467-508, Annual Reviews, Inc. (1980).

Tang, D-c., et al., "Genetic immunization is a simple method for eliciting an immune response," *Nature* 356:152-154, Nature Publishing Group (1992).

Thompson, L., "A Shot in the Arm for Vaccine Problems," Washington Post, p. AO3 (Jun. 7, 1993).

Uhlmann, E., and Peyman, A., "Antisense Oligonucleotides: A New Therapeutic Principle," *Chem. Rev.* 90:544-584, American Chemical Society (1990).

Ulmer, J.B., et al., "Heterologous Protection Against Influenza by Injection of DNA Encoding a Viral Protein," *Science* 259:1745-1749, American Association for the Advancement of Science (1993).

Urdea, M.S., "Branched DNA Signal Amplification," *Bio/Technology* 12:926-928, Nature Publishing Company (1994).

van der Krol, A.R., et al., "Modulation of Eukaryotic Gene Expression by Complementary RNA or DNA Sequences," *BioTechniques* 6:958-976, Eaton Publishing Company (1988).

Varadaraj, K. and Skinner, D.M., "Denaturants or cosolvents improve the specificity of PCR amplification of a G+C-rich DNA using genetically engineered DNA polymerases," *Gene* 140:1-5, Elsevier Science B.V. (1994).

Voytik-Harbin, S.L., et al., "Identification of Extractable Growth Factors From Small Intestinal Submucosa," *J. Cell. Biochem.* 67:478-491, Wiley-Liss, Inc. (Dec. 1997).

Wagner, E., et al., "Transferrin-polycation-DNA complexes: The effect of polycations on the structure of the complex and DNA delivery to cells," *Proc. Natl. Acad. Sci. USA* 88:4255-4259, National Academy Press (1991).

Wang, B., et al., "Gene inoculation generates immune responses against human immunodeficiency virus type 1," *Proc. Natl. Acad. Sci. USA* 90:4156-4160, National Academy Press (1993).

Weissensteiner, T., and Lanchbury, J.S., "Strategy for Controlling Preferential Amplification and Avoiding False Negatives in PCR Typing," *BioTechniques* 21:1102-1108, Eaton Publishing Company (1996).

Wen, W., et al., "Identification of a Signal for Rapid Export of Proteins from the Nucleus," *Cell* 82:463-473, Cell Press (1995).

Wickstrom, E.I., et al., "Human promyelocytic leukemia HL-60 cell proliferation and c-myc protein expression are inhibited by an antisense pentadecadeoxynucleotide targeted against c-myc mRNA," *Proc. Natl. Acad. Sci. USA* 85:1028-1032, National Academy Press (1988).

Wickstrom, E., et al., "Down-Regulation of c-MYC Antigen Expression in Lymphocytes of Eμ-c-myc Transgenic Mice Treated with Anti-c-myc DNA Methylphosphonates," *Cancer Res.* 52:6741-6745, American Association for Cancer Research (1992).

Woodford, K., et al., "The Use of K'-free buffers eliminates a common cause of premature chain termination in PCR and PCR sequencing," *Nucleic Acids Res.* 23:539, Oxford University Press (1995).

Zaitsev, S.V., et al., "H1 and HMG17 extracted from calf thymus nuclei are efficient DNA carriers in gene transfer," *Gene Ther.* 4:586-592, Stockton Press (Jun. 1997).

"Voyager™—The Power of Translocation," *Expressions* 6:6, Life Technologies, Inc. (Feb. 1999).

Dialog File 351, Accession No. 8899481, Derwent WPI English language abstract for WO 93/08130 A1 (Document AO12).

Dialog File 351, Accession No. 10428036, Derwent WPI English language abstract for DE 44 11 588 C1 (Document AN14).

Dialog File 351, Accession No. 10524091, Derwent WPI English language abstract for DE 44 11 594 C1 (Document AP14).

Dialog File 351, Accession No. 10655226, Derwent WPI English language abstract for WO 96/08723 A1 (Document AL15).

Co-pending U.S. Appl. No. 09/266,935, filed Mar. 12, 1999, inventors Li et al. (not published).

Co-pending U.S. Appl. No. 09/570,526, filed May 12, 2000, inventors Astatke et al. (not published).

Co-pending U.S. Appl. No. 09/608,066, filed Jun. 30, 2000, inventors Astatke et al. (not published).

Asokan, A. and Cho, M.J. (2004), "Cytosolic Delivery of Macromolecules. 3. Synthesis and Characterization of Acid-Sensitive Bis-Detergents," Bioconj. Chem. 15:1166-1173.

Banerjee, R. et al. (1999), "Novel Series of Non-Glycerol-Based Cationic Transfection Lipids for Use in Liposomal Gene Delivery," J. Med. Chem. 42:4292-4299.

Bennett, M.J. et al. (1997), "Cationic Lipid-Mediated Gene Delivery to Murine Lung: Correlation of Lipid Hydration with in Vivo Transfection Activity," J. Med. Chem. 40:4069-4078.

Bergeron, R.J. et al. (1996), "Metabolically Programmed Polyamine Analogue Antidiarrheals," J. Med. Chem. 39:2461-2471.

Mack, K.D. (Feb. 1994), "Cationic lipid enhances in vitro receptor-mediated transfection," Am. J. Med. Sci. 307:138-143.

Mazur, W. et al. (Feb. 1993), "Direct Gene Transfer into the Coronary Arteries of Intact Animals via Infusion Balloon Catheters: Comparison of Canine and Procine Model Systems," J. Am. Coll Cardiol. 21(2):186A.

Singh, R.S. et al. (2002), "Anchor Dependency for Non-Glycerol Based Cationic Lipofectins: Mixed Bag of Regular and Anomalous Transfection Profiles," Chem. Eur. J. 8:900-909.

Trubetskoy, V.S. et al. (Jul. 1992), "Cationic liposomes enhance targeted delivery and expression of exogenous DNA mediated by N-terminal modified poly(L-lysine)-antibody conjugate in mouse lung endothelial cells," Biochim. Biophys. Acta, 1131:311-313.

Bangham, A.D. et al., "Diffusion of Univalent Ions across the Lamellae of Swollen Phospholipids," *J. Mol. Biol.* 13:238-252 (1965).

Behr, J.-P. et al., "Efficient gene transfer into mammalian primary endocrine cells with Lipopolyamine-coated DNA," *Proc. Natl. Acad. Sci. USA* 86:6982-6986 (Sep. 1989).

Felgner, P.L. et al., "Lipofection: A highly efficient, lipid-mediated DNA-transfection procedure," *Proc. Natl. Acad. Sci. USA* 84:7413-7417 (Nov. 1987).

Fukunaga, M. et al., "Liposome Entrapment Enhances the Hypocalcemic Action of Parenterally Administered Calcitonin," *Endocrinol.* 115:757-761 (1984).

Gao, X. and Huang, L., "A Novel Cationic Liposome Reagent for Efficient Transfection of Mammalian Cells," *Biochem. Biophys. Res. Comm.* 179:280-285 (Aug. 1991).

Hart, S.L. et al., "Lipid-Mediated Enhancement of Transfection by a Nonviral Integrin-Targeting Vector," *Hum. Gene Ther.* 9:575-585 (Mar. 1998).

Kim, S. et al., "Preparation of Multivesicular Liposomes," *Biochim. Biophys. Acta* 728:339-348 (1983).

Mayer, L.D. et al., "Vesicles of variable sizes produced by a rapid extrusion procedure," *Biochim. Biophys. Acta* 858:161-168 (1986).

Mayhew, E. et al., "Characterization of Liposomes Prepared Using a Microemulsifier," *Biochim. Biophys. Acta* 775:169-174 (1984).

Olson, F. et al., "Preparation of Liposomes of Defined Size Distribution by Extrusion Through Polycarbonate Membranes," *Biochim. Biophys. Acta* 557:9-23 (1979).

Rosenthal, A.F. and Geyer, R.P., "A Synthetic Inhibitor of Venom Lecithinase A," *J. Biol. Chem.* 235:2202-2206 (Aug. 1960).

Szoka Jr., F. and Papahadjopoulos, D., "Procedure for preparation of liposomes with large internal aqueous space and high capture by reverse-phase evaporation," *Proc. Natl. Acad. Sci. USA* 75:4194-4198 (1978).

Zhou, X. et al., "Lipophilic polylysines mediate efficient DNA transfection in mammalian cells," *Biochim. Biophys. Acta* 1065:8-14 (1991).

Life Technologies Inc. catalogue, *Spectrum*, pp. 1-8 (Sep. 1999).

Iakobashvili, R., and Lapidot, A., "Low temperature cycled PCR protocol for Klenow fragment of DNA polymerase I in the presence of proline," *Nucleic Acids Res.* 27:1556-1568, Oxford University Press (Mar. 1999).

Innis, M.A., "PCR with 7-Deaza-2'-Deoxyguanosine Triphoshate," *PCR Protocols: A Guide to Methods and Applications*, Innis, M.A., et al., eds., Academic Press, Inc., San Diego, CA, pp. 54-59 (1990).

"Voyager™- The Power of Translocation," *Expressions* 6:6, Life Technologies, Inc. (Feb. 1999).

Dialog File 351, Accession No. 8899481, Derwent WPI English language abstract for WO 93/08132 A1 (Document A012), (1993).

Dialog File 351, Acession No. 10428036, Derwent WPI English language abstract for DE 44 11 588 C1 (Document AN14), (1995).

Dialog File 351, Acession No. 10524091, Derwent WPI English language abstract for DE 44 11 594 C1 (Document AP14), (1995).

Dialog File 351, Acession No. 10655226, Derwent WPI English language abstract for WO 96/08723 A1 (Document AL15), (1996).

Co-pending U.S. Appl. No. 09/266,935, filed Mar. 12, 1999, inventors Li et al. (Not Published).

Zhu, Z., et al., "Transformation of tobacco protoplasts with DNA entrapped in pH-sensitive liposomes," *Plant Cell, Tissue & Organ Cult.* 22:135-145, Kluwer Academic Publishers (1990).

Caplus, Acession No. 1972:461856, STNEasy Caplus English language abstract for for Hetschko, M., and Gosselck, J., "Reaktionen von sulfoniumsalzen des 1,3-dithiolans und seiner 2,2-substitutionsprodukte," *Tetrahedron Lett.* 17:1691-1692, Pergamon Press (1972) (Document AT23).

Dialog File 351, Acession No. 7672839, Derwent WPI English language abstract for EP 0 304 111 B1 (Document AN4), (1991).

Dialog File 351, Acession No. 8628544, Derwent WPI English language abstract for WO 91/04668 A1 (Document AO4), (1991).

Dialog File 351, Acession No. 8822189, Derwent WPI English language abstract for DD 290 877 A5 (Document AN5), (1991).

Dialog File 351, Acession No. 9150067, Derwent WPI English language abstract for WO 92/13570 A2 (Document AL6), (1992).

Dialog File 351, Acession No. 9417386, Derwent WPI English language abstract for WO 93/07282 A1 (Document AL7), (1993).

Dialog File 351, Acession No. 9440951, Derwent WPI English language abstract for WO 93/07283 A1 (Document AM7), (1993).

Dialog File 351, Acession No. 9483543, Derwent WPI English language abstract for EP 0 544 292 A2 (Document AO7), (1993).

Dialog File 351, Acession No. 10073779, Derwent WPI English language abstract for WO 94/23751 A1 (Document AN8), (1994).

Dialog File 351, Acession No. 10968033, Derwent WPI English language abstract for WO 96/31549 A1 (Document AO10), (1994).

Banerjee et al., (2001) "Design, Synthesis, and Transfection Biology of Novel Cationic Glycolipids for Use in Liposomal Gene Delivery," *J. Med. Chem.*, 44:4176-4185.

Office Action issued by U.S. Patent Office, mailed Apr. 25, 2006, for U.S. Appl. No. 11/040,449.

Interview Summary, mailed Jun. 21, 2006, for U.S. Appl. No. 11/040,449.

* cited by examiner

TRANSFECTION REAGENTS

This application claims the benefit, under 35 U.S.C. § 119(e), of the earlier filing date of U.S. provisional application Ser. No. 60/108,117, filed Nov. 12, 1998, the contents of which are fully incorporated by reference.

BACKGROUND OF THE INVENTION

1. Field of the Invention

The present invention relates to cationic lipids and compositions of cationic lipids having utility in lipid aggregates for delivery of macromolecules and other compounds into cells.

2. Related Art

Lipid aggregates such as liposomes have been found to be useful as agents for delivery to introduce macromolecules, such as DNA, RNA, protein, and small chemical compounds such as pharmaceuticals, to cells. In particular, lipid aggregates comprising cationic lipid components have been shown to be especially effective for delivering anionic molecules to cells. In part, the effectiveness of cationic lipids is thought to result from enhanced affinity for cells, many of which bear a net negative charge. Also in part, the net positive charge on lipid aggregates comprising a cationic lipid enables the aggregate to bind polyanions, such as nucleic acids. Lipid aggregates containing DNA are known to be effective agents for efficient transfection of target cells.

The structure of various types of lipid aggregates varies, depending on composition and method of forming the aggregate. Such aggregates include liposomes, unilamellar vesicles, multilameller vesicles, micelles and the like, having particular sizes in the nanometer to micrometer range. Methods of making lipid aggregates are by now well-known in the art. The main drawback to use of conventional phospholipid-containing liposomes for delivery is that the material to be delivered must be encapsulated and the liposome composition has a net negative charge which is not attracted to the negatively charged cell surface. By combining cationic lipid compounds with a phospholipid, positively charged vesicles and other types of lipid aggregates can bind DNA, which is negatively charged, can be taken up by target cells, and can transfect target cells. (Felgner, P. L. et al. (1987) Proc. Natl. Acad. Sci. USA 84:7413–7417; Eppstein, D. et al., U.S. Pat. No. 4,897,355.)

A well-known cationic lipid is N-[1-(2,3-dioleoyloxy)propyl]-N,N,N-trimethylammonium chloride (DOTMA). The structure of DOTMA is:

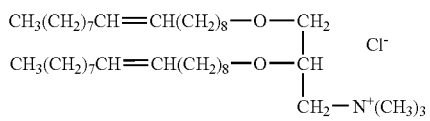

DOTMA by itself or in 1:1 combination with dioleoylphosphatidylethanolamine (DOPE) is formulated into liposomes using standard techniques. Felgner, et al. supra demonstrated that such liposomes provided efficient delivery of nucleic acids to some types of cells. A DOTMA:DOPE (1:1) formulation is sold under the trade name LIPOFECTIN (Life Technologies, Inc., Rockville, Md.). Another commercially available cationic lipid is 1,2-bis(oleoyloxy)-3-3-(trimethylammonia) propane (DOTAP), which differs from DOTMA only in that the oleoyl moieties are linked via ester, rather than ether bonds to the propylamine. A related group of compounds differ from DOTMA and DOTAP in that one of the methyl groups of the trimethylammonium group is replaced by a hydroxyethyl group. Compounds of this type are similar to the Rosenthal Inhibitor (RI) of phospholipase A (Rosenthal, A. F. and Geyer, R. P. (1960) J. Biol. Chem. 235:2202–2206) which has stearoyl esters linked to the propylamine core. The dioleoyl analogs of RI are commonly abbreviated as DORI-ether and DORI-ester, depending on the linkage of the fatty acid moieties to the propylamine core. The hydroxy group can be used as a site for further functionalization.

The dimyristyloxy analog of RI is known as DMRIE. A 1:1(M/M) DMRIE:cholesterol formulation is sold under the tradename DMRIE-C (Life Technologies, Inc., Rockville, Md.). The structure of DMRIE is:

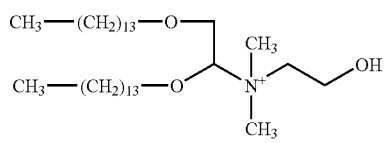

Another class of compounds has been disclosed by Behr et al. (1989) Proc. Natl. Acad. Sci. USA 86:6982–6986; EPO publication 0 394 111 (Oct. 24, 1990), in which carboxyspermine has been conjugated to two types of lipids. The structures of 5-carboxyspermylglycine dioctadecylamide (DOGS) is:

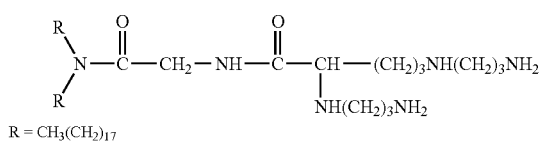

The structure of dipalmitoylphosphatidylethanolamine 5-carboxyspermylamide (DPPES) is:

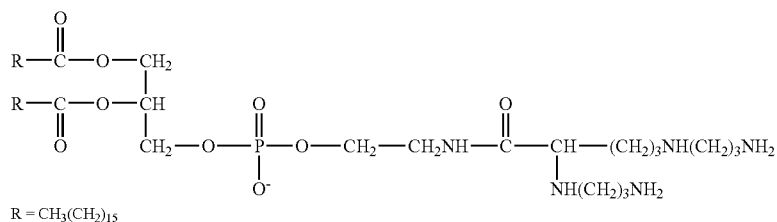

Both DOGS and DPPES have been used to coat plasmids, forming a lipid aggregate complex that provides efficient transfection. The compounds are claimed to be more efficient and less toxic than DOTMA for transfection of some cell lines. DOGS is available commercially as TRANS-FECTAM™ (Promega, Madison, Wis.).

Another class of compounds has been also described in which carboxy spermine has been conjugated to lipids via an amide bond (Gebeyehu, G. et al., U.S. Pat. No. 5,334,761). These compounds are useful for an efficient delivery of nucleic acids into various cells and also are intermediates for making other such lipids. 2,3-di-oleyloxy-N-[2(sperminecarboxamido)ethyl]-N,N-dimethyl-1-propan-aminium (DOSPA) is available as a 3:1 (w/w) formulation with DOPE under the trade name LipofectAMINE (available from Life Technologies, Inc., Rockville, Md.). The structure of DOSPA is as follows:

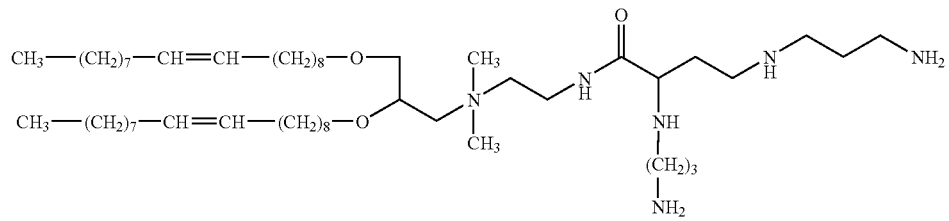

Lipid compounds with a spermine head group have also been described (Haces, A., et al., U.S. Pat. No. 5,674,908). These compounds are especially useful for delivery of nucleic acids into insect cells. A 1:1.5 (M/M) formulation of tetramethyltetrapalmityl spermine (TM-TPS) to DOPE is commercially available under the tradename CellFECTIN (Life Technologies, Inc., Rockville, Md.). The structure of TM-TPS is shown below:

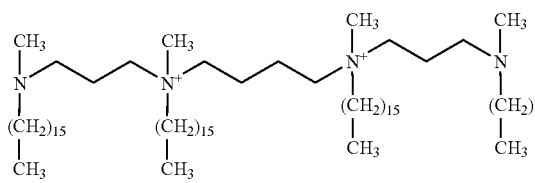

A cationic cholesterol derivative (DC-Chol) has been synthesized and formulated into liposomes in combination with DOPE. (Gao. X. and Huang, L. (1991) Biochim. Biophys. Res. Comm. 179:280–285). The compound's structure is:

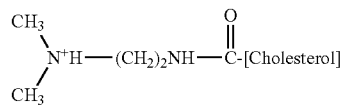

Liposomes formulated with DC-Chol are said to provide more efficient transfection and lower toxicity than DOTMA-containing liposomes for some cell lines.

Lipopolylysine, formed by conjugating polylysine to DOPE, has been reported to be especially effective for transfection in the presence of serum, a condition likely to be encountered in vivo (Zhou, X. et al. (1991) Biochim. Biophys. Acta 1065: 8–14).

Despite advances in the field, a need remains for a variety of improved cationic lipid compounds. In particular, no single cationic lipid to date has been found to work well with all cell types. Since different cell types differ from one another in membrane composition, it is not surprising that different compositions and types of lipid aggregates are effective for different cell types, either for their ability to contact and fuse with target cell membranes, or for aspects of the transfer process itself. At present these processes are not well understood, consequently the design of effective liposomal precursors is largely empirical. Besides content and transfer, other factors are of importance, for example, ability to form lipid aggregates suited to the intended purpose, the possibility of transfecting cells in the presence of serum, toxicity to the target cell, stability as a carrier for the compound to be delivered, and ability to function in an in vivo environment. In addition, lipid aggregates can be improved by broadening the range of substances which can be delivered to cells. The cationic lipid compounds of the present invention have improved function with respect to several of the foregoing attributes.

SUMMARY OF THE INVENTION

The present invention provides novel cationic lipids according to the general Formula (A):

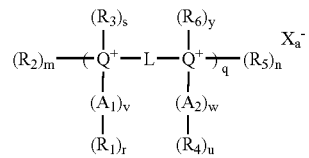

wherein

Q is selected from the group consisting of N, O and S;

L is any bivalent organic radical capable of covalently linking each Q, such as C, CH, $(CH_2)_1$, or $\{(CH_2)_i—Y—(CH_2)_j\}_k$, wherein Y is selected from the group consisting of $CH_2$, an ether, a polyether, an amide, a polyamide, an ester, a sulfide, a urea, a thiourea, a guanidyl, a carbamoyl, a carbonate, a phosphate, a sulfate, a sulfoxide, an imine, a carbonyl, and a secondary amino group and wherein Y is optionally substituted by $—X_1—L'—X_2—Z$ or $—Z$;

$R_1$–$R_6$, independently of one another, are selected from the group consisting of H, $—(CH_2)_p—D—Z$, an alkyl, an alkenyl, an aryl, and an alkyl or alkyl ether optionally substituted by one or more of an alcohol, an aminoalcohol, an amine, an amide, an ether, a polyether, a polyamide, an ester, a mercaptan, an alkylthio, a urea, a thiourea, a guanidyl, or a carbamoyl group, and wherein at least one of $R_1$, $R_3$, $R_4$ and $R_6$ is a straight chain or branched, cyclic, alkyl, alkenyl, alkynyl or aryl group; and any one or more of $R_1$, $R_3$, $R_4$ and $R_6$ may optionally be covalently linked with each other, with Y or with L when L is C or CH to form a cyclic moiety;

Z is selected from the group consisting of amine, spermiyl, carboxyspermiyl, guanidyl, spermidinyl, putricinyl, diaminoalkyl, pyridyl, piperidinyl, pyrrolidinyl, polyamine, amino acid, peptide, and protein;

$X_1$ and $X_2$, independently of one another, are selected from the group consisting of NH, O, S, alkylene, and arylene;

L' is selected from the group consisting of alkylene, alkenylene, alkynylene, arylene, alkylene ether, and polyether;

D is Q or a bond;

$A_1$ and $A_2$, independently of one another, are selected from the group consisting of $CH_2O$, $CH_2S$, $CH_2NH$, $C(O)$, $C(NH)$, $C(S)$ and $(CH_2)_t$;

X is a physiologically acceptable anion;

m, n, r, s, u, v, w and y are 0 or 1, with the proviso that when both m and n are 0 at least one of r, s, u and y is other than 0;

i, j, k, l, p and t are from 0 to about 100;

q is an integer from 1 to about 1000; and a is the number of positive charge divided by the valence of the anion. Further, the present invention provides novel cationic lipids according to the general Formula (B):

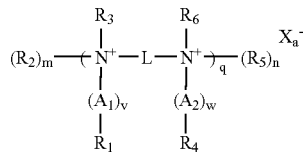

wherein

L is $(CH_2)$, or $\{(CH_2)_i-Y-(CH_2)_j\}_k$ wherein Y is selected from the group consisting of an ether, a polyether, an amide, a polyamide, an ester, a sulfide, a urea, a thiourea, a guanidyl, a carbamoyl, a carbonate, and a secondary amino group;

$R_1$–$R_6$, independently of one another, are selected from the group consisting of H, $—(CH_2)_p—Z$, an alkyl, an alkenyl, an aryl, and an alkyl or an alkyl ether optionally substituted by one or more of an alcohol, an aminoalcohol, an amine, an amide, an ether, a polyether, a polyamide, an ester, a mercaptan, a urea, a thiourea, a guanidyl, or a carbamoyl group, and at least one of $R_1$, $R_3$, $R_4$ and $R_6$ is a straight chain or branched, cyclic, alkyl, alkenyl, alkynyl or aryl group, preferably having from about 2 to 100, preferably 4 to 75, more preferably 6 to 64, more preferably 8 to 50, more preferably 8 to 40, more preferably 8 to 30, more preferably 6 to 30, more preferably 4 to 30, more preferably 2 to 30, and most preferably 8 to about 24 carbon atoms, and any one or more of $R_1$, $R_3$, $R_4$ and/or $R_6$ may optionally be covalently linked with each other to form a cyclic moiety;

Z is selected from the group consisting of amine, spermiyl, carboxyspermiyl, guanidyl, spermidinyl, putricinyl, diaminoalkyl, pyridyl, piperidinyl, pyrrolidinyl, polyamine, amino acid, amino acid derivative, peptide, and protein;

$A_1$ and $A_2$, independently of one another, are selected from the group consisting of $CH_2O$, $CH_2S$, $CH_2NH$, $C(O)$, $C(NH)$, $C(S)$ and $(CH_2)_t$;

X is a physiologically acceptable anion, such as the halide anions, chloride, bromide, and iodide as well as acetate, sulfate, trifluoroacetate, etc.;

m, n, v and w are 0 or 1;

i, j, k, l, p and t are integers from 1 to about 100, more preferably 1 to 50, more preferably 1 to 25, more preferably 1 to 15, more preferably 1 to 10 and most preferably 1 to about 4;

q is an integer from 1 to about 1000, preferably from 1 to about 500, more preferably from 1 to about 250, more preferably from 1 to about 100, more preferably from 1 to about 50, more preferably from 1 to about 25, more preferably from 1 to about 12, most preferably from 1 to about 6; and a is the number of positive charges divided by the valence of the anion, wherein when m and n are 0, then a is 0.

Also, the present invention provides novel cationic lipids according to the Formula (C):

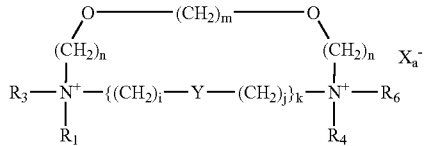

wherein

Y is selected from the group consisting of $CH_2$, an ether, a polyether, an amide, a polyamide, an ester, a sulfide, a urea, a thiourea, a guanidyl, a carbamoyl, a carbonate, a phosphate, a sulfate, a sulfoxide, an imine, a carbonyl, and a secondary amino group and wherein Y is optionally substituted by $—X_1—L'—X_2—Z$ or $—Z$;

$R_1$, $R_3$, $R_4$ and $R_6$, independently of one another, are selected from the group consisting of H, $—(CH_2)_p—D—Z$, an alkyl, an alkenyl, an aryl, and an alkyl or an alkyl ether optionally substituted by one or more of an alcohol, an aminoalcohol, an amine, an amide, an ether, a polyether, a polyamide, an ester, a mercaptan, an alkylthio, a urea, a thiourea, a guanidyl, or a carbamoyl group, and at least one of $R_1$, $R_3$, $R_4$ and $R_6$ is a straight chain or branched, cyclic, alkyl, alkenyl, alkynyl or aryl group, most preferably having from about 8 to about 24 carbon atoms, and $R_1$, $R_3$, $R_4$ and $R_6$ may optionally be covalently linked with each other or with Y, to form a cyclic moiety;

Z is selected from the group consisting of amine, spermiyl, caboxyspermiyl, guanidyl, spermidinyl, putricinyl, diaminoalkyl, pyridyl, piperidinyl, pyrrolidinyl, polyamine, amino acid, peptide, and protein;

$X_1$ and $X_2$, independently of one another, are selected from the group consisting of NH, O, S, alkylene, and arylene;

L' is selected from the group consisting of alkylene, alkenylene, alkynylene, arylene, alkylene ether, and polyether;

D is Q or a bond;

m and n are 0 or 1; and i, j, k, l and p are integers from 1 to about 10.

Further, the present invention provides compounds or polycations according to the Formula (D):

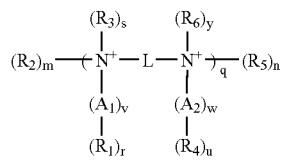

wherein

L is C, CH, $(CH_2)_l$, or $\{(CH_2)_i-Y-(CH_2)_j\}_k$, wherein Y is selected from the group consisting of $CH_2$, an ether, a polyether, an amide, a polyamide, an ester, a sulfide, a urea, a thiourea, a guanidyl, a carbamoyl, a carbonate, a phosphate, a sulfate, a sulfoxide, an imine, a carbonyl, and a secondary amino group and wherein Y is optionally substituted by $-X_1-L'-X_2-Z$ or $-Z$;

$R_1-R_6$, independently of one another, are selected from the group consisting of H, $-(CH_2)_p-D-Z$, an alkyl, an alkenyl, an aryl, and an alkyl or an alkyl ether optionally substituted by one or more of an alcohol, an aminoalcohol, an amine, an amide, an ether, a polyether, a polyamide, an ester, a mercaptan, an alkylthio, a urea, a thiourea, a guanidyl, or a carbamoyl group, and wherein at least one of $R_1$, $R_3$, $R_4$ and $R_6$ is a straight chain or branched, cyclic, alkyl, alkenyl, alkynyl or aryl groups, preferably having from about 2 to about 30 carbon atoms, more preferably from 8 to 24 carbon atoms;

Z is selected from the group consisting of amine, spermiyl, carboxyspermiyl, guanidyl, spermidinyl, putricinyl, diaminoalkyl, pyridyl, piperidinyl, pyrrolidinyl, polyamine, amino acid, amino acid derivative, peptide, and protein;

$X_1$ and $X_2$, independently of one another, are selected from the group consisting of NH, O, S, alkylene and arylene;

L' is selected from the group consisting of alkylene, alkenylene, alkynylene, arylene, alkylene ether, and polyether;

$A_1$ and $A_2$, independently of one another, are selected from the group consisting of $CH_2O$, $CH_2S$, $CH_2NH$, C(O), C(NH), C(S) and $(CH_2)_t$;

m, n, r, s, u, v, w and y are 0 or 1, with the proviso that when both m and n are 0 at least one of r, s, u and y is other than 0;

i, j, k, l, p and t are integers from 0 to about 100; and q is an integer from 1 to about 1000.

Also, the present invention provides compounds or polycations according to the Formula (E):

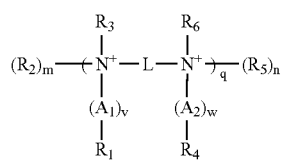

wherein

L is $(CH_2)_l$ or $\{(CH_2)_i-Y-(CH_2)_j\}_k$, wherein Y is selected from the group consisting of $CH_2$, an ether, a polyether, an amide, a polyamide, an ester, a sulfide, a urea, a thiourea, a guanidyl, a carbamoyl, a carbonate, and a secondary amino group;

$R_1-R_6$, independently of one another, are selected from the group consisting of H, $-(CH_2)_p-Z$, an alkyl, an alkenyl, an aryl, and an alkyl or an alkyl ether optionally substituted by one or more of an alcohol, an aminoalcohol, an amine, an amide, an ether, a polyether, a polyamide, an ester, a mercaptan, a urea, a thiourea, a guanidyl, or a carbamoyl group, and at least one of $R_1$, $R_3$, $R_4$ and $R_6$ is a straight chain or branched, cyclic, alkyl, alkenyl, alkenyl or aryl group, preferably having from about 2 to about 30 carbon atoms, more preferably having from about 8 to about 24 carbon atoms;

Z is selected from the group consisting of amine, spermiyl, carboxyspermiyl, guanidyl, spermidinyl, putricinyl, diaminoalkyl, pyridyl, piperidinyl, pyrrolidinyl, polyamine, amino acid, amino acid derivative, peptide, and protein;

$A_1$ and $A_2$, independently of one another, are selected from the group consisting of $CH_2O$, $CH_2S$, $CH_2NH$, C(O), C(NH), C(S) and $(CH_2)_t$;

m, n, v and w are 0 or 1;

i, j, k, l, p and t are integers from 1 to about 100; and q is an integer from 1 to about 1000.

Also, the present invention provides novel compounds falling within the scope of the above formulae.

The compounds of the invention are useful, either alone or in combination with other lipid aggregate-forming components (e.g., DOPE, DOPC or cholesterol) for formulation into liposomes or other lipid aggregates. Such aggregates are polycationic, able to form stable complexes with anionic macromolecules, such as nucleic acids. The lipid aggregate macromolecular complex interacts with cells making the polyanionic macromolecule available for absorption and uptake by the cell.

The present invention provides a lipid aggregate comprising one or more of the compounds of the present invention. Preferably, the lipid aggregate comprises at least one lipid aggregate-forming compound. Preferably, the lipid aggregate-forming compound is selected from the group consisting of DOPE, DOPC and cholesterol.

The compounds of the present invention may also be conjugated to or mixed with or used in conjunction with a variety of useful molecules and substances such as proteins, peptides, growth factors and the like to enhance cell-targeting, uptake, internalization, nuclear targeting and expression.

This invention also includes lipid aggregates comprising one or more compounds of the present invention or mixtures thereof. Such lipid aggregates may be combined with one or more aggregate-forming components and/or transfection enhancers.

The transfection methods of the present invention employing the compounds or compositions (such as those described above) of the present invention or mixtures thereof can be applied to in vitro and in vivo transfection of cells, particularly to transfection of eukaryotic cells or tissues including animal cells, human cells, insect cells, plant cells, avian cells, fish cells, mammalian cells and the like.

Accordingly, the present invention provides a method for introducing a polyanion into a cell or cells, wherein the method comprises forming a liposome from a positively charged compound according to the invention, contacting the liposome with polyanion to form a positively-charged polyanion-liposome complex and incubating the complex with a cell or cells.

The methods of this invention can be used to generate transfected cells or tissues which express useful gene products. The methods of this invention can also be used as a step in the production of transgenic animals. The methods of this invention are useful in any therapeutic method requiring introducing of nucleic acids into cells or tissues. In particular, these methods are useful in cancer treatment, in in vivo and ex vivo gene therapy, and in diagnostic methods. See, for example, U.S. Pat. No. 5,589,466 to Felgner, et al. and U.S. patent application Ser. No. 08/450,555 filed on May 25, 1995 to Jessee, et al. The transfection compounds or compositions of this invention can be employed as research reagents in any transfection of cells or tissues done for research purposes. Nucleic acids that can be transfected by the methods of this invention include DNA and RNA from any source comprising natural bases or non-natural bases, and include those encoding and capable of expressing therapeutic or otherwise useful proteins in cells or tissues, those which inhibit expression of nucleic acids in cells or tissues, those which inhibit enzymatic activity or activate enzymes, those which catalyze reactions (ribozymes), and those which function in diagnostic assays.

The compounds, compositions and methods provided herein can also be readily adapted in view of the disclosure herein to introduce biologically active macromolecules or subtances other than nucleic acids, including, among others, polyamines, polyamine acids, polypeptides, proteins, biotin, and polysaccharides into cells. Other useful materials for example, therapeutic agents, diagnostic materials and research reagents, can be introduced into cells by the methods of this invention. In a preferred aspect, any nucleic acid vector may be delivered to or into a cell by the present invention.

Accordingly, the present invention provides a method for introducing a biologically active substance into a cell, wherein the method comprises forming a liposome of a compound according to the invention and a biologically active substance and incubating the liposome with a cell or cell culture.

The invention also relates to compositions comprising the compounds of the invention and one or more additional components selected from the group consisting of nucleic acids, cells, buffers, culture media, biologically active substance, neutral lipids, and transfection enhancers, preferably a nucleic acid.

This invention also includes transfection kits which include one or more of the compounds or compositions of the present invention or mixtures thereof. Particularly, the invention provides a kit comprising one or more of the compounds of the present invention and at least one additional component selected from the group consisting of a cell, cells, a cell culture media, a nucleic acid, a transfection enhancer and instructions fro transfecting a cell or cells.

The invention also relates to intermediates and methods for using such intermediates for making the compounds or compositions of the invention. The invention also relates to the compositions, compounds or components obtained by the interaction of materials (intermediates, compounds, lipids etc.) used in the synthesis methods of the invention.

Other preferred embodiments of the present invention will be apparent to one of ordinary skill in the art in view of the following drawings and description of the invention.

DETAILED DESCRIPTION OF THE PREFERRED EMBODIMENTS

Figure 1:
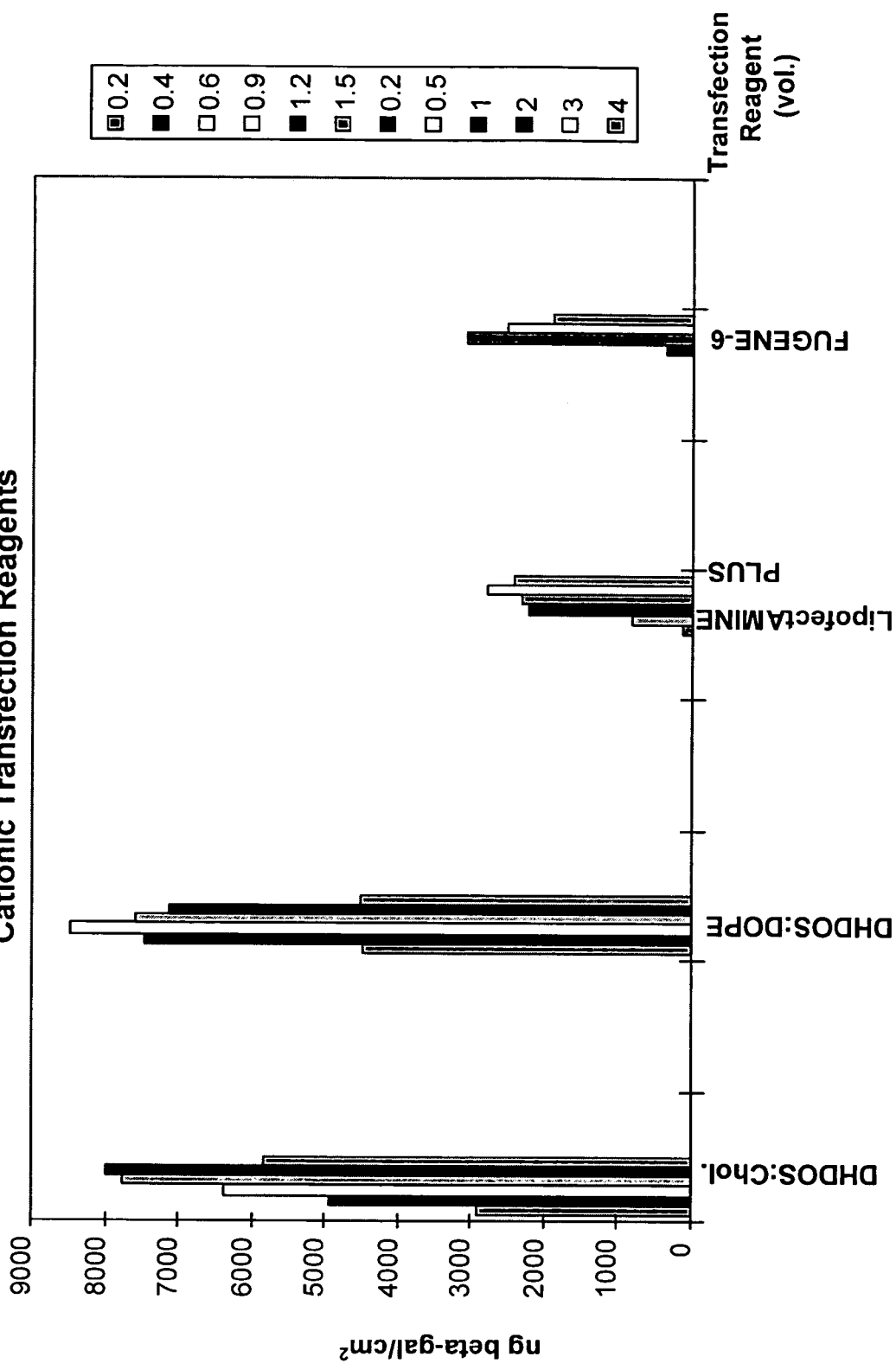
FIG. 1 is a graph showing the transfection of HEK-293 cells with cationic transfection reagents.

The present invention relates to cationic lipids and compositions of cationic lipids having utility in lipid aggregates for delivery of macromolecules and other compounds into cells. The compounds can be used alone or in combination with other compounds to prepare liposomes and other lipid aggregates suitable for transfection or delivery of compounds to target cells, either in vitro or in vivo.

The compounds of the present invention are preferably polycationic and preferably thus form highly stable complexes with various anionic macromolecules, particularly polyanions such as nucleic acids. These compounds have the property, when dispersed in water, of forming lipid aggregates which associate strongly, via their cationic portion, with polyanions. By using an excess of cationic charges relative to the anionic compound, the polyanion-lipid complexes may be adsorbed on cell membranes, thereby facilitating uptake of the desired compound by the cells.

The present invention also relates to intermediates for preparing the compound and compositions of the invention.

More specifically, the present invention relates to a cationic lipid for transfection which has a greater transfection efficiency than commercially available products in the three most common cell types used in expression research (CHO-K1, COS-7, and HEK293) making it useful for high throughput applications; and which has a simple to use protocol as defined by the fact that no additional reagents are required (e.g., such as LipofectAMINE PLUS Reagent available from Life Technologies, Inc., Rockville, Md.), no removal of serum and therefore no media changes are required, and the DNA/lipid complex do not need to be removed from the cells prior to assay.

The compounds according to the present invention have the Formula (A):

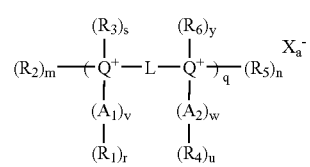

wherein

Q is selected from the group consisting of N, O and S;

L is any bivalent organic radical capable of covalently linking each Q, such as C, CH, $(CH_2)_1$, or $\{(CH_2)_i\text{—}Y\text{—}(CH_2)_j\}_k$, wherein Y is selected from the group consisting of $CH_2$, an ether, a polyether, an amide, a polyamide, an ester, a sulfide, a urea, a thiourea, a guanidyl, a carbamoyl, a carbonate, a phosphate, a sulfate, a sulfoxide, an imine, a carbonyl, and a secondary amino group and wherein Y is optionally substituted by —X$_1$—L'—X$_2$—Z or —Z;

R$_1$–R$_6$, independently of one another, are selected from the group consisting of H, —(CH$_2$)$_p$—D—Z, an alkyl, an alkenyl, an aryl, and an alkyl or alkyl ether optionally substituted by one or more of an alcohol, an aminoalcohol, an amine, an amide, an ether, a polyether, a polyamide, an ester, a mercaptan, an alkylthio, a urea, a thiourea, a guanidyl, or a carbamoyl group, and wherein at least one of R$_1$, R$_3$, R$_4$ and R$_6$ is a straight chain or branched, cyclic, alkyl, alkenyl, alkynyl or aryl group; and R, and R$_4$ or R$_3$ and R$_6$ may optionally be covalently linked with each other, with Y or with L when L is C or CH to form a cyclic moiety;

Z is selected from the group consisting of amine, spermiyl, carboxyspermiyl, guanidyl, spermidinyl, putricinyl, diaminoalkyl, pyridyl, piperidinyl, pyrrolidinyl, polyamine, amino acid, peptide, and protein;

X$_1$ and X$_2$, independently of one another, are selected from the group consisting of NH, O, S, alkylene, and arylene;

L' is selected from the group consisting of alkylene, alkenylene, alkynylene, arylene, alkylene ether, and polyether;

D is Q or a bond;

A$_1$ and A$_2$, independently of one another, are selected from the group consisting of CH$_2$O, CH$_2$S, CH$_2$N—H, C(O), C(NH), C(S) and (CH$_2$)$_t$;

X is a physiologically acceptable anion;

m, n, r, s, u, v, w and y are 0 or 1, with the proviso that when both m and n are 0 at least one of r, s, u and y is other than 0;

i, j, k, l, p and t are integers from 0 to about 100;

q is an integer from 1 to about 1000; and a is the number of positive charge divided by the valence of the anion.

Preferably the alkyl ether optionally substituted by one or more alcohol groups comprises a carbohydrate. Preferably, the carbohydrate is selected from the group consisting of galactose, fructose, glucose, maltose, sucrose, cellobiose, lactose, mannose, glucopyranose, mannopyranose and galactopyranose.

Preferably, i, j, k, l, p and t are integers independently selected from 1 to 100, more preferably from 1 to 50, more preferably 1 to 25, more preferably 1 to 15, more preferably 1 to 10 and most preferably 1 to about 4. Preferably, l, b and c are integers from 1 to about 4, i and j are integers from about 2 to about 3 and k is an integer from 1 to about 3.

Preferably, q is an integer from 1 to about 500, more preferably from 1 to about 250, more preferably from 1 to about 100, more preferably from 1 to about 50, more preferably from 1 to about 25, more preferably from 1 to about 12, most preferably from 1 to about 6.

Preferably, at least one of R$_1$, R$_3$, R$_4$ and R$_6$ is a straight chain or branched, cyclic, alkyl, alkenyl, alkynyl or aryl group having from about 2 to 100, preferably 4 to 75, more preferably 6 to 64, more preferably 8 to 50, more preferably 8 to 40, more preferably 8 to 30, more preferably 6 to 30, more preferably 4 to 30, and most preferably 8 to about 24 carbon atoms.

In all aspects of the invention, most suitable R$_1$ and R$_4$ groups, which can be the same or different, preferably the same, are C$_{6-30}$ hydracarbon radicals derived from fatty acids or activated derivatives thereof, such as fatty acyl chlorides. Thus, typical R$_1$ and R$_4$ groups are C$_{6-30}$ alkyl or alkenyl groups.

Preferably, R$_1$, R$_2$, R$_3$, R$_4$, R$_5$, and R$_6$, independently of one another, are selected from the group consisting of H, C$_1$–C$_8$ alkyl, alkenyl, aryl, and alkyl optionally substituted by one or more of an alcohol, an amide, an ether, a polyether, a polyamide, an ester, a mercaptan, a urea, a thiourea, a guanidyl, or a carbamoyl group, and at least one of R$_1$, R$_3$, R$_4$ and R$_6$ is a straight chain or branched, cyclic, alkyl, alkenyl, alkynyl or aryl group having from about 8 to about 24 carbon atoms.

Preferably Q is N.

Preferably, Y is selected from the group consisting of CH$_2$, O S and NH.

Useful compounds falling within the scope of the above formula (A) include compounds having the following formulae:

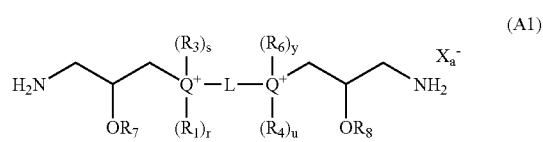

(A1)

wherein

Q and L are as defined above;

R$_1$, R$_3$, R$_4$ and R$_6$, independently of one another, are selected from the group consisting of H and a C$_1$–C$_8$ alkyl, alkenyl, aryl, and alkyl optionally substituted by one or more of an alcohol, an amine, an amide, an ether, a polyether, a polyamide, an ester, a mercaptan, a urea, a thiourea, a guanidyl, or a carbamoyl group;

r, s, u and y are 0 or 1; and

R$_7$ and R$_8$ are independently H or a carbohydrate;

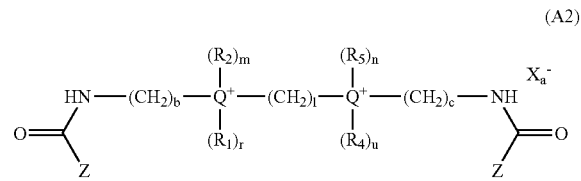

(A2)

wherein

Q is as defined above;

R$_1$, R$_2$, R$_4$ and R$_5$, independently of one another, are selected from the group consisting of H and a C$_1$–C$_8$ alkyl, alkenyl, aryl, and alkyl optionally substituted by one or more of an alcohol, an amine, an amide, an ether, a polyether, a polyamide, an ester, a mercaptan, a urea, a thiourea, a guanidyl, or a carbamoyl group;

Z is selected from the group consisting of spermiyl, spermidiyl, amino acid, peptidyl, diaminoalkyl, and polyamine;

m, n, r and u are 0 or 1; and l, b and c are integers independently selected from 1 to about 4;

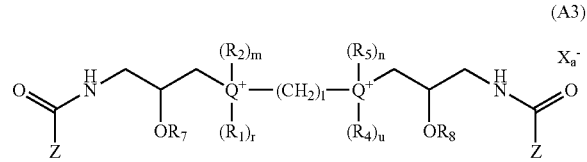

(A3)

wherein
Q, $R_1$, $R_4$, m, n, r and u are as defined above;
$R_2$ and $R_5$, independently of one another, are selected from the group consisting of H and a $C_1$–$C_8$ alkyl, alkenyl, aryl, and alkyl optionally substituted by one or more of an alcohol, an amine, an amide, an ether, a polyether, a polyamide, an ester, a mercaptan, a urea, a thiourea, a guanidyl, or a carbamoyl group;
Z is selected from the group consisting of spermiyl, spermidiyl, amino acid, peptidyl, diaminoalkyl, and polyamine;
$R_7$ and $R_8$ are independently H or a carbohydrate; and
l is an integer from 1 to about 4;

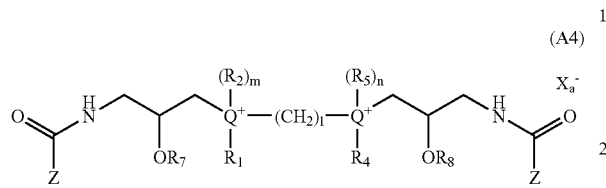

(A4)

wherein
Q is as defined above, preferably N;
at least one of $R_1$ and $R_4$ are straight chain or branched, cyclic, alkyl, alkenyl, alkynyl or aryl groups having from about 8 to about 24 carbon atoms;
$R_2$ and $R_5$, independently of one another, are selected from the group consisting of H and a $C_1$–$C_8$ alkyl, alkenyl, aryl, and alkyl optionally substituted by one or more of an alcohol, an amine, an amide, an ether, a polyether, a polyamide, an ester, a mercaptan, a urea, a thiourea, a guanidyl, or a carbamoyl group;
Z is selected from the group consisting of spermiyl, spermidiyl, amino acid, peptidyl, diaminoalkyl, and polyamine;
$R_7$ and $R_8$ are independently H or a carbohydrate, preferably H; m and n are as defined above; and
l is an integer from 1 to about 4;

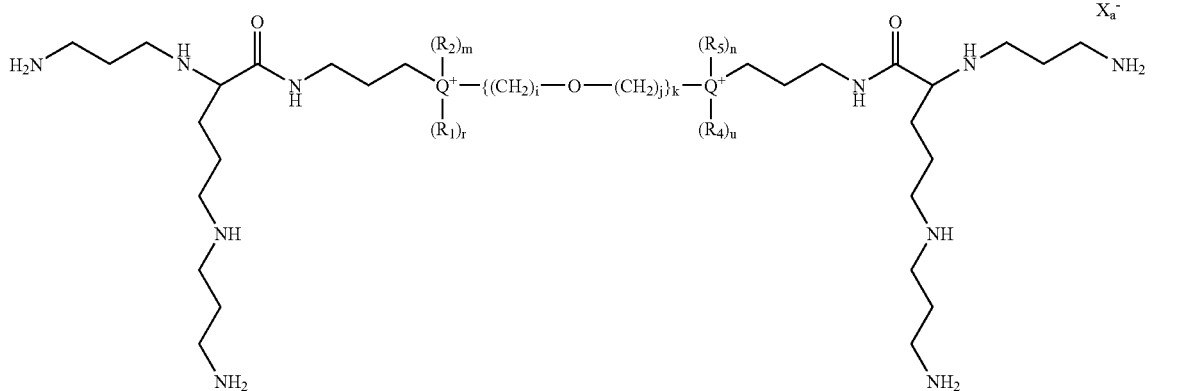

(A5)

wherein
Q, $R_1$, $R_4$, r, u, m and n are as defined above;
$R_2$ and $R_5$, independently of one another, are selected from the group consisting of H and a $C_1$–$C_8$ alkyl, alkenyl, aryl, and alkyl optionally substituted by one or more of an alcohol, an amine, an amide, an ether, a polyether, a polyamide, an ester, a mercaptan, a urea, a thiourea, a guanidyl, or a carbamoyl group;
i and j are integers from about 2 to about 3; and
k is an integer from 1 to about 3;

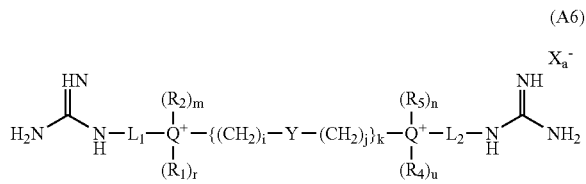

(A6)

wherein
Q, $R_1$, $R_4$, r, u, m and n are as defined above;
$R_2$ and $R_5$, independently of one another, are selected from the group consisting of H and a $C_1$–$C_8$ alkyl, alkenyl, aryl, and alkyl optionally substituted by one or more of an alcohol, an amine, an amide, an ether, a polyether, a polyamide, an ester, a mercaptan, a urea, a thiourea, a guanidyl, or a carbamoyl group;
i and j are integers from about 2 to about 3;
k is an integer from 1 to about 3;
$L_1$, and $L_2$, independently from one another, are an alkylene or an alkylene ether; and
Y is selected from the group consisting of $CH_2$, O, S and NH;

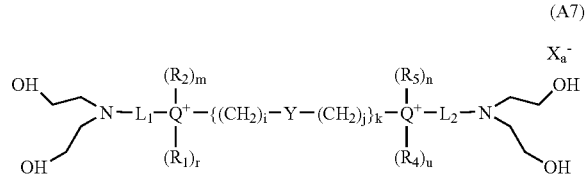

(A7)

polyether, a polyamide, an ester, a mercaptan, a urea, a thiourea, a guanidyl, or a carbamoyl group;

i and j are integers from about 2 to about 3;

k is an integer from 1 to about 3;

$L_1$ and $L_2$, independently from one another, are an alkylene or an alkylene ether; and Y is selected from the group consisting of $CH_2$, O, S and NH;

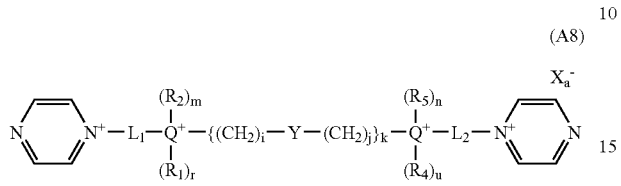

(A8)

wherein

Q, $R_1$, $R_4$, r, u, m and n are as defined above;

$R_2$ and $R_5$, independently of one another, are selected from the group consisting of H and a $C_1$–$C_8$ alkyl, alkenyl, aryl, and alkyl optionally substituted by one or more of an alcohol, an amine, an amide, an ether, a polyether, a polyamide, an ester, a mercaptan, a urea, a thiourea, a guanidyl, or a carbamoyl group;

i and j are integers from about 2 to about 3;

k is an integer from 1 to about 3;

$L_1$ and $L_2$, independently from one another, are an alkylene or an alkylene ether; and Y is selected from the group consisting of $CH_2$, O, S and NH;

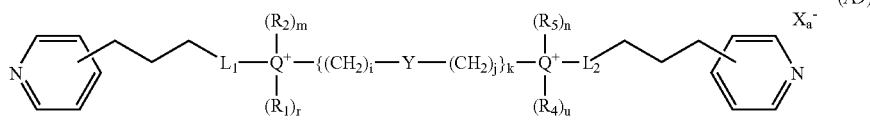

(A9)

wherein

Q, $R_1$, $R_2$, r, u, m and n are as defined above;

$R_2$ and $R_5$, independently of one another, are selected from the group consisting of H and a $C_1$–$C_8$ alkyl, alkenyl, aryl, and alkyl optionally substituted by one or more of an alcohol, an amine, an amide, an ether, a polyether, a polyamide, an ester, a mercaptan, a urea, a thiourea, a guanidyl, or a carbamoyl group;

i and j are integers from about 2 to about 3;

k is an integer from 1 to about 3;

$L_1$ and $L_2$, independently from one another, are an alkylene or an alkylene ether; and Y is selected from the group consisting of $CH_2$, O, S and NH; and wherein Q, $R_1$, $R_4$, r, u, m, and n are as defined above;

$R_2$ and $R_5$, independently of one another, are selected from the group consisting of H and a $C_1$–$C_8$ alkyl, alkenyl, aryl, and alkyl optionally substituted by one or more of an alcohol, an amine, an amide, an ether, a polyether, a polyamide, an ester, a mercaptan, a urea, a thiourea, a guanidyl, or a carbamoyl group;

i and j are integers from about 2 to about 3;

k is an integer from 1 to about 3;

$L_1$ and $L_2$, independently from one another, are an alkylene or an alkylene ether; and Y is selected from the group consisting of $CH_2$, O, S and NH.

Also, compounds of the present invention have the Formula (B):

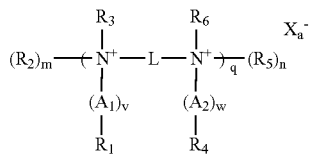

wherein

L is $(CH_2)_1$ or $\{(CH_2)_i —Y— (CH_2)_j\}_k$, wherein Y is selected from the group consisting of $CH_2$, an ether, a polyether, an amide, a polyamide, an ester, a sulfide, a urea, a thiourea, a guanidyl, a carbamoyl, a carbonate, and a secondary amino group;

$R_1$–$R_6$, independently of one another, are selected from the group consisting of H, —$CH_2)_p$—Z, an alkyl, an alkenyl, an aryl, and an alkyl or alkyl ether optionally substituted by one or more of an alcohol, an aminoalcohol, an amine, an amide, an ether, a polyether, a polyamide, an ester, a mercaptan, a urea, a thiourea, a guanidyl, or a carbamoyl group, and at least one of $R_1$, $R_3$, $R_4$ and $R_6$ is a straight chain or branched, cyclic, alkyl, alkenyl, alkenyl or aryl group, and any one or more of $R_1$, $R_4$, $R_3$ and $R_6$ may optionally be covalently linked with each other to form a cyclic moiety;

Z is selected from the group consisting of amine, spermiyl, carboxyspermiyl, guanidyl, spermidinyl, putrici-

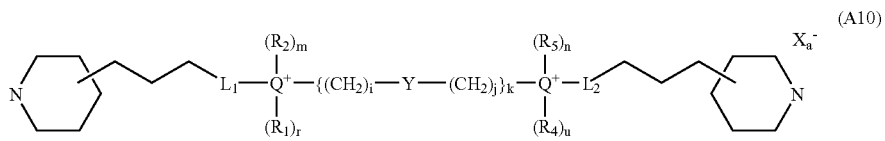

(A10)

nyl, diaminoalkyl, pyridyl, piperidinyl, pyrrolidinyl, polyamine, amino acid, peptide, and protein;

$A_1$ and $A_2$, independently of one another, are selected from the group consisting of $CH_2O$, $CH_2S$, $CH_2NH$, $C(O)$, $C(NH)$, $C(S)$ and $(CH_2)_t$;

X is a physiologically acceptable anion;

m, n, v and w are 0 or 1;

i, j, k, l, p and t are integers from 1 to about 100;

q is an integer from 1 to about 1000; and a is the number of positive charge divided by the valence of the anion, wherein when m and n are 0, then a is 0.

Preferably, $R_1$–$R_6$, i, j, k, l, p, t, q, b and c are as defined with reference to Formula (A).

Preferably, Y is selected from the group consisting of $CH_2$, O, S and NH.

Useful compounds falling within the scope of the Formula (B) include compounds having the following formulae:

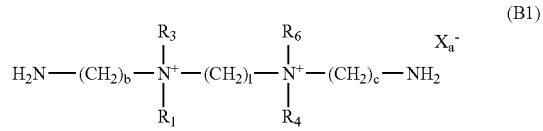

(B1)

wherein $R_1$, $R_3$, $R_4$ and $R_6$, independently of one another, are selected from the group consisting of H and a $C_1$–$C_8$ alkyl, alkenyl, aryl, and alkyl optionally substituted by one or more of an alcohol, an amine, an amide, an ether, a polyether, a polyamide, an ester, a mercaptan, a urea, a thiourea, a guanidyl, or a carbamoyl group, and at least one of $R_1$, $R_3$, $R_4$ and $R_6$ is a straight chain or branched, cyclic, alkyl, alkenyl, alkynyl or aryl group having from about 8 to about 24 carbon atoms; and l, b and c are integers independently selected from 1 to about 4;

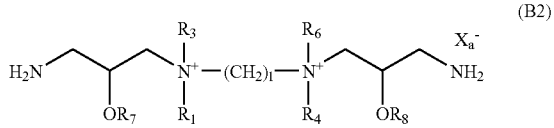

(B2)

wherein $R_1$, $R_3$, $R_4$ and $R_6$, independently of one another, are selected from the group consisting of H and a $C_1$–$C_8$ alkyl, alkenyl, aryl, and alkyl optionally substituted by one or more of an alcohol, an amine, an amide, an ether, a polyether, a polyamide, an ester, a mercaptan, a urea, a thiourea, a guanidyl, or a carbamoyl group, and at least one of $R_1$, $R_3$, $R_4$ and $R_6$ is a straight chain or branched, cyclic, alkyl, alkenyl, alkynyl or aryl group having from about 8 to about 24 carbon atoms;

$R_7$ and $R_8$ are independently H or a carbohydrate; and l is an integer from 1 to about 4;

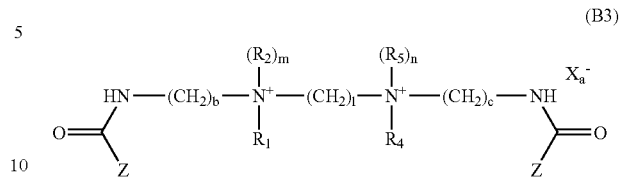

(B3)

wherein $R_1$, $R_2$, $R_4$ and $R_5$, independently of one another, are selected from the group consisting of H and a $C_1$–$C_8$ alkyl, alkenyl, aryl, and alkyl optionally substituted by one or more of an alcohol, an amine, an amide, an ether, a polyether, a polyamide, an ester, a mercaptan, a urea, a thiourea, a guanidyl, or a carbamoyl group, and at least one of $R_1$, $R_2$, $R_4$ and $R_5$ is a straight chain or branched, cyclic, alkyl, alkenyl, alkynyl or aryl group having from about 8 to about 24 carbon atoms;

Z is selected from the group consisting of spermiyl, spermidiyl, amino acid, peptidyl, diaminoalkyl, and polyamine;

m and n are 0 or 1; and l, b and c are integers independently selected from 1 to about 4;

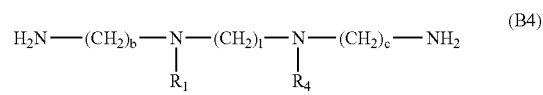

(B4)

wherein at least one of $R_1$ and $R_4$ is a straight chain or branched, cyclic, alkyl, alkenyl, alkynyl or aryl group having from about 8 to about 24 carbon atoms; and l, b and c are integers independently selected from 1 to about 4;

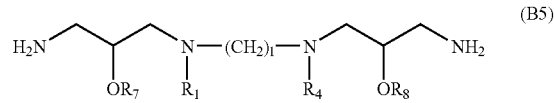

(B5)

wherein at least one of $R_1$ and $R_4$ are straight chain or branched, cyclic, alkyl, alkenyl, alkynyl or aryl groups having from about 8 to about 24 carbon atoms; $R_7$ and $R_8$ are independently hydrogen or a carbohydrate, preferably hydrogen; and l is an integer from 1 to about 4;

m and n are 0 or 1;
i and j are integers from about 2 to about 3; and
k is an integer from 1 to about 3;

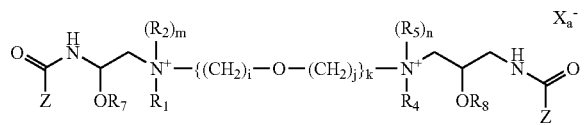
(B6)

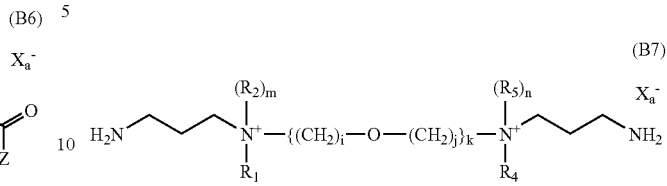
(B7)

wherein

Z is as defined above;
at least one of $R_1$ and $R_4$ is a straight chain or branched, cyclic, alkyl, alkenyl, alkynyl or aryl group having from about 8 to about 24 carbon atoms;
$R_2$ and $R_5$, independently of one another, are selected from the group consisting of H and a $C_1$–$C_8$ alkyl, alkenyl, aryl, and alkyl optionally substituted by one or more of an alcohol, an amine, an amide, an ether, a polyether, a polyamide, an ester, a mercaptan, a urea, a thiourea, a guanidyl, or a carbamoyl group;
$R_7$ and $R_8$ are independently H or a carbohydrate;

wherein at least one of $R_1$ and $R_4$ is a straight chain or branched, cyclic, alkyl, alkenyl, alkynyl or aryl group having from about 8 to about 24 carbon atoms;
$R_2$ and $R_5$, independently of one another, are selected from the group consisting of H and a $C_1$–$C_8$ alkyl, alkenyl, aryl, and alkyl optionally substituted by one or more of an alcohol, an amine, an amide, an ether, a polyether, a polyamide, an ester, a mercaptan, a urea, a thiourea, a guanidyl, or a carbamoyl group;
m and n are 0 or 1;
i and j are integers from about 2 to about 3; and
k is an integer from 1 to about 3;

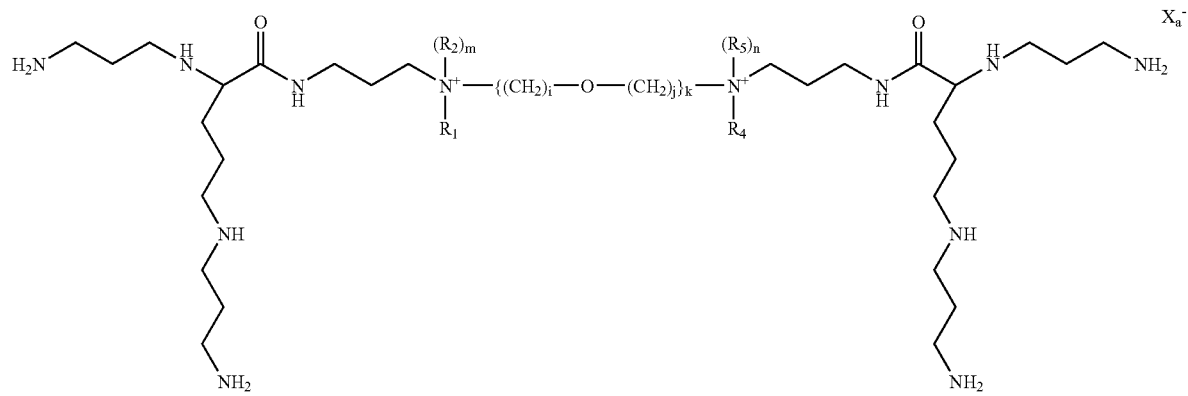

wherein
- at least one of $R_1$ and $R_4$ is a straight chain or branched, cyclic, alkyl, alkenyl, alkynyl or aryl group having from about 8 to about 24 carbon atoms;
- $R_2$ and $R_5$, independently of one another, are selected from the group consisting of H and a $C_1$–$C_8$ alkyl, alkenyl, aryl, and alkyl optionally substituted by one or more of an alcohol, an amine, an amide, an ether, a polyether, a polyamide, an ester, a mercaptan, a urea, a thiourea, a guanidyl, or a carbamoyl group;
- m and n are 0 or 1;
- i and j are integers from about 2 to about 3; and
- k is an integer from 1 to about 3;

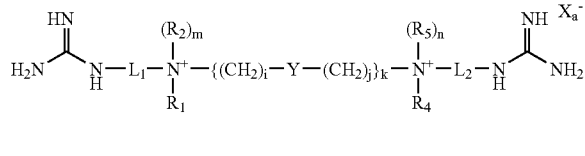

(B9)

wherein
- at least one of $R_1$ and $R_4$ is a straight chain or branched, cyclic, alkyl, alkenyl, alkynyl or aryl group having from about 8 to about 24 carbon atoms;
- $R_2$ and $R_5$, independently of one another, are selected from the group consisting of H and a $C_1$–$C_8$ alkyl, alkenyl, aryl, and alkyl optionally substituted by one or more of an alcohol, an amine, an amide, an ether, a polyether, a polyamide, an ester, a mercaptan, a urea, a thiourea, a guanidyl, or a carbamoyl group;
- m and n are 0 or 1;
- i and j are integers from about 2 to about 3;
- k is an integer from 1 to about 3;
- $L_1$ and $L_2$, independently from one another, are an alkylene or an alkylene ether; and
- Y is selected from the group consisting of $CH_2$, O, S and NH;

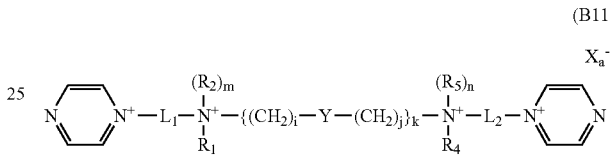

(B11)

wherein
- at least one of $R_1$ and $R_4$ is a straight chain or branched, cyclic, alkyl, alkenyl, alkynyl or aryl group having from about 8 to about 24 carbon atoms;
- $R_2$ and $R_5$, independently of one another, are selected from the group consisting of H and a $C_1$–$C_8$ alkyl, alkenyl, aryl, and alkyl optionally substituted by one or more of an alcohol, an amine, an amide, an ether, a polyether, a polyamide, an ester, a mercaptan, a urea, a thiourea, a guanidyl, or a carbamoyl group;
- m and n are 0 or 1;
- i and j are integers from about 2 to about 3;
- k is an integer from 1 to about 3;
- $L_1$ and $L_2$, independently from one another, are an alkylene or an alkylene ether; and
- Y is selected from the group consisting of $CH_2$, O, S and NH;

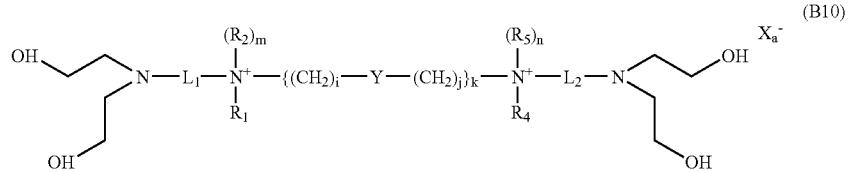

(B10)

wherein
- at least one of $R_1$ and $R_4$ is a straight chain or branched, cyclic, alkyl, alkenyl, alkynyl or aryl group having from about 8 to about 24 carbon atoms;
- $R_2$ and $R_5$, independently of one another, are selected from the group consisting of H and a $C_1$–$C_8$ alkyl, alkenyl, aryl, and alkyl optionally substituted by one or more of an alcohol, an amine, an amide, an ether, a polyether, a polyamide, an ester, a mercaptan, a urea, a thiourea, a guanidyl, or a carbamoyl group;
- m and n are 0 or 1;
- i and j are integers from about 2 to about 3;
- k is an integer from 1 to about 3;
- $L_1$ and $L_2$, independently from one another, are an alkylene or an alkylene ether; and
- Y is selected from the group consisting of $CH_2$, O, S and NH;

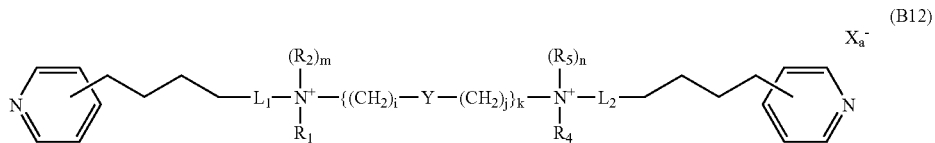

(B12)

wherein
- at least one of $R_1$ and $R_4$ is a straight chain or branched, cyclic, alkyl, alkenyl, alkynyl or aryl group having from about 8 to about 24 carbon atoms;
- $R_2$ and $R_5$, independently of one another, are selected from the group consisting of H and a $C_1$–$C_8$ alkyl, alkenyl, aryl, and alkyl optionally substituted by one or more of an alcohol, an amine, an amide, an ether, a polyether, a polyamide, an ester, a mercaptan, a urea, a thiourea, a guanidyl, or a carbamoyl group;
- m and n are 0 or 1;
- i and j are integers from about 2 to about 3;
- k is an integer from 1 to about 3;
- $L_1$ and $L_2$ independently from one another, are an alkylene or an alkylene ether; and
- Y is selected from the group consisting of $CH_2$, O, S and NH; and

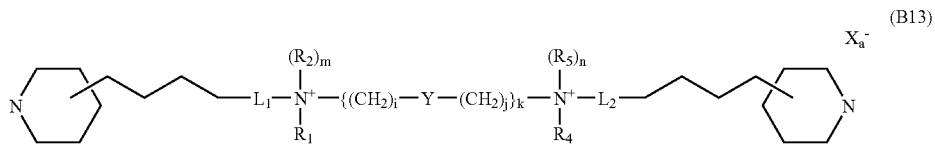

(B13)

wherein
- at least one of $R_1$ and $R_4$ is a straight chain or branched, cyclic, alkyl, alkenyl, alkynyl or aryl group having from about 8 to about 24 carbon atoms;
- $R_2$ and $R_5$, independently of one another, are selected from the group consisting of H and a $C_1$–$C_8$ alkyl, alkenyl, aryl, and alkyl optionally substituted by one or more of an alcohol, an amine, an amide, an ether, a polyether, a polyamide, an ester, a mercaptan, a urea, a thiourea, a guanidyl, or a carbamoyl group;
- m and n are 0 or 1;
- i and j are integers from about 2 to about 3;
- k is an integer from 1 to about 3;
- $L_1$ and $L_2$, independently from one another, are an alkylene or an alkylene ether; and
- Y is selected from the group consisting of $CH_2$, O, S and NH.

In each of formulae (B1) through (B13) preferably $R_1$ and $R_4$ are each $C_{6-30}$ alkyl or alkenyl, more preferably $C_{8-24}$ alkyl or alkenyl, and $R_2$ and $R_5$ or $R_3$ and $R_6$ are each hydrogen or $C_{1-8}$ alkyl.

Specific compounds within the scope of the invention include the following examples. $R_7$ and $R_8$ in the formulae are independently H or a carbohydrate, preferably H.

25
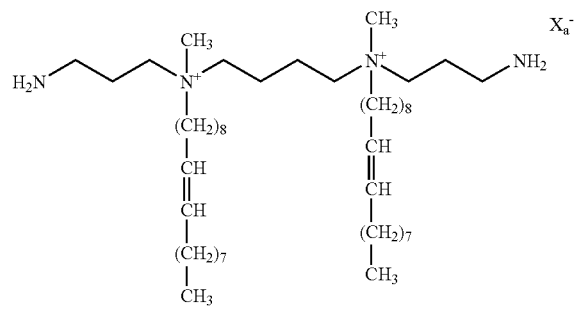
26
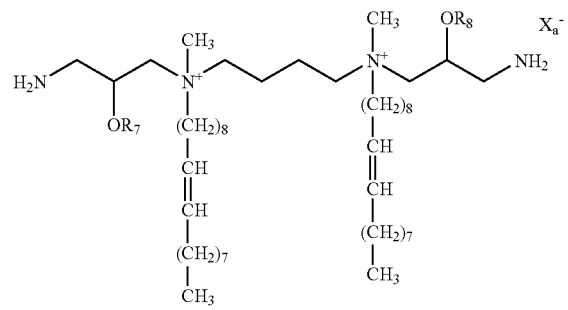
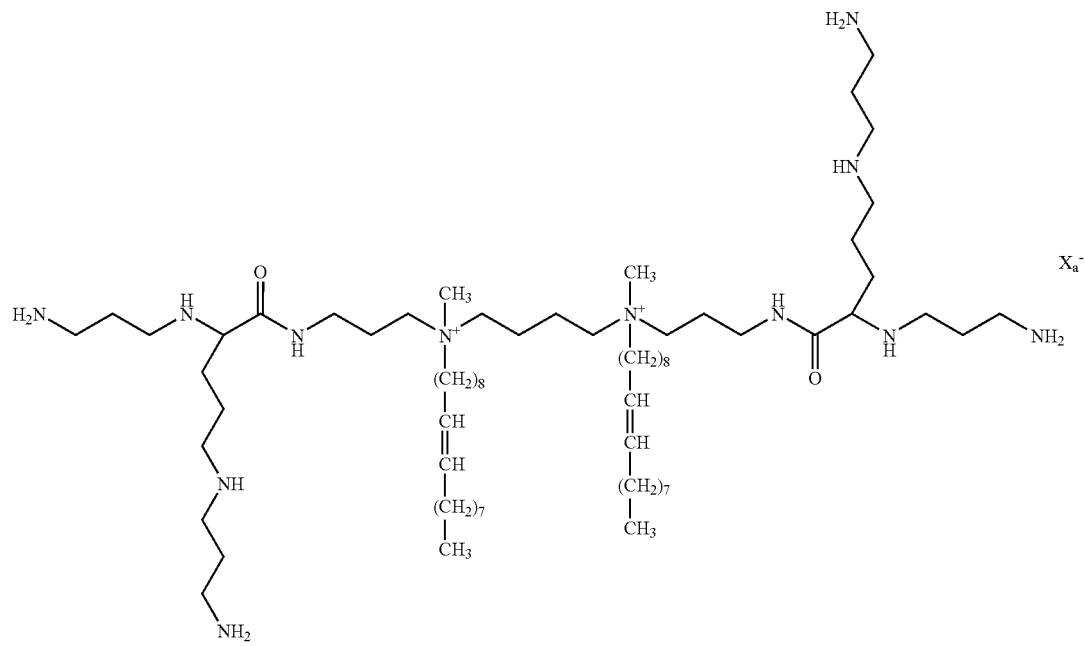
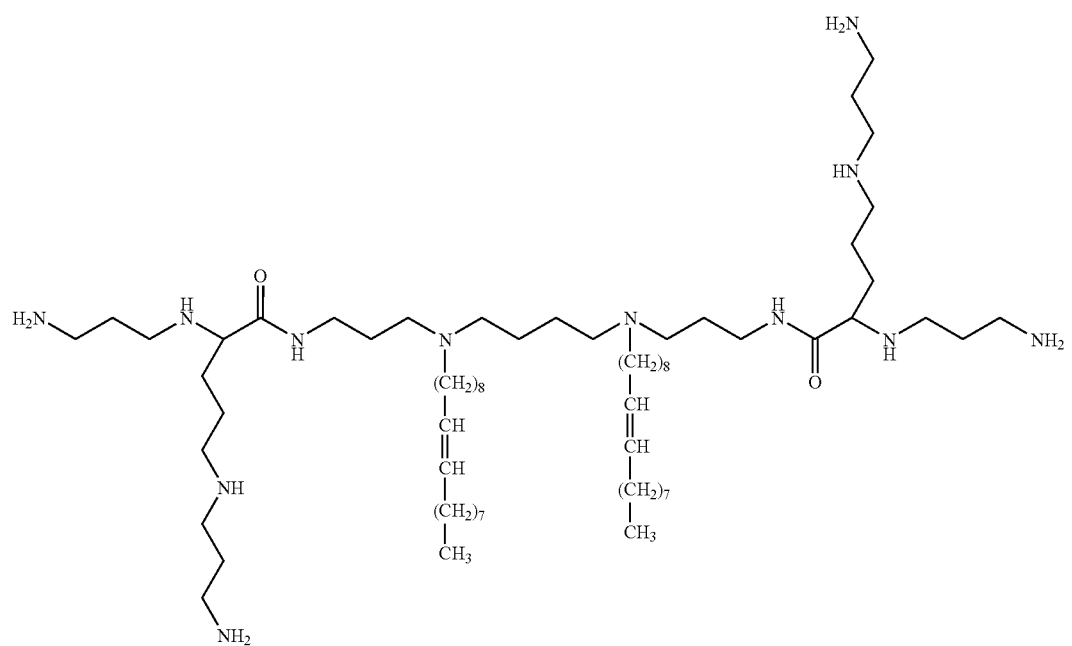

-continued
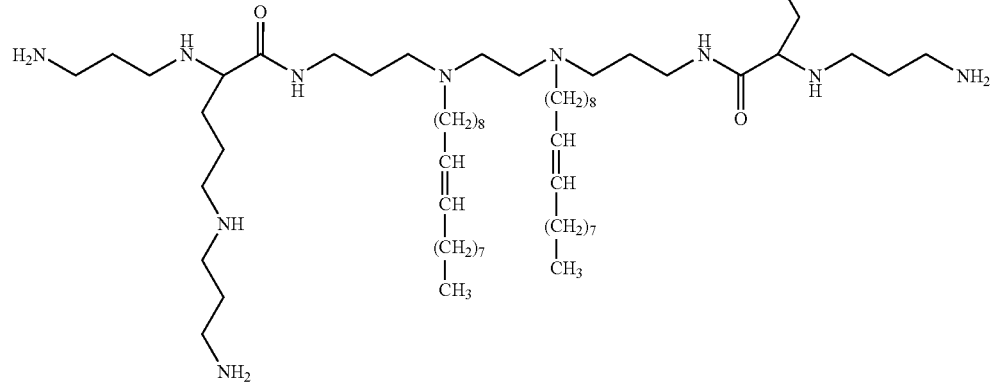
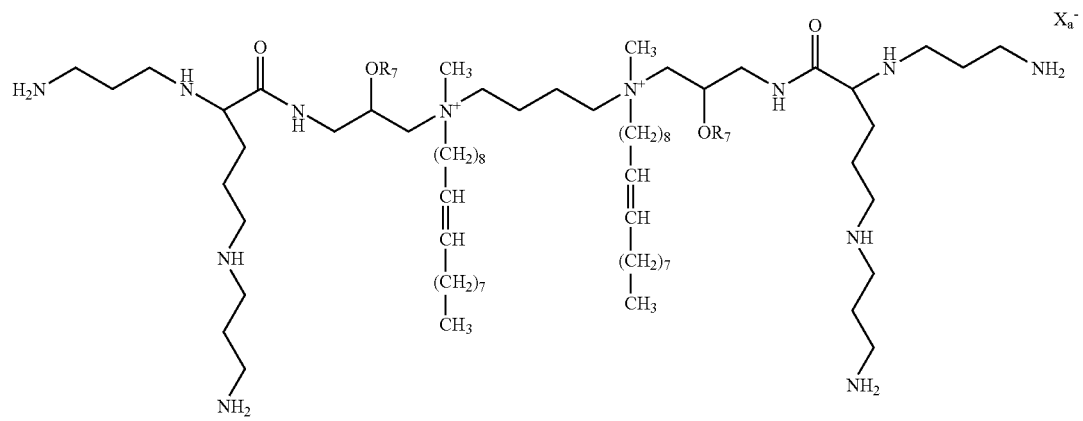
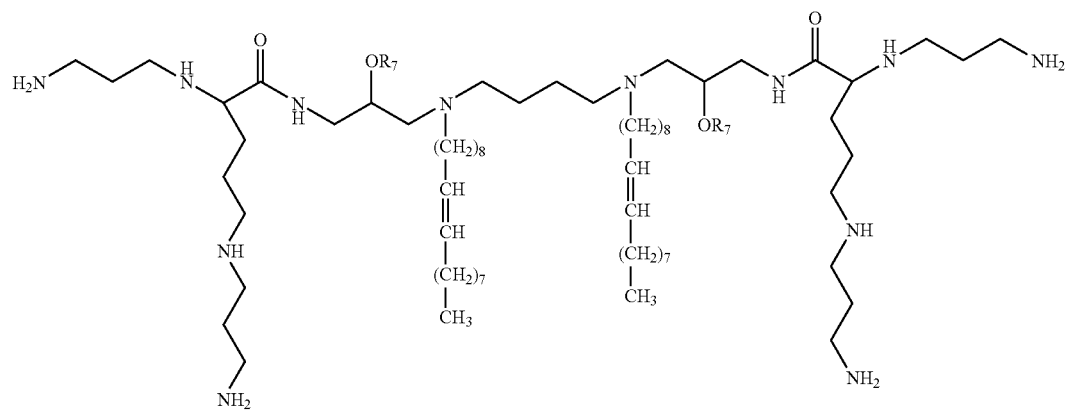

-continued
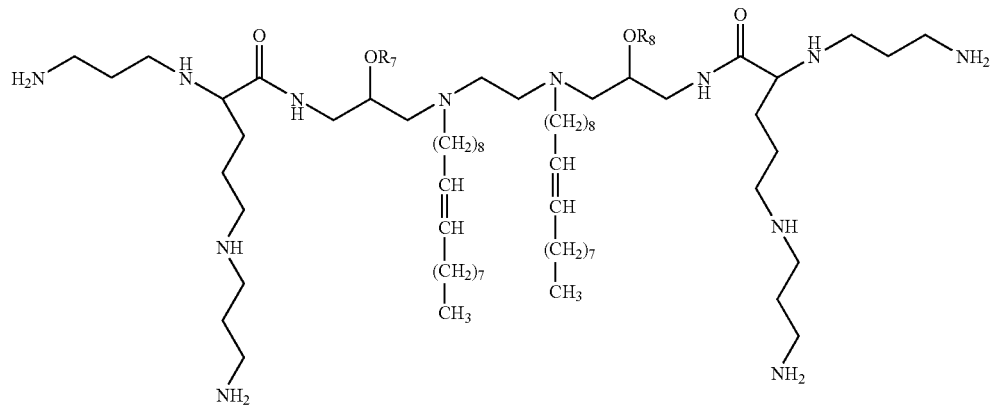
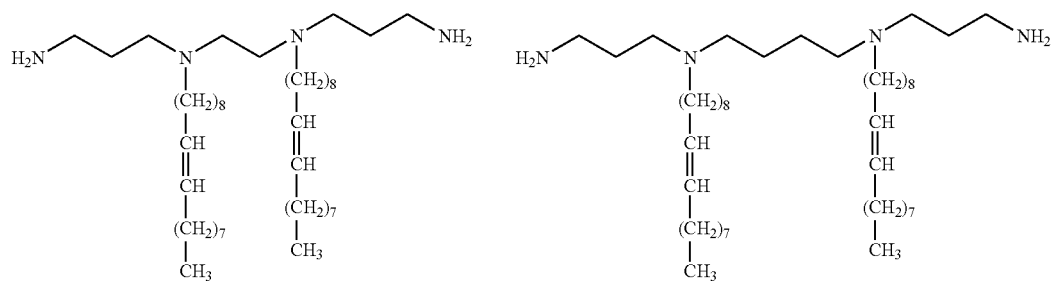
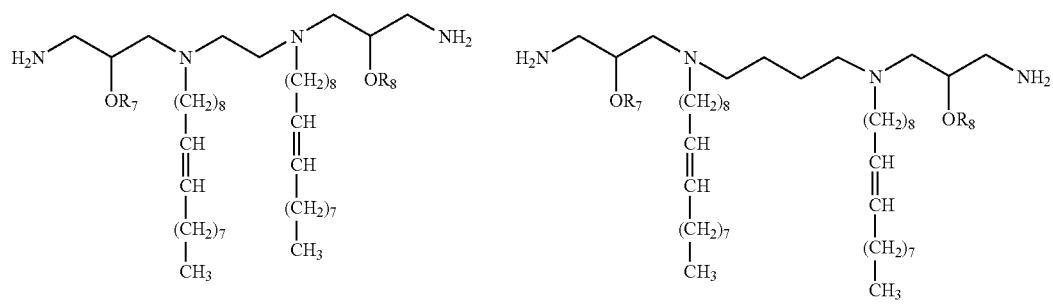
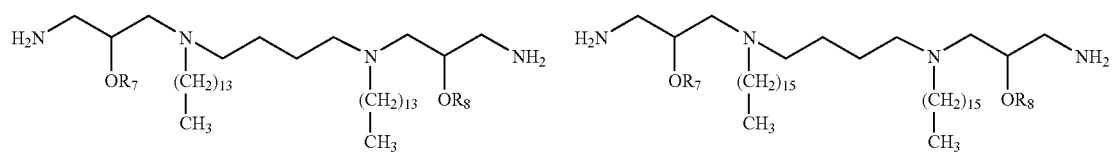
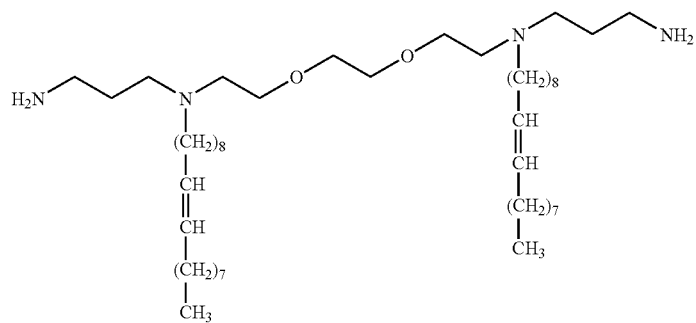

-continued
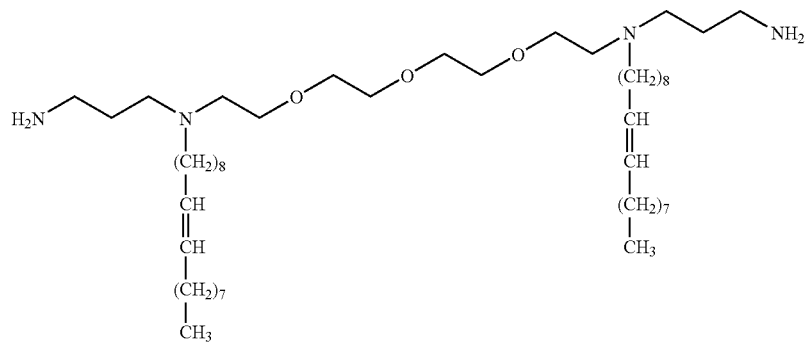
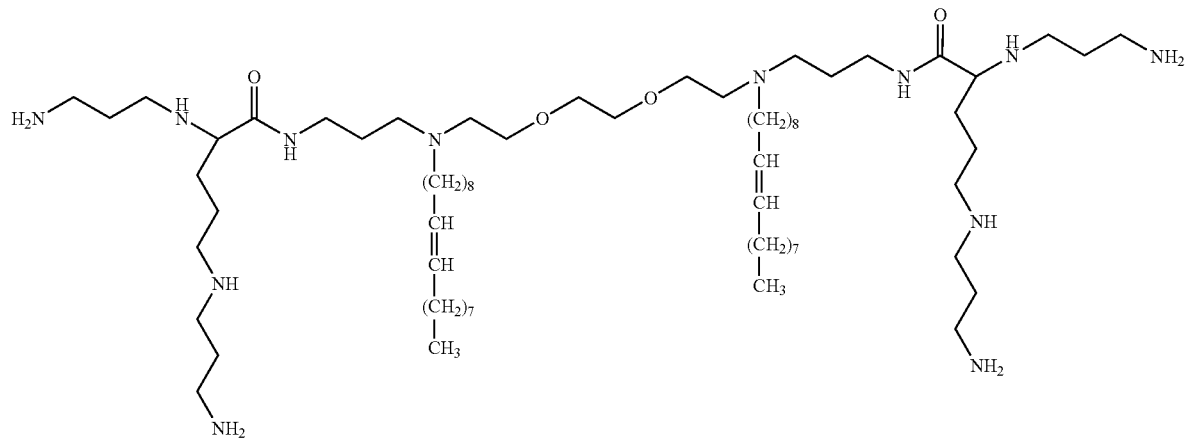
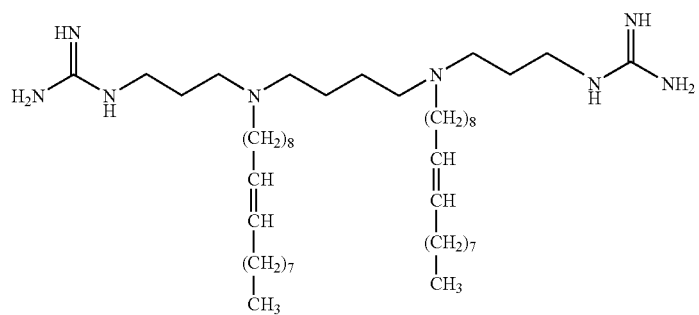
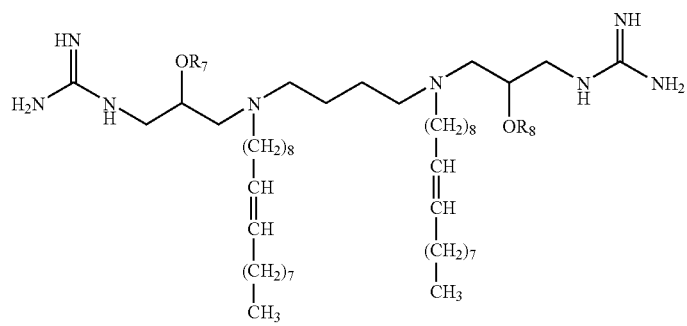

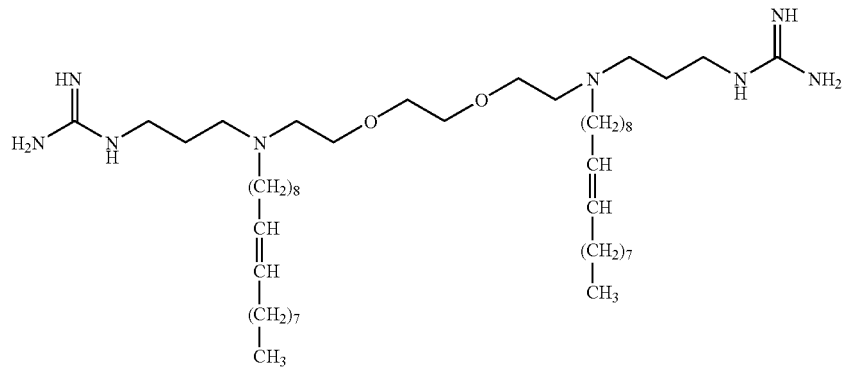
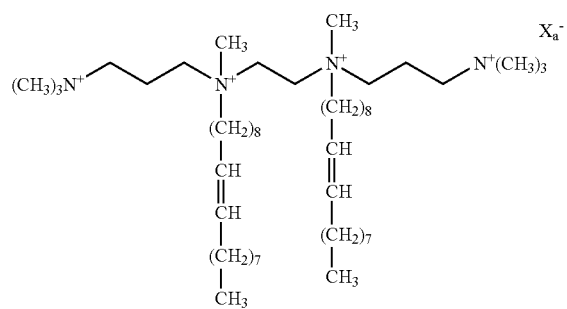
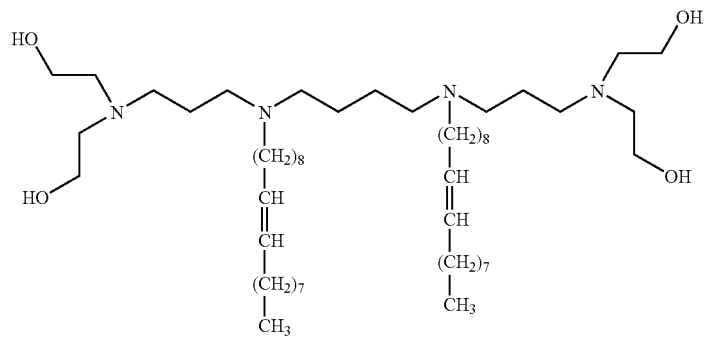
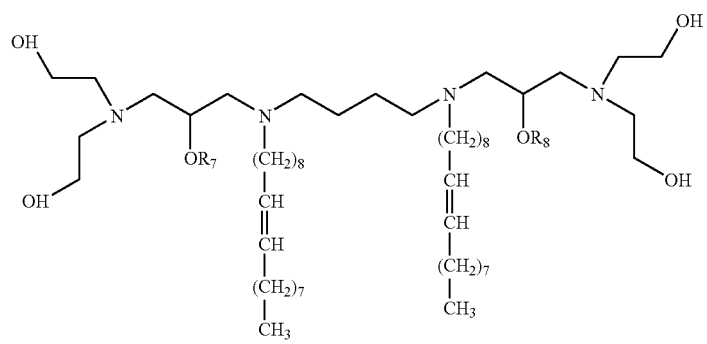

-continued
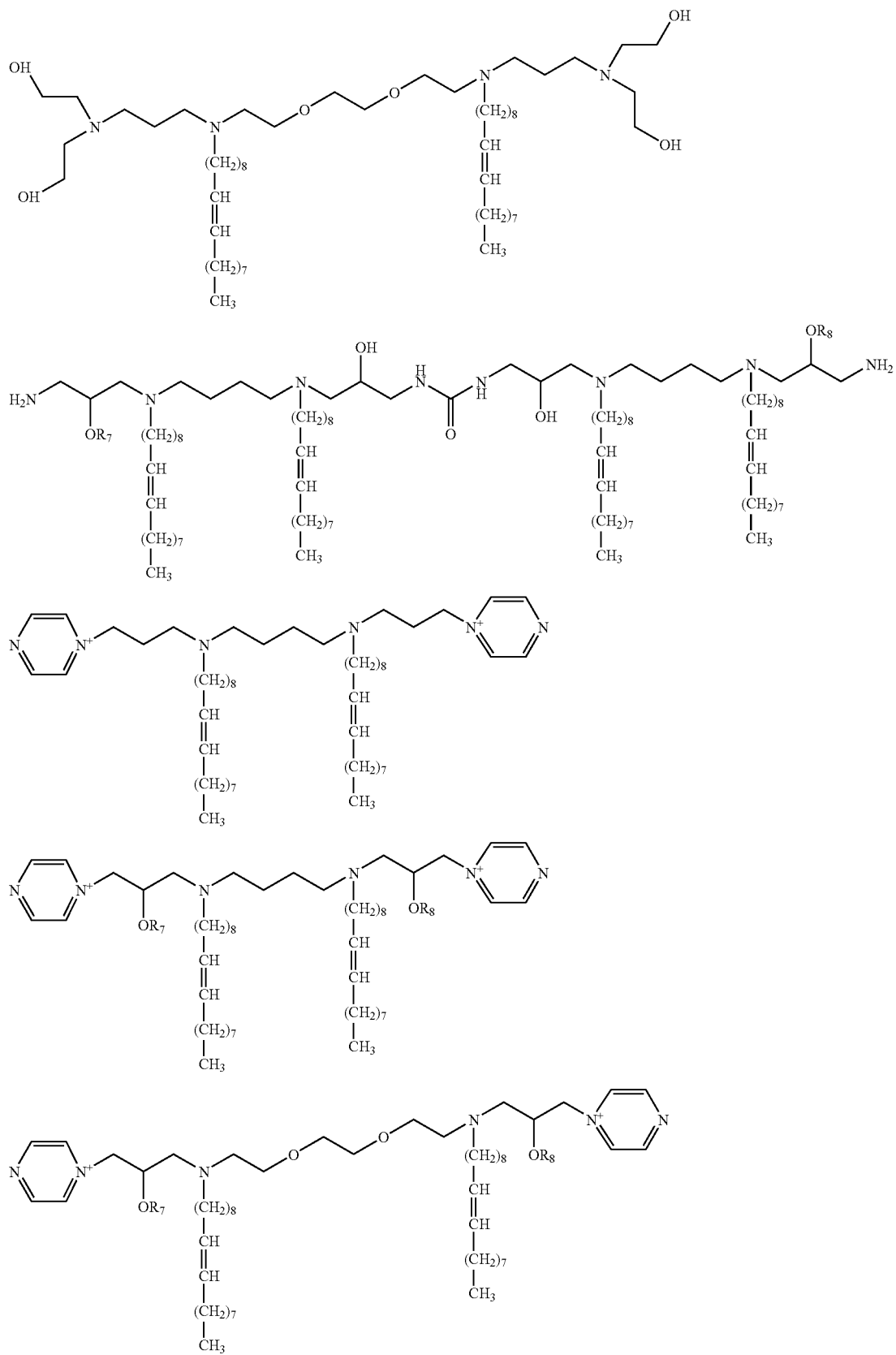

-continued
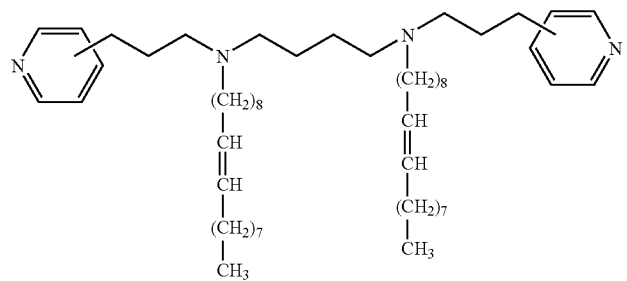
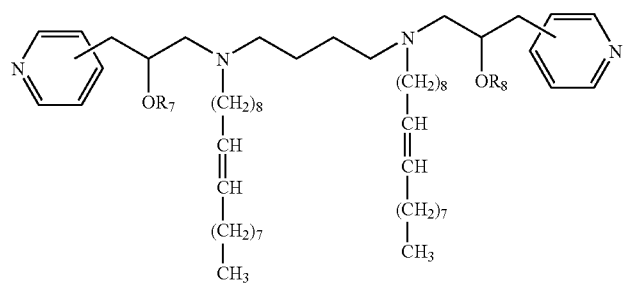
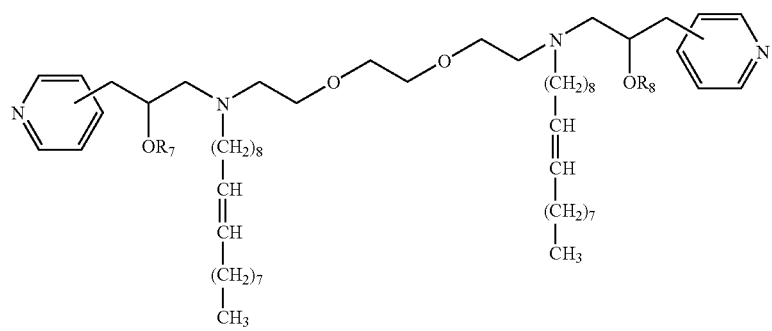
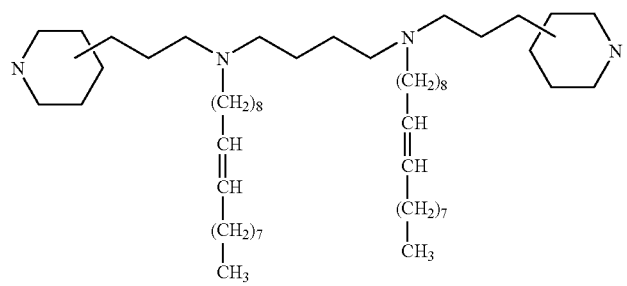
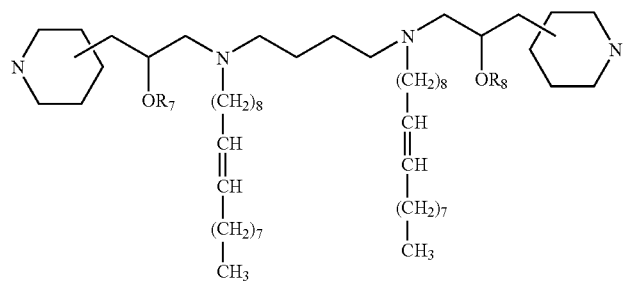

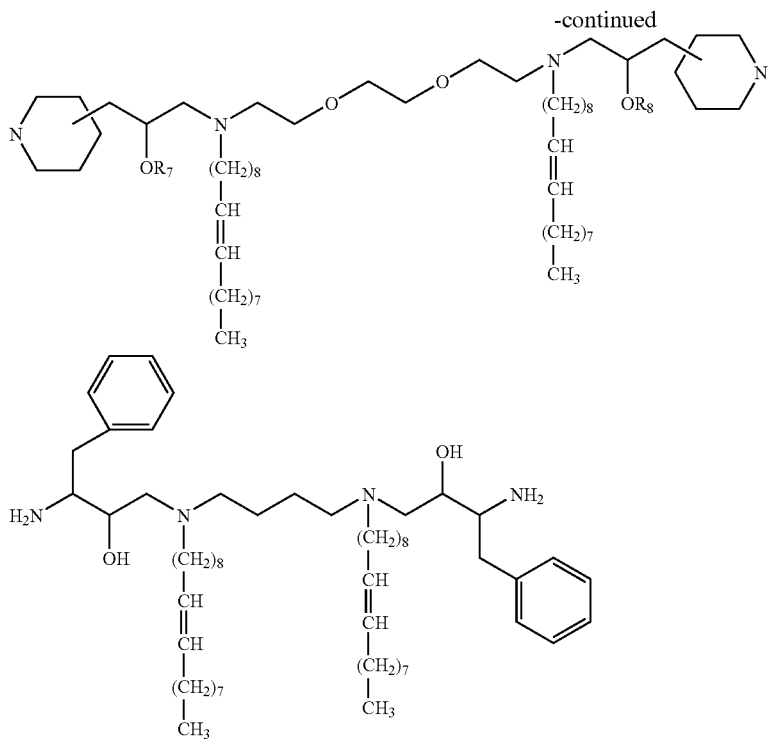

Further, the compounds according to the present invention have the Formula (C):

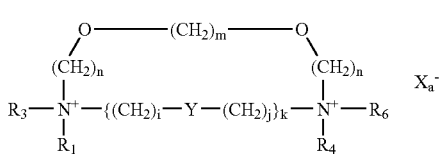

wherein

Y is selected from the group consisting of $CH_2$, an ether, a polyether, an amide, a polyamide, an ester, a sulfide, a urea, a thiourea, a guanidyl, a carbamoyl, a carbonate, a phosphate, a sulfate, a sulfoxide, an imine, a carbonyl, and a secondary amino group and wherein Y is optionally substituted by $-X_1-L'-X_2-Z$ or $-Z$;

$R_1$, $R_3$, $R_4$ and $R_6$, independently of one another, are selected from the group consisting of H, $\{CH_2\}_p-D-Z$, an alkyl, an alkenyl, an aryl, and an alkyl or an alkyl ether optionally substituted by one or more of an alcohol, an aminoalcohol, an amine, an amide, an ether, a polyether, a polyamide, an ester, a mercaptan, an alkylthio, a urea, a thiourea, a guanidyl, or a carbamoyl group, and at least one of $R_1$, $R_3$, $R_4$ and $R_6$ is a straight chain or branched, cyclic, alkyl, alkenyl, alkynyl or aryl group, and $R_1$, $R_3$, $R_4$ and $R_6$ may optionally be covalently linked with each other or with Y, to form a cyclic moiety;

Z is selected from the group consisting of amine, spermiyl, carboxyspermiyl, guanidyl, spermidinyl, putricinyl, diaminoalkyl, pyridyl, piperidinyl, pyrrolidinyl, polyamine, amino acid, peptide, and protein;

$X_1$ and $X_2$, independently of one another, are selected from the group consisting of NH, O, S, alkylene, and arylene;

L' is selected from the group consisting of alkylene, alkenylene, alkynylene, arylene, alkylene ether, and polyether;

D is Q or a bond;

m and n are 0 or 1; and i, j, k, l and p are integers independently selected from 1 to about 10.

Preferably, Y is selected from the group consisting of $CH_2$, an ether, a polyether, an amide, a polyamide, an ester, a sulfide, a urea, a thiourea, a guanidyl, a carbamoyl, a carbonate, and a secondary amino group.

Preferably, $R_1$, $R_3$, $R_4$ and $R_6$, independently of one another, are selected from the group consisting of H, $-(CH_2)_p-Z$, an alkyl, an alkenyl, an aryl, and an alkyl or an alkyl ether optionally substituted by one or more of an alcohol, an aminoalcohol, an amine, an amide, an ether, a polyether, a polyamide, an ester, a mercaptan, a urea, a thiourea, a guanidyl, or a carbamoyl group, and at least one of $R_1$, $R_3$, $R_4$ and $R_6$ is a straight chain or branched, cyclic, alkyl, alkenyl, alkenyl or aryl group, and $R_1$, $R_3$, $R_4$ and $R_6$ may be covalently linked with each other, to form a cyclic moiety.

Preferably, at least one of $R_1$ and $R_4$ is straight chain or branched, cyclic, alkyl, alkenyl, alkynyl or aryl group having from about 2 to 100, preferably 4 to 75, more preferably 6 to 64, more preferably 8 to 50, more preferably 8 to 40, more preferably 8 to 30, more preferably 6 to 30, more preferably 4 to 30, and most preferably 8 to about 24 carbon atoms.

Preferably, Y is selected from the group consisting of $CH_2$, O, S and NH.

The compounds and polycations of the present invention have the following Formula (D):

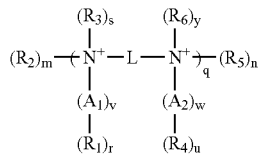

wherein

L is C, CH, $(CH_2)_1$, or $\{(CH_2)_i-Y-(CH_2)_j\}_k$, wherein Y is selected from the group consisting of $CH_2$, an ether, a polyether, an amide, a polyamide, an ester, a sulfide, a urea, a thiourea, a guanidyl, a carbamoyl, a carbonate, a phosphate, a sulfate, a sulfoxide, an imine, a carbonyl, and a secondary amino group and wherein Y is optionally substituted by $-X_1-L'-X_2-Z$ or $-Z$;

$R_1-R_6$, independently of one another, are selected from the group consisting of H, $-(CH_2)_p-D-Z$, an alkyl, an alkenyl, an aryl, and an alkyl or an alkyl ether optionally substituted by one or more of an alcohol, an aminoalcohol, an amine, an amide, an ether, a polyether, a polyamide, an ester, a mercaptan, an alkylthio, a urea, a thiourea, a guanidyl, or a carbamoyl group, and wherein at least one of $R_1$, $R_3$, $R_4$ and $R_6$ is a straight chain or branched, cyclic, alkyl, alkenyl, alkynyl or aryl group;

Z is selected from the group consisting of amine, spermiyl, carboxyspermiyl, guanidyl, spermidinyl, putricinyl, diaminoalkyl, pyridyl, piperidinyl, pyrrolidinyl, polyamine, amino acid, amino acid derivative, peptide, and protein;

$X_1$ and $X_2$, independently of one another, are selected from the group consisting of NH, O, S, alkylene and arylene;

L' is selected from the group consisting of alkylene, alkenylene, alkynylene, arylene, alkylene ether, and polyether;

$A_1$ and $A_2$, independently of one another, are selected from the group consisting of $CH_2O$, $CH_2S$, $CH_2NH$, $C(O)$, $C(NH)$, $C(S)$ and $(CH_2)_t$;

m, n, r, s, u, v, w and y are 0 or 1, with the proviso that when both m and n are 0 at least one of r, s, u and y is other than 0;

i, j, k, l, p and t are integers from 0 to about 100; and q is an integer from 1 to about 1000.

Also, the compounds and the polycations of the present invention have the following Formula (E):

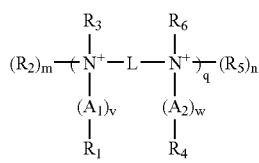

wherein

L is $(CH_2)$, or $\{(CH_2)_i-Y-(CH_2)_j\}_k$, wherein Y is selected from the group consisting of $CH_2$, an ether, a polyether, an amide, a polyamide, an ester, a sulfide, a urea, a thiourea, a guanidyl, a carbamoyl, a carbonate, and a secondary amino group;

$R_1-R_6$, independently of one another, are selected from the group consisting of H, $-(CH_2)_p-Z$, an alkyl, an alkenyl, an aryl, and an alkyl or an alkyl ether optionally substituted by one or more of an alcohol, an aminoalcohol, an amine, an amide, an ether, a polyether, a polyamide, an ester, a mercaptan, a urea, a thiourea, a guanidyl, or a carbamoyl group, and at least one of $R_1$, $R_3$, $R_4$ and $R_6$ is a straight chain or branched, cyclic, alkyl, alkenyl, alkynyl or aryl group; Z, $A_1$, $A_2$, m, n, i, j, k, l, p, t and q are as defined above.

In the above formulae (D) and (E), $R_1-R_6$, Y, i, j, k, l, p, t and q are preferably as defined with reference to Formula (A).

It would be obvious for a skilled person that when Q is O or S, the number of substituents should be according their valency.

Certain of the compounds of the invention may be insufficiently soluble in physiological media to employ for delivery and transfection methods. Those of ordinary skill in the art will appreciate that there are a variety of techniques available in the art to enhance solubility of such compounds in aqueous media. Such methods are readily applicable without undue experimentation to the compounds described herein.

Definitions

Useful aryl groups are $C_{6-100}$ aryl, preferably $C_{6-75}$ aryl, more preferably $C_{6-64}$ aryl, more preferably $C_{6-50}$ aryl, more preferably $C_{6-40}$ aryl, more preferably $C_{6-30}$ aryl, most preferably $C_{6-24}$ aryl. Typical $C_{6-100}$ aryl groups include phenyl, naphthyl, phenanthryl, anthracyl, indenyl, azulenyl, biphenyl, biphenylenyl, fluorenyl, pyrenyl, aceanthrenyl, cholantrenyl, acephenanthrenyl, violantherenyl, hexaphenyl, hexacenyl, trinaphtyl and pyranthyl groups.

Useful alkyl groups are straight chain or branched $C_{2-100}$ alkyl groups, preferably $C_{4-75}$ alkyl, more preferably $C_{6-64}$ alkyl, more preferably $C_{8-50}$ alkyl, more preferably $C_{8-40}$ alkyl, more preferably $C_{8-30}$ alkyl, more preferably $C_{6-30}$ alkyl, more preferably $C_{4-30}$ alkyl, most preferably $C_{8-24}$ alkyl. Typical $C_{2-100}$ alkyl groups include ethyl, propyl, isopropyl, butyl, sec-butyl, tert-butyl, pentyl, hexyl, octyl, decyl, dodecyl, tetradecyl, hexadecyl, octadecyl, eicosyl, docosyl, tetracosyl, hexacosyl, octacosyl and triacontyl groups. Also contemplated is a trimethylene group substituted on two adjoining positions on any benzene ring of the compounds of the invention.

Useful alkenyl groups are straight chain or branched $C_{2-100}$ alkenyl, preferably $C_{4-75}$ alkenyl, more preferably $C_{6-64}$ alkenyl, more preferably $C_{8-50}$ alkenyl, more preferably $C_{8-40}$ alkenyl, more preferably $C_{8-30}$ alkenyl, more preferably $C_{6-30}$ alkenyl, more preferably $C_{4-30}$ alkenyl, most preferably $C_{8-24}$ alkenyl. Typical $C_{2-100}$ alkenyl groups include ethenyl, propenyl, isopropenyl, butenyl, sec-butenyl, hexenyl, octenyl, decenyl, dodecenyl, especially 9-dodecenyl, tetradecenyl, especially 9-tetradecenyl, hexadecenyl, especially 9-hexadecenyl, octadecenyl, especially 9-octadecenyl, eicosenyl, docosenyl, tetracosenyl, hexacosenyl, octacosenyl and triacontenyl.

Useful alkynyl groups are straight chain or branched $C_{2-100}$ alkynyl, preferably $C_{4-75}$ alkynyl, more preferably $C_{6-64}$ alkynyl, more preferably $C_{8-50}$ alkynyl, more preferably $C_{8-40}$ alkynyl, more preferably $C_{8-30}$ alkynyl, more preferably $C_{6-30}$ alkynyl, more preferably $C_{4-30}$ alkynyl, most preferably $C_{8-24}$ alkynyl. Typical $C_{2-100}$ alkynyl groups include ethynyl, propynyl, butynyl,-butynyl, hexynyl, octynyl, decynyl, dodecynyl, tetradecynyl, hexadecynyl, octadecynyl, eicosynyl, docosynyl, tetracosynyl, hexacosynyl, octacosynyl and triacontynyl groups.

Typical alkyl ether groups include any of the above-mentioned $C_{2-100}$ alkyl groups having an ether group.

An ether group is —O—.

Typical polyether groups include the —(CHR$^{14}$—CH$_2$—O)$_t$—, wherein R$^{14}$ is H or a $C_{1-4}$ alkyl group and t is an integer as defined above, preferably t is 2 to 5.

For the purposes of the invention an amide group is an organic radical having —NHC(O)— as a functional group. Typical amide groups include alkyl amides, alkenyl amides, alkynyl amides, and aryl amides, wherein alkyl, alkenyl, alkynyl and aryl are as defined above.

Typically polyamide groups include organic radicals having two or more amide groups as defined above.

Typically an ester group is an organic radical having —C(O)O— as a functional group. Typical ester groups include R$^{14}$—C(O)—O—R$^{15}$, wherein R$^{14}$ and R$^{15}$ are alkylene, alkenylene, alkynylene and arylene groups as defined above.

Typically urea groups are organic radicals having —NH—C(O)—NH— as a functional group. Typical urea groups include R$^4$NH—C(O)—NHR$^{14}$, R$^{14}$NH—C(O)—NHR$^{15}$, R$^{14}$R$^{15}$N—C(O)—NR$^{14}$R$^{15}$ wherein R$^{14}$ and R$^{15}$ are alkylene, alkenylene, alkynylene and arylene groups as defined above.

Typically thiourea groups are organic radicals having urea group as defined above wherein the oxygen in the urea group is substituted by sulfur.

Typically guanidyl groups are organic radicals having —NH—C(NH)NH— as a functional group. Typical guanidyl groups include R$^{14}$NH—C(NH)—NHR$^{14}$, R$^{14}$NH—C(NH)NHR$^{15}$ and R$^{14}$R$^{15}$N—C(NH)—NR$^{14}$R$^{15}$ wherein R$^{14}$ and R$^{15}$ are alkylene, alkenylene, alkynylene and arylene groups as defined above.

A carbamoyl group is —NH—C(O)O—.

Typically carbonate groups include organic radicals containing a $CO_3^{2-}$ radical, i.e., —C(O)O.

A phosphate group is a $PO_4^{3-}$ radical.

A sulfate group is a $SO_4^{2}$ radical.

A sulfoxide group is —S(O).

An imine group is —C(N)—.

A carbonyl group is —C(O)—.

A secondary amino group is —NH—.

Typically aminoalcohol groups are organic radicals having both a secondary amino group as defined above and a hydroxyl group. Typical aminoalcohols include aminoethanol, aminopropanol and aminobutanol.

The definition "D is a bond" means that when D is not Q there is a single bond between (CH$_2$)$_p$ and Z.

Biologically Active Substance refers to any molecule or mixture or complex of molecules that exerts a biological effect in vitro and/or in vivo, including pharmaceuticals, drugs, proteins, peptides, polypeptides, hormones, vitamins, steroids, polyanions, nucleosides, nucleotides, nucleic acids (e.g. DNA or RNA), nucleotides, polynucleotides, etc.

Cationic Lipids refers to any cationic lipids which may be used for transfection, including but not limited to, DOSPA, DOTMA, DMRIE, DOTAP, DOGS and TM-TPS.

Cell refers to eukaryotic cells of any type and from any source. Types of eukaryotic cells include epithelial, fibroblastic, neuronal, hematopoietic cells and the like from primary cells, tumor cells or immortalized cell lines. Sources of such cells include any animal such as human, canine, mouse, hamster, cat, bovine, porcine, monkey, ape, sheep, fish, insect, fungus and any plant including crop plants, ornamentals and trees.

Delivery is used to denote a process by which a desired compound is transferred to a target cell such that the desired compound is ultimately located inside the target cell or in, or on, the target cell membrane. In many uses of the compounds of the invention, the desired compound is not readily taken up by the target cell and delivery via lipid aggregates is a means for getting the desired compound into the cell. In certain uses, especially under in vivo conditions, delivery to a specific target cell type is preferable and can be facilitated by compounds of the invention.

Drug refers to any therapeutic or prophylactic agent other than food which is used in the prevention, diagnosis, alleviation, treatment, or cure of disease in man or animal.

Kit refers to transfection or protein expression kits which include one or more of the compounds of the present invention or mixtures thereof. Such kits may comprise a carrying means being compartmentalized to receive in close confinement one or more container means such as vials, test tubes and the like. Each of such container means comprises components or a mixture of components needed to perform transfection. Such kits may include one or more components selected from nucleic acids (preferably one or more vectors), cells, one or more compounds of the present invention, lipid-aggregate forming compounds, transfection enhancers, biologically active substances, etc.

Lipid Aggregate is a generic term which includes liposomes of all types both unilamellar and multilameller as well as micelles and more amorphous aggregates of cationic lipids or lipids mixed with amphiphatic lipids such as phospholipids and steroids.

Lipid Aggregate-forming Compounds refers to neutral compounds or lipids such as DOPE, DOPC and cholesterol, etc.

Target Cell refers to any cell to which a desired compound is delivered, using a lipid aggregate as carrier for the desired compound.

Transfection is used herein to mean the delivery of nucleic acid, protein or other macromolecule to a target cell, such that the nucleic acid, protein or other macromolecule is expressed or has a biological function in the cell. The term "expressible nucleic acid" includes both DNA and RNA without regard to molecular weight, and the term "expression" means any manifestation of the functional presence of the nucleic acid within the cell including, without limitation, both transient expression and stable expression. Functional aspects include inhibition of expression by oligonucleotides or protein delivery.

Transfection Enhancers refers generally to molecules and substances such as proteins, peptides, growth factors and the like that enhance cell-targeting, uptake, internalization, nuclear targeting and expression. Such molecules and substances include ligands such as insulin, transferrin, fibronectin that target the cell surface; peptides that target cellular integrin receptors; and other compounds such as Plus Reagent (available from Life Technologies, Inc., Rockville, Md.). Examples of transfection enhancers may be found in U.S. Pat. No. 5,736,392 and U.S. application Ser. No. 09/039,780 filed Mar. 16, 1998.

The invention will be further clarified by the following examples, which are intended to be purely exemplary of the invention. The polycationic lipids were prepared by following the general reaction schemes described below.

EXAMPLE 1

Synthesis of $N^1,N^4$-dioleoyl-diaminobutane (I)

A solution of 1,4-diaminobutane (4.28 g, 48.6 mmol) and triethylamine (20.4 ml, 146 mmol) in 10 mL of dry methylene chloride was slowly added to a solution of oleoyl chloride (30.0 g, 99.7 mmol) in 300 ml of anhydrous methylene chloride in an ice bath at 0° C. The reaction mixture was stirred vigorously with a mechanical stirrer. After the addition was complete, the ice bath was removed and the mixture was stirred at room temperature for 2.5 days. TLC analysis confirmed that the reaction had gone to completion and the product had precipitated. The excess oleoyl chloride was removed by filtration. The precipitate was washed twice with 50 ml of methylene chloride. The mother liquor was concentrated and more product precipitated. This precipitate was filtered and combined with the previous precipitate. The resulting solid was vacuum dried for 4 hours. A total of 27.0 g of a white solid of the desired product, $N^1,N^4$-dioleoyl-diaminobutane, was obtained.

Synthesis of $N^1,N^4$-dioleyl-diaminobutane (II)

Lithium aluminum hydride (8.62 g, 95%, 216 mmol) was carefully added to a suspension of $N^1,N^4$-dioleoyl-diaminobutane (27.0 g, 43.8 mmol) in 400 ml of anhydrous diethyl ether at 0° C. After addition, the ice bath was removed. The reaction mixture was warmed slowly to room temperature and then heated gently to reflux with an appropriate condensing device and stirred for 16 hours. The reaction mixture was then cooled and quenched carefully at 0° C. with 70 mL of a 1 N sodium hydroxide solution. Another 500 mL of diethyl ether was added and the mixture was stirred at room temperature for additional 2 hours. The top ether layer turned clear gradually and then separated. The aqueous layer was extracted three times with 100 mL of diethyl ether each. The combined ether solution was concentrated, and dried on high vacuum overnight. Total of 17.0 g of oily colorless $N^1,N^4$-dioleyl-diaminobutane was obtained.

Synthesis of $N^1,N^4$-dioleyl-$N^1,N^4$-di-[2-hydroxy-3-(N-phthalamido)propyl]-diamino-butane (III)

Diisopropylethylamine (11.1 mL, 63.7 mmol) was added to a suspension of $N^1,N^4$-dioleyl-diaminobutane (15.5 g, 26.3 mmol) and N-(2,3-epoxypropyl)-phthalimide (15.6 g, 76.8 mmol) in 110 mL of dry N,N-dimethylformamide. After purging with nitrogen, the reaction mixture was sealed in a round-bottom flask and heated to around 90° C. for 24 hours. N,N-dimethylformamide and diisopropylethylamine were removed and a yellow oil was obtained. This crude material was recrystallized from ethanol. A total of 18.6 g of a white solid, $N^1,N^4$-dioleyl-$N^1,N^4$-di-[2-hydroxy-3-(N-phthalamido)propyl]-diamino-butane was obtained.

Synthesis of $N^1,N^4$-dioleyl-$N^1,N^4$-di-[2-hydroxy-3-(N-aminopropyl)]-diaminobutane (IV) (hereinafter referred to as DHDOS)

Hydrazine (4.0 mL, 80% aq., 103 mmol) was added to a suspension of $N^1,N^4$-dioleyl-$N^1,N^4$-di-[2-hydroxy-3-(N-phthalamido)propyl]-diaminobutane (17.0 g, 17.1 mmol) in 250 mL of dry ethanol at room temperature. With an appropriate condensing device, the reaction mixture was heated to a reflux, at which point the suspension turned into a clear solution. The oil bath was set to 85° C. After 45 minutes a white solid precipitated from the solution. The reaction mixture was stirred at reflux for 4 hours before being cooled to −20° C. The white solid settled down to the bottom. The top clear ethanol solution was decanted. The residue was washed twice with cold ethanol. The combined ethanol solution was concentrated and dried overnight over vacuum. 12.4 g of oily $N^1,N^4$-dioleyl-$N^1,N^4$-di-[2-hydroxy-3-(N-aminopropyl)]-diaminobutane was obtained.

The following compounds were synthesized by the above method using the corresponding diamine and a long chain acyl chloride:

$N^1,N^4$-dimyristyl-$N^1,N^4$-di-[2-hydroxy-3-(N-aminopropyl)]-diaminobutane;

$N^1,N^4$-dipalmityl-$N^1,N^4$-di-[2-hydroxy-3-(N-aminopropyl)]-diaminobutane;

$N^1,N^4$-dipalmitolyl-$N^1,N^4$-di-[2-hydroxy-3-(N-aminopropyl)]-diaminobutane;

$N^1,N^4$-distearyl-$N^1,N^4$-di-[2-hydroxy-3-(N-aminopropyl)]-diaminobutane;

$N^1,N^4$-dilauryl-$N^1,N^4$-di-[2-hydroxy-3-(N-aminopropyl)]-diaminobutane;

$N^1,N^2$-dimyristyl-$N^1$, $N^1$-di-[2-hydroxy-3-(N-aminopropyl)]-diaminoethane;

$N^1,N^2$-dipalmityl-$N^1,N^2$-di-[2-hydroxy-3-(N-aminopropyl)]-diaminoethane;

$N^1,N^2$-dipalmitolyl-$N^1,N^2$-di-[2-hydroxy-3-(N-aminopropyl)]-diaminoethane;

$N^1,N^2$-distearyl-$N^1,N^2$-di-[2-hydroxy-3-(N-aminopropyl)]-diaminoethane;

$N^1,N^2$-dilauryl-$N^1,N^2$-di-[2-hydroxy-3-(N-aminopropyl)]-diaminoethane;

$N^1,N^2$-dioleyl-$N^1,N^2$-di-[2-hydroxy-3-(N-aminopropyl)]-diaminoethane;

$N^1,N^8$-dimyristyl-$N^1,N^8$-di-[2-hydroxy-3-(N-aminopropyl)]-Jeffamine;

$N^1,N^8$-dipalmityl-$N^1,N^8$-di-[2-hydroxy-3-(N-aminopropyl)]-Jeffamine;

$N^1,N^8$-dipalmitolyl-$N^1,N^8$-di-[2-hydroxy-3-(N-aminopropyl)]-Jeffamine;

$N^1,N^8$-distearyl-$N^1,N^8$-di-[2-hydroxy-3-(N-aminopropyl)]-Jeffamine;

$N^1,N^8$-dilauryl-$N^1,N^8$-di-[2-hydroxy-3-(N-aminopropyl)]-Jeffamine;

$N^1,N^8$-dioleyl-$N^1,N^8$-di-[2-hydroxy-3-(N-aminopropyl)]-Jeffamine.

Synthesis of $N^1,N^4$-dioleyl —$N^1,N^4$-di-[2-hydroxy-3-(N-carboxamidine)aminopropyl]-diaminobutane (V)

1H-pyrazole-1-carboxamidine hydrochloride (45 mg, 0.31 mmol) was added to a solution of $N^1,N^4$-dioleyl-$N^1,N^4$-di-[2-hydroxy-3-(N-aminopropyl)]-diamino-butane (115 mg, 0.156 mmol) in 1 mL of dry N,N-dimethylformamide. The salt was not very soluble in dimethylformamide (DMF). However, the mixture turned clear after diisopropylethylamine (55 μl, 0.31 mmol) was added. The mixture was stirred under nitrogen at room temperature for 18 hours. After removal of solvent, the crude material was loaded on a C-18 reverse phase flash column, and eluted with 20% $H_2O$ in MeOH to 10% $H_2O$ in MeOH. The pure fractions were collected and concentrated. An 81 mg colorless oily $N^1,N^4$-dioleyl-$N^1,N^4$-di-[2-hydroxy-3-(N-carboxamidine) aminopropyl]diaminobutane was obtained, which was converted to its TFA and HCL salts.

Synthesis of $N^1,N^4$-dioleyl-$N^1,N^4$-di-{2-hydroxy-3-[N-($N^I,N^{II},N^{III},N^{IV}$-butoxycarbonyl-spermine carboxamido)]aminopropyl}diaminobutane (VI)

Diisopropylcarbodiimide (5.32 mL, 34.0 mmol) was added dropwise to a solution of Boc-spermine acid (21.7 g, 33.5 mmol) and N-hydroxysuccinimide (NHS) (3.91 g, 34.0 mmol) in mixed solvents (100 mL of DMF and 100 mL of $CH_2Cl_2$) at room temperature. After stirring for 2.5 hours, a solution of $N^1,N^4$-dioleyl-$N^1,N^4$-di-[2-hydroxy-3-(N-aminopropyl)] diaminobutane (10 g, 13.6 mmol) in 40 mL of methylene chloride and DMF was added. The mixture was stirred for another 5 hours before quenching with 200 mL of a 2.5% sodium bicarbonate solution. An additional 300 mL of methylene chloride was added. The aqueous solution was extracted with 120 mL of methylene chloride three times. The combined organic solution was washed with water twice and dried over anhydrous magnesium sulfate. After concentration, a pale yellow oil was obtained. The crude material was purified with silica gel, eluting with 2% MeOH in $CH_2Cl_2$ to 5% MeOH in $CH_2Cl_2$. A total of 13.1 g of white solid $N^1,N^4$-dioleyl-$N^1,N^4$-di-{2-hydroxy-3-[N-($N^I,N^{II}, N^{III}, N^{IV}$-butoxycarbonylspermine carboxamido)]aminopropyl}di-aminobutane was obtained.

Synthesis of $N^1,N^1$-dioleyl-$N^1,N^1$-di-[2-hydroxy-3-(N-spermine carboxamido)-aminopropyl]-diaminobutane (VII)

100 mL of a solution of 4.0 M hydrogen chloride in 1,4-dioxane was added to a solution of $N^1,N^4$-dioleyl-$N^1,N^4$-di-{2-hydroxy-3-[N-($N^I,N^{II},N^{III},N^{IV}$-butoxycarbonyl-spermine carboxamido)]aminopropyl}diaminobutane (11.8 g, 5.92 mmol) in 100 mL of 1,4-dioxane at room temperature. The reaction mixture turned cloudy 10 minutes after addition of the acid. After 2,5 hours of stirring at room temperature, the excess acid and solvent was removed. The residue was dried for at least 5 hours over vacuum before being loaded on a C-18 reverse phase flash column. The column was eluted starting with 25% $H_2O$ in MeOH, then 20%, and then 17%. Pure fractions were collected and concentrated. A 3.06 g colorless solid $N^1,N^4$-dioleyl-$N^1,N^4$-di-[2-hydroxy-3-(N-spermine carboxamido)-aminopropyl]-diaminobutane was obtained.

The following compounds were synthesized using the protocol described above starting with the requisite diamine and long chain acyl chloride:

$N^1,N^4$-dimyristyl-$N^1,N^4$-di-[2-hydroxy-3-(N-sperminecarboxamido)-aminopropyl]-diaminobutane;

$N^1,N^4$-dipalmityl-$N^1,N^4$-di-[2-hydroxy-3-(N-sperminecarboxamido)-aminopropyl]-diaminobutane;

$N^1,N^4$-dipalmitolyl-$N^1,N^4$-di-[2-hydroxy-3-(N-sperminecarboxamido)-aminopropyl]-diaminobutane;

$N^1,N^4$-distearyl-$N^1,N^4$-di-[2-hydroxy-3-(N-sperminecarboxamido)-aminopropyl]-diaminobutane;

$N^1,N^4$-dilauryl-$N^1,N^4$-di-[2-hydroxy-3-(N-sperminecarboxamido)-aminopropyl]-diaminobutane;

$N^1,N^8$-dimyristyl-$N^1,N^8$-di-[2-hydroxy-3-(N-sperminecarboxamido)-aminopropyl]-Jeffamine;

$N^1,N^8$-dipalmityl-$N^1,N^8$-di-[2-hydroxy-3-(N-sperminecarboxamido)-aminopropyl]-Jeffamine;

$N^1,N^8$-dipalmitolyl-$N^1,N^8$-di-[2-hydroxy-3-(N-sperminecarboxamido)-aminopropyl]-Jeffamine;

$N^1,N^8$-distearyl-$N^1,N^8$-di-[2-hydroxy-3-(N-sperminecarboxamido)-aminopropyl]-Jeffamine;

$N^1,N^8$-dilauryl-$N^1,N^8$-di-[2-hydroxy-3-(N-sperminecarboxamido)-aminopropyl]-Jeffamine;

$N^1,N^8$-dioleyl-$N^1,N^8$-di-[2-hydroxy-3-(N-sperminecarboxamido)-aminopropyl]-Jeffamine;

$N^1,N^2$-dimyristyl-$N^1,N^2$-di-[2-hydroxy-3-(N-sperminecarboxamido)-aminopropyl]-diaminoethane;

$N^1,N^2$-dipalmityl-$N^1,N^2$-di-[2-hydroxy-3-(N-sperminecarboxamido)-aminopropyl]-diaminoethane;

$N^1,N^2$-dipalmitolyl-$N^1,N^2$-di-[2-hydroxy-3-(N-sperminecarboxamido)-aminopropyl]-diaminoethane;

$N^1,N^2$-distearyl-$N^1,N^2$-di-[2-hydroxy-3-(N-sperminecarboxamido)-aminopropyl]-diaminoethane;

$N^1,N^2$-dilauryl-$N^1,N^2$-di-[2-hydroxy-3-(N-sperminecarboxamido)-aminopropyl]-diaminoethane;

$N^1,N^2$-dioleyl-$N^1,N^2$-di-[2-hydroxy-3-(N-sperminecarboxamido)-aminopropyl]-diaminoethane.

Synthesis of dihydroxy-dioleyl-disperminecarboxamido spermine and analogs (Scheme 1)

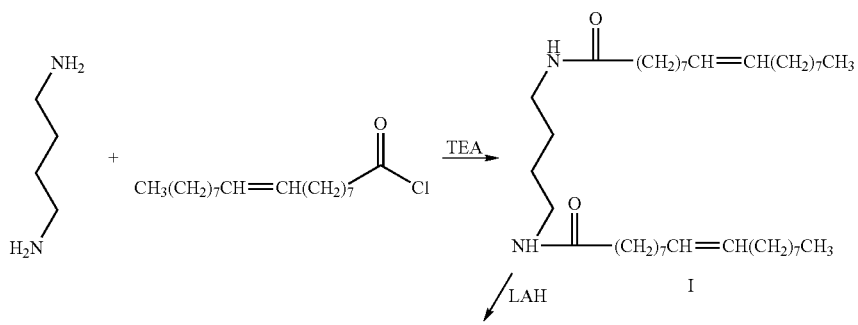

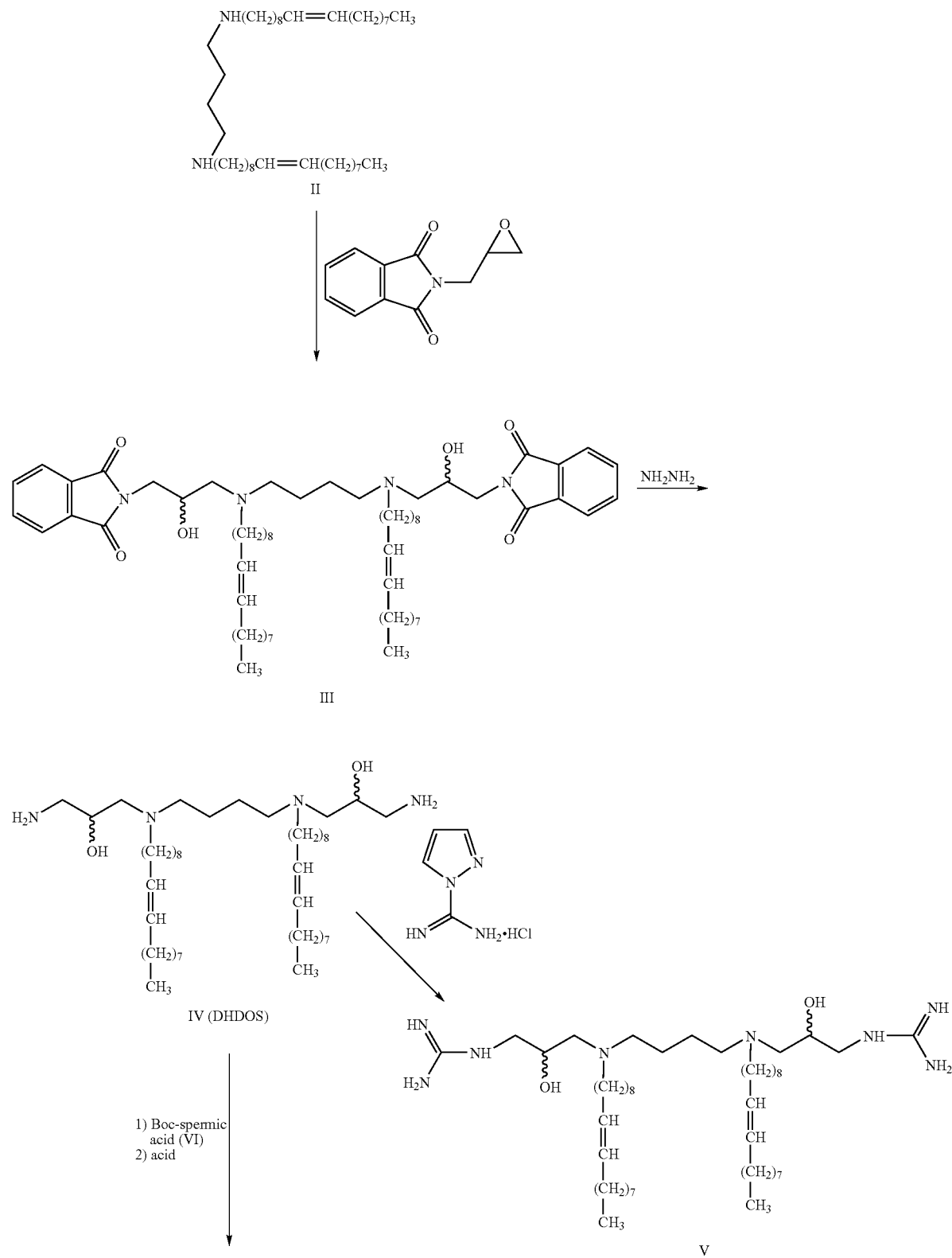

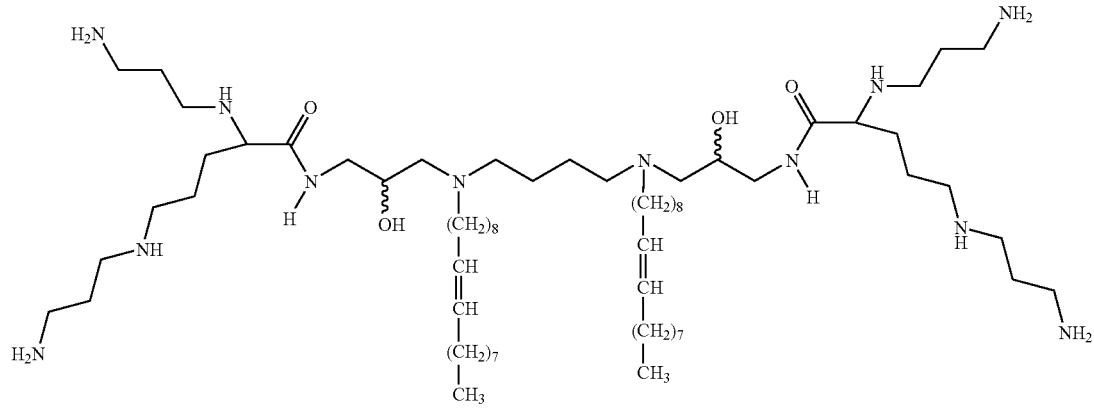

VII

EXAMPLE 2

Synthesis of N¹,N¹-dioleyl-N¹,N¹-di-3-cyanopropyl-diaminobutane (VIII)

Acrylonitrile (0.43 mL, 6.53 mmol) was added dropwise to a solution of $N^1,N^4$-dioleyl-diaminobutane (1.8 g, 3.06 mmol) in 20 mL of ethanol at room temperature. The mixture was stirred for 30 hours. All starting materials were converted to product as confirmed by TLC analysis. The crude material was purified using flash chromatography with a silica gel (1% MeOH in $CH_2Cl_2$). A clear oil was obtained at high yield.

Synthesis of $N^1,N^4$-dioleyl-$N^1,N^4$-di-3-(aminopropyl)-diaminobutane (IX)

A solution of LAH (9.2 mL, 1 M in ether, 9.2 mmol) was slowly added to a solution of $N^1,N^4$-dioleyl-$N^1,N^4$-di-3-cyanopropyl-diaminobutane (2.12 g, 3.05 mmol) in 15 mL of anhydrous diethyl ether at 0° C. After addition, the mixture was stirred at room temperature for 20 hours. All starting material was consumed. The reaction mixture was quenched with a 1 N NaOH solution at 0° C. After stirring 2 hours at room temperature, the mixture was extracted with diethyl ether three times. The combined ether solutions were concentrated and dried over vacuum for three hours. An oily $N^1,N^4$-dioleyl-$N^1,N^4$-di-3-(aminopropyl)diaminobutane was obtained at high yield.

Synthesis of $N^1,N^4$-dioleyl-$N^1,N^4$-di-[3-(N-spermine carboxamido)aminopropyl]-diaminobutane (XI)

The procedure for making $N^1,N^4$-dioleyl-$N^1,N^4$-di-[2-hydroxy-3-(N-spermine carboxamido)-aminopropyl]-diaminobutane described above was followed.

Synthesis of dioleyl-disperminecarboxamido spermine and analogs (Scheme 2)

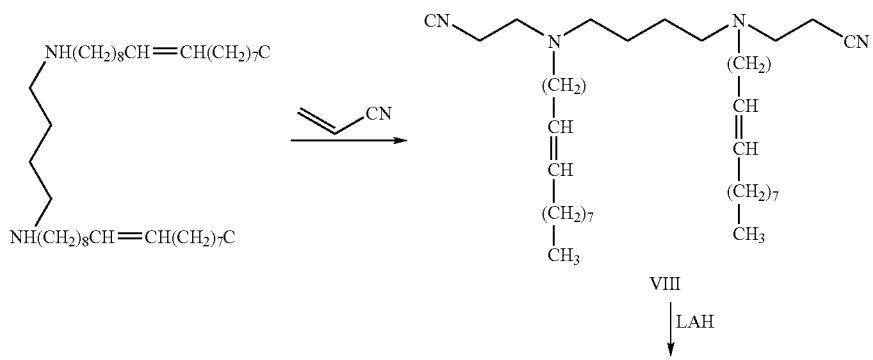

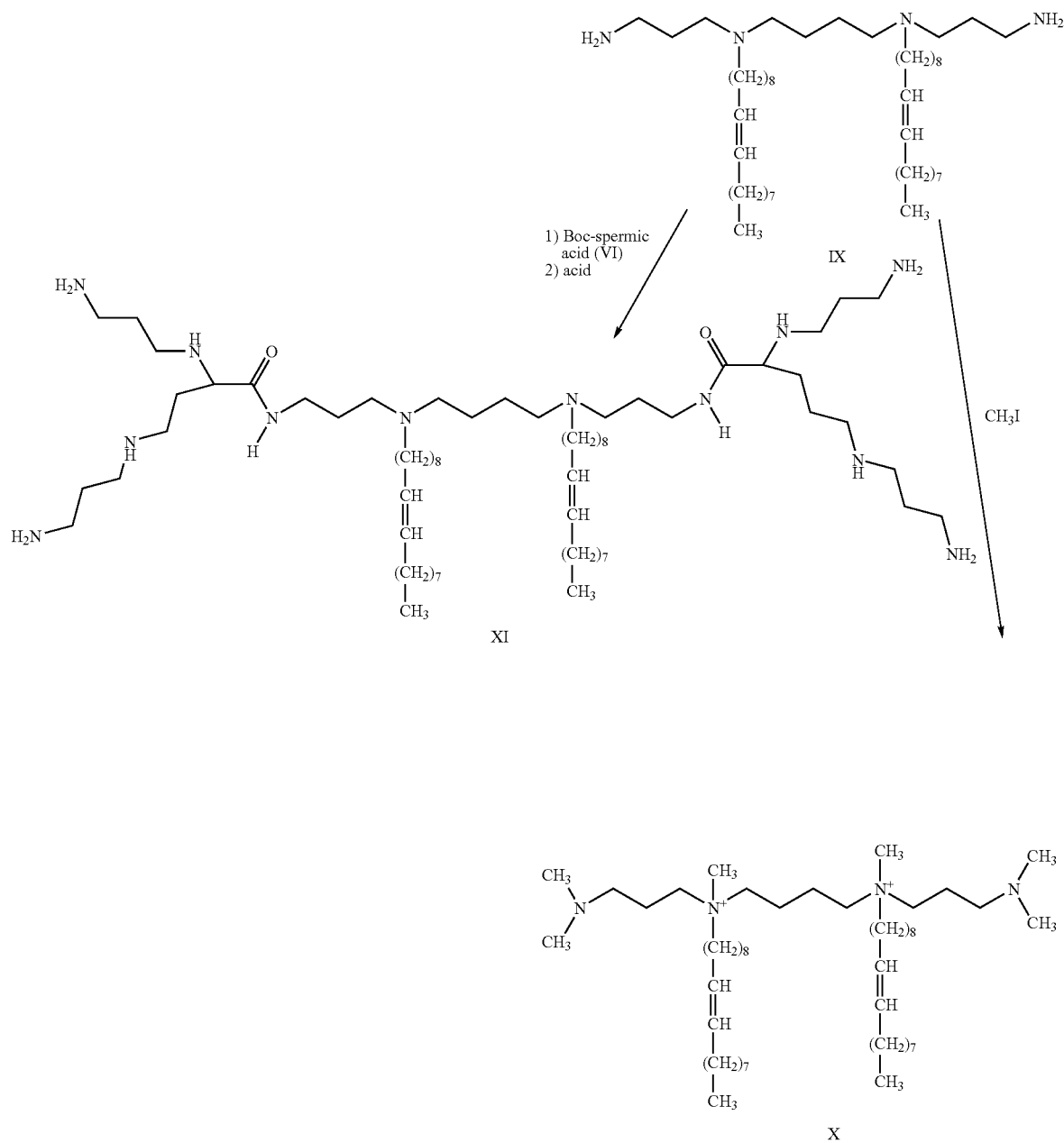
EXAMPLE 3
Synthesis of Cholesterol Analogs
The cholesterol analogs can be synthesized by using the scheme given below (Scheme 3). Jeffamine is alkylated with cholestryl chloride to provide the dicholestryl jefamine analog (XII). Further alkylation with the epoxide phthalamide (XIII) and deblocking with hydrazine gives the compound of the invention (XIV).

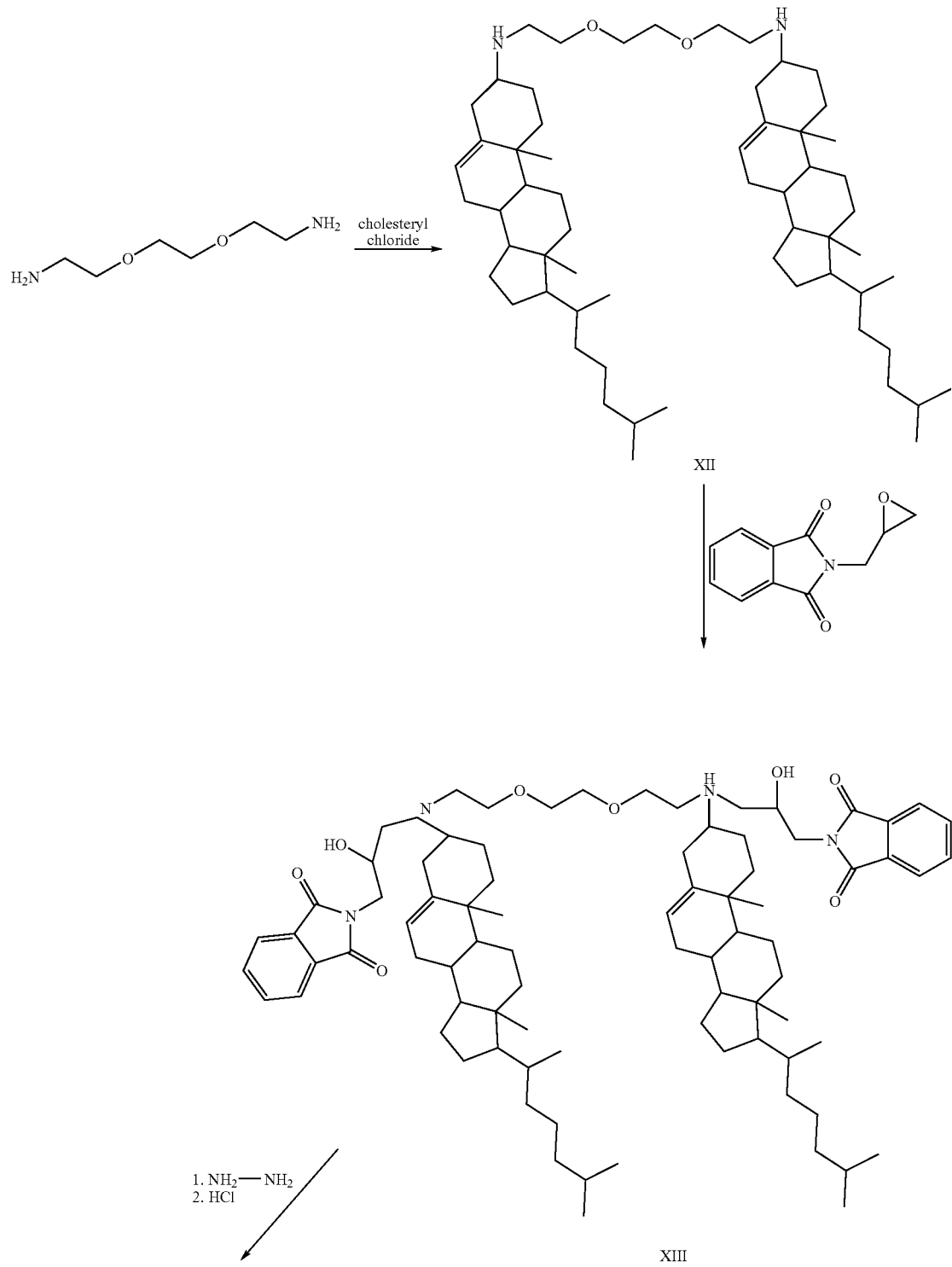

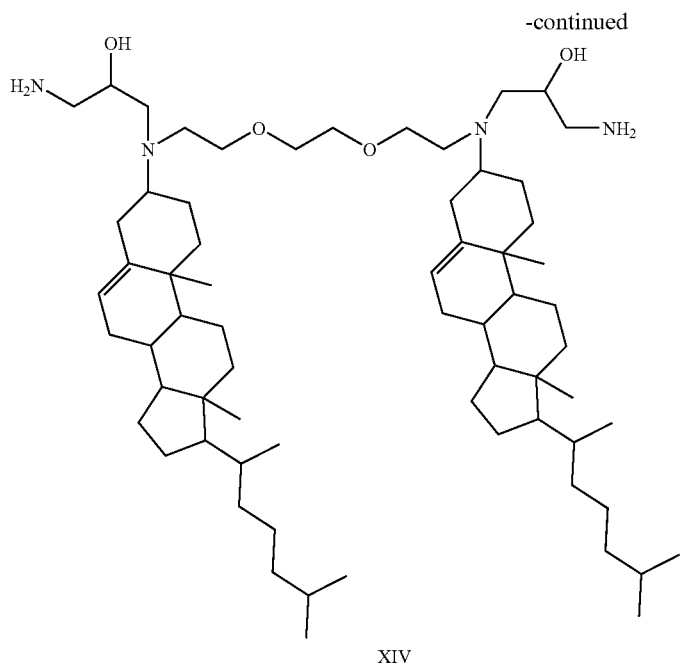

XIV

EXAMPLE 4

Synthesis of Monoalkyl Analogs

When monoalkyl analogs are desired, the above Scheme 1 can be modified such that one of the amines in the starting material is protected before the acylation step. Thus, trityl-protected diaminobutane (XV) is acylated with alkanoyl chloride (e.g., oleoyl chloride) followed with LAH reduction to obtain compound XVIII. The amine is then alkylated with the desired phthalamide epoxide to obtain compound XVIII. Removing the phthalamide using hydrazine renders the desired amine XIX. (See Scheme 4).

Synthesis of monoalkyl analogs (Scheme 4):

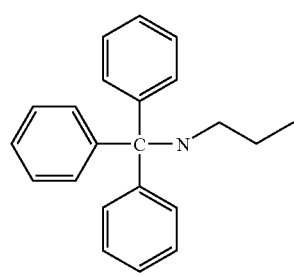

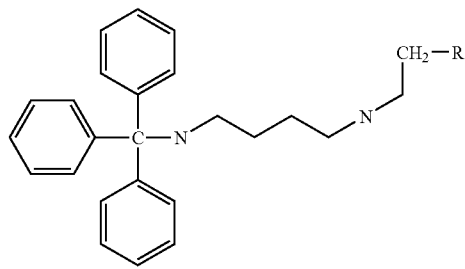

wherein R is a C$_8$–C$_{22}$ alkyl group

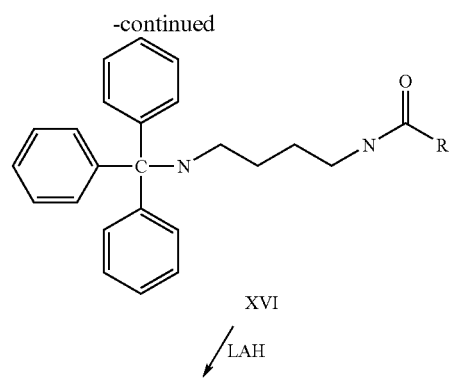

XVI

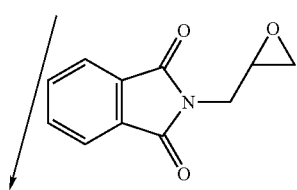

XVII

-continued

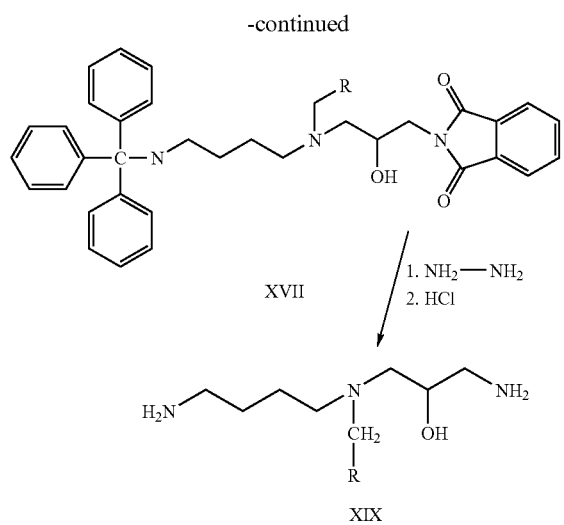

XVII

1. NH₂—NH₂
2. HCl

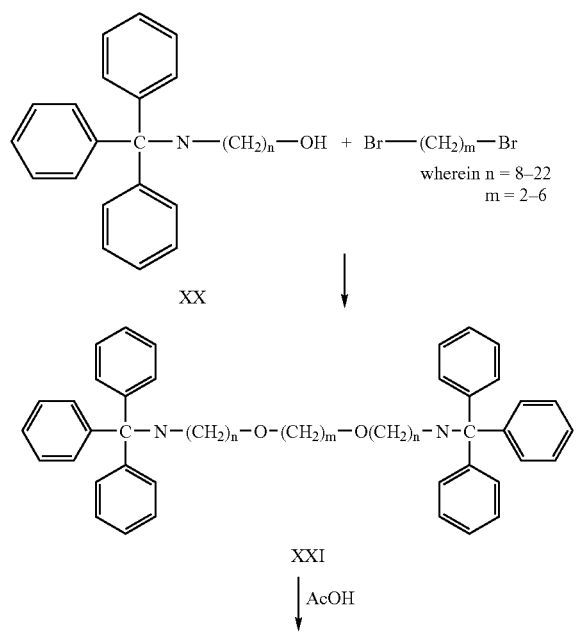

XIX

EXAMPLE 5

Synthesis of Cyclic Analogs

The following scheme (Scheme 5) can be used to make the cyclic analogs. Trityl protected amino alcohol (XX) with the desired chain is alkylated using dibromoalkyl (e.g., dibromobutane). The trityl is removed from the desired dimer (XXI) and acylated using diacyl chlorides (e.g., succinyl chloride). The amide (XXIII) is then reduced with LAH and alkylated using the desired phthalamide epoxide. Removal of the phthalamide gives the desired compound of the invention.

Synthesis of cyclic analogs (Scheme 5):

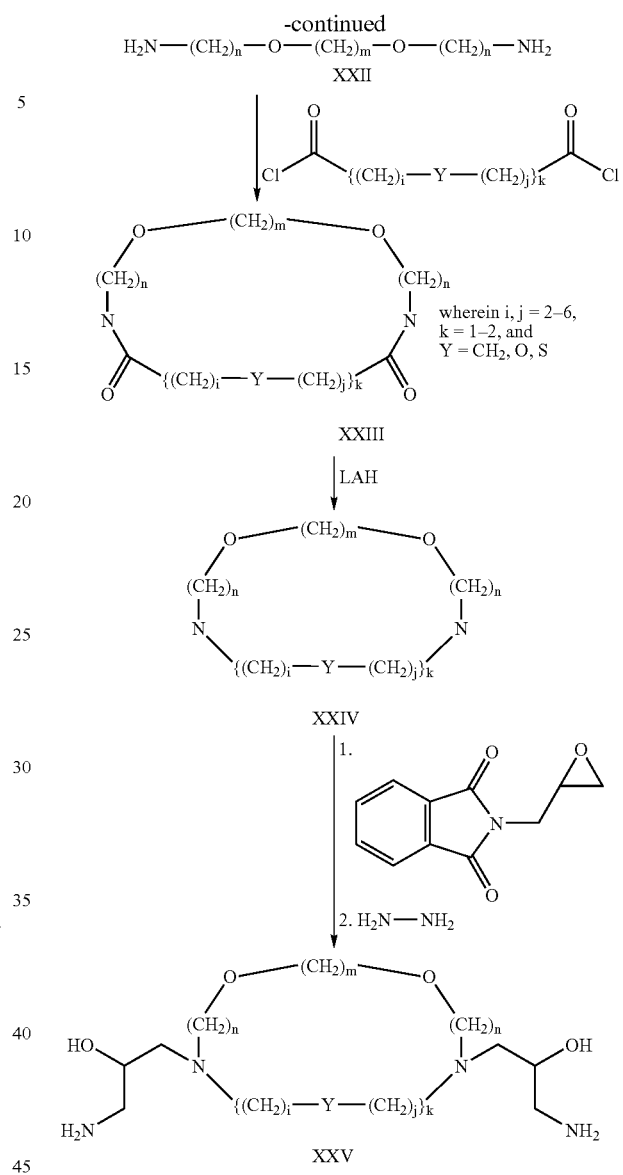

EXAMPLE 6

Synthesis of Polymeric Analogs

Polymeric analogs of the present invention can be synthesized by using polymeric amines such as PEI as starting material or dendrimeric polyamines. For example, PEI can be acylated with alkyloyl chloride (e.g., oleoyl chloride) and the acylated PEI can then be reduced with lithium aluminum hydride to obtain compounds of the invention.

Although the above methods exemplifies the synthesis of specific compounds, the reaction schemes provide a general method for preparing a variety of compounds according to the present invention. Those of ordinary skill in the art will appreciate that alternate methods and reagents other than those specifically detailed herein can be employed or readily adapted to produce compounds of the invention.

The compounds of the present invention can be used in the same manner as are prior art compounds such as DOTMA, DOTAP, DOGS, DOSPA and the like. Methods for incorporating such cationic lipids into lipid aggregates are well-known in the art. Representative methods are disclosed by Felgner, et al., supra; Eppstein et al. supra; Behr et al. supra; Bangham, A. et al. (1965) M. Mol. Biol. 23:238–252; Olson, F. et al. (1979) Biochim. Biophys. Acta 557:9–23; Szoka, F. et al. (1978) Proc. Natl. Acad. Sci. USA 75:4194–4198; Mayhew, E. et al. (1984) Biochim. Biophys. Acta 775:169–175; Kim, S. et al. (1983) Biochim. Biophys. Acta 728: 339–348; and Fukunaga, M. et al. (1984) Endocrinol. 115:757–761. Techniques for preparing lipid aggregates of appropriate size for use as delivery vehicles include sonication and freeze-thaw plus extrusion as perhaps the most commonly used. See, e.g., Mayer, L. et al. (1986) Biochim. Biophys. Acta 858:161–168. Microfluidization is used when consistently small (50–200 nm) and relatively uniform aggregates are desired (Mayhew, E., supra). Aggregates ranging from about 50 m to about 200 nm diameter are preferred; however, both larger and smaller sized aggregates are functional.

Methods of transfection and delivery of other compounds are well-known in the art. The compounds and compositions of the present invention yield lipid aggregates that can be used in the same processes used for other known transfection agents.

It will be readily apparent to those of ordinary skill in the art that a number of general parameters are important for optimal efficiency of transfection or delivery. These parameters include, for example, the cationic lipid concentration, the concentration of compound to be delivered, the number of cells transfected, the medium employed for delivery, the length of time the cells are incubated with the polyanion-lipid complex, and the relative amounts of cationic and non-cationic lipid. It may be necessary to optimize these parameters for each particular cell type. Such optimization is routine employing the guidance provided herein and knowledge generally available to the art.

It will also be apparent to those of ordinary skill in the art that alternative methods, reagents, procedures and techniques other than those specifically detailed herein can be employed or readily adapted to produce the liposomal precursors and transfection compositions of this invention. Such alternative methods, reagents, procedures and techniques are within the spirit and scope of this invention.

The use of representative compounds of the invention are further detailed by reference to the following examples. All abbreviations used herein are standard abbreviations in the art. Specific procedures not described in detail are either referenced or well-known in the art.

EXAMPLE 7

This example compares transfection of HEK-293 (human embryonic kidney-derived cell line), COS-7 (SV-40 transformed monkey cell line), CHO-K1 (Chinese Hamster Ovary-derived cell line), and HeLa (Human cervical carcinoma-derived cell line) cells with the β-galactosidase reporter plasmid DNA pCMV•SPORT-β-gal (LifeTechnologies, Rockville, Md.) using commercially available cationic lipid transfection reagents and the compounds of the present invention.

The cells were plated the day before transfection in 24-well tissue culture plates in a total volume of 0.4 ml DMEM (Dulbecco's Modified Eagle's Medium, Life Technologies, Rockville, Md.) culture medium containing a 1% non-essential amino acid (NEAA) solution (LifeTechnologies), and 10% FBS. For the HEK-293 and COS-7 cells, the tissue culture plates were pre-coated with Poly-L-Lysine to enhance cell attachment.

The next day, DNA-transfection reagent complexes were prepared as follows:

The cationic lipid reagents and DNA were diluted separately into 25 μl aliquots of serum-free DMEM, containing 1% NEAA. For LipofectAMINE PLUS, 7–14 μl of PLUS reagent was added to the DNA, mixed, and incubated for 15 minutes at room temperature. The diluted DNA was combined with the diluted lipid and incubated at room temperature for at least 15 minutes to allow the DNA and the lipid to form complexes. Following this incubation the complexes were added directly into the culture medium dropwise and mixed by rocking the culture plate back and forth. The cells were further incubated at 37° C. for a total of 24 hours to allow expression of the lacZ transgene encoded by the reporter plasmid, pCMV•SPORT-β-gal. At 24 hours post-transfection, the growth medium and transfection complexes were removed from the wells, and the cells in each well were rinsed briefly with 1 ml of D-PBS (Dulbecco's PBS, Life Technologies, Rockville, Md.). The cells in each well were lysed by the addition of 0.15 to 2.0 ml of 0.1% Tris, pH 8.0, containing 0.1 M Triton X-100. The plates were frozen at −80° C. for a minimum of 2 hours, and thawed at room temperature or 37° C. The thawed cell lysates were cleared by centrifugation and the supernatants were assayed for β-gal activity using the enzymatic substrate ONPG. The concentration of total protein in cell lysates was also determined using a Bradford assay (Bio-Rad Laboratories, Hercules Calif.). β-gal activity in transfected cell extracts was calculated against a standard curve and expressed as ng β-gal per surface area of issue culture plate (ng/cm$^2$) to reflect total activity per transfection, or as ng β-gal per μg of total protein (ng/μg) to reflect specific activity.

Figure 2:
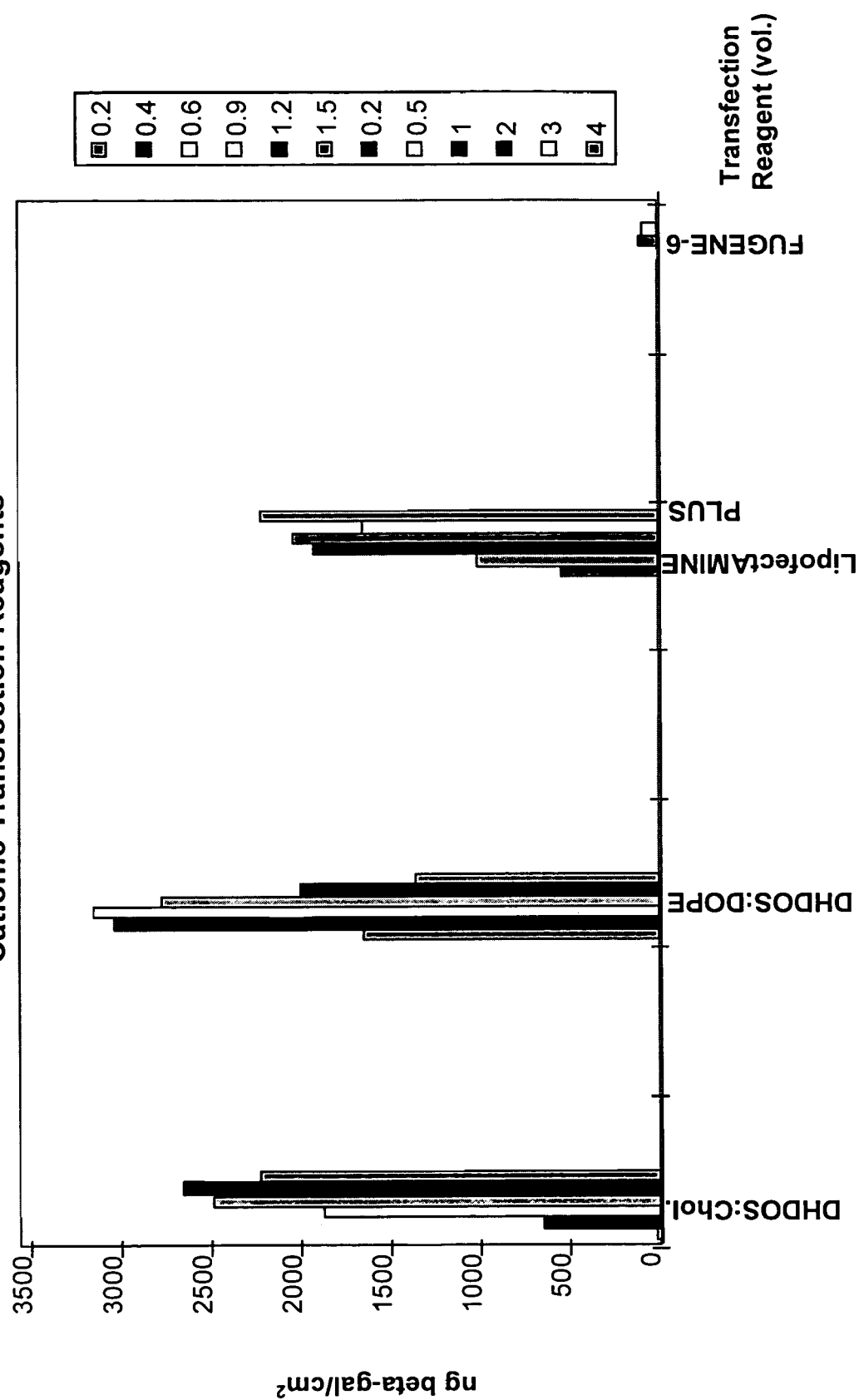
FIG. 2 is a graph showing transfection of COS-7 cells with cationic transfection reagents.
Figure 3:
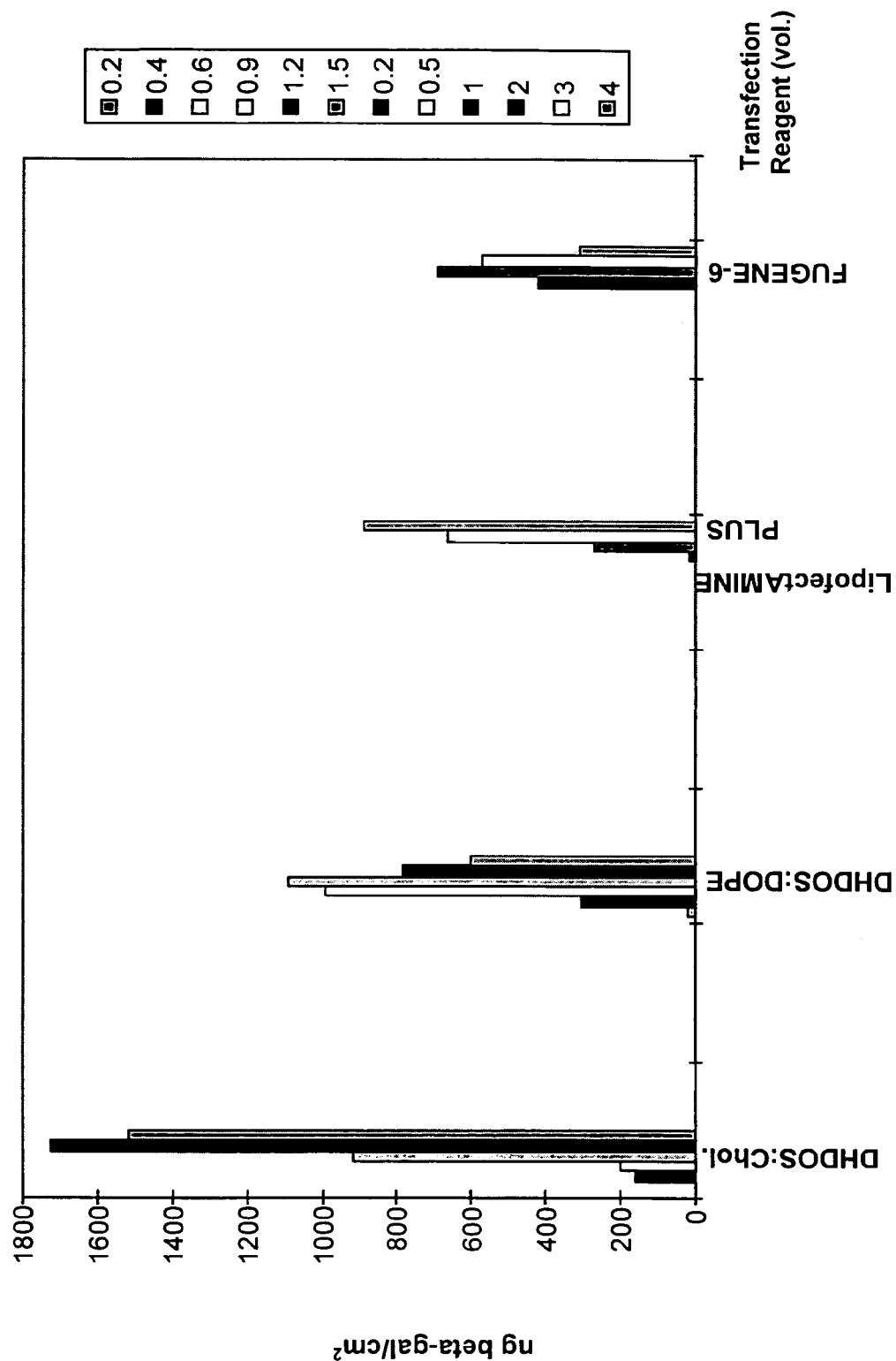
FIG. 3 is a graph showing transfection of CHO-K1 cells with cationic transfection reagents.
Figure 4:
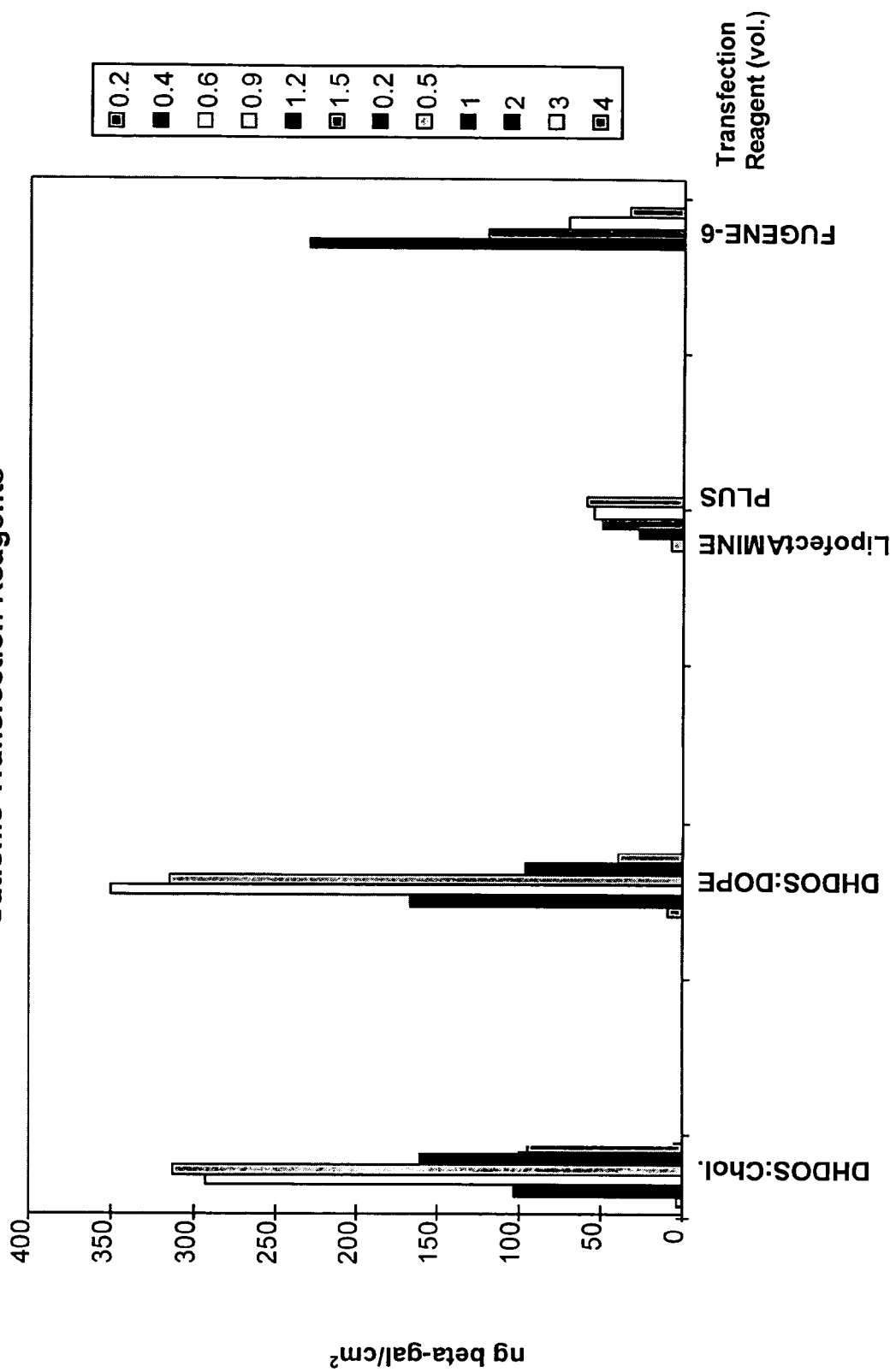
FIG. 4 is a graph showing transfection of HeLa cells with cationic transfection reagents.

HEK-293 (FIG. 1), COS-7 (FIG. 2), CHO-K1 (FIG. 3), and HeLa (FIG. 4) cells were transfected with 0.4 or 0.8 μg of pCMV-SPORT-β-gal DNA and 0.2 to 4.0 μl of transfection reagent. The transfection reagents tested were DHDOS (IV) formulated at 2 mg/ml with the neutral co-lipid, cholesterol (at a ratio of 1:15 (M/M) DHDOS to cholesterol); DHDOS formulated at 2 mg/ml with the neutral co-lipid DOPE (dioleyl phosphatidyl ethanolamine) (at a ratio of 1:1 (M/M) DHDOS to DOPE); LipofectAMINE PLUS (Life Technologies, Rockville Md.); and FuGENE™-6 (Boehringer Mannheim, Germany). DHDOS formulations were tested in the range of 0.2 to 1.5 μl; LipofectAMINE PLUS and FuGENE-6 were tested in the range of 0.2 to 4.0 μl. FuGENE-6 was used according to the manufacturer's recommended protocol. DHDOS and LipofectAMINE PLUS were used according to the above protocol. The data presented in the Figures are expressed as total activity (ng/cm$^2$) to better compare total expression from the transfected DNA. Only data with 0.8 μg of DNA is shown, since similar results were obtained with 0.4 and 0.8 μg of DNA.

EXAMPLE 8

Primary, passaged, normal human fibroblasts (NHFs) were plated in 96-well plates at a density of 1.6×10$^4$ cells per well and transfected the following day. Cells in each well were transfected with 40 ng pCMV-SPORT-β-gal DNA and 0.1 or 0.2 μl lipid. The DNA and lipid were diluted separately into 10 μl of DMEM. The DNA was either used alone or pre-mixed with PLUS, insulin, transferrin, or an integrin-targeting peptide prior to complexing with the lipid. After 15 minutes of complexing, the DNA-lipid was added to cells. Cells were assayed for β-gal activity as described above.

| | ACTIVITY (ng/βgal/cm²) | | | | |
|---|---|---|---|---|---|
| LIPID | DNA | DNA and PLUS* | DNA and IN- SULIN | DNA and TRANS- FERRIN | DNA and INTEGRIN- TARGETING PEPTIDE** |
| LipofectAMINE | 10.36 | 28.6 | ND | 17.4 | ND |
| Compound of Formula X 1:1.5 DOPE 1 mg/ml | ND | 37.8 | ND | ND | 40.9 |
| Compound of Formula VII 1:1 DOPE 2 mg/ml | 29.4 | 637.9 | 195.7 | 21.7 | 587.9 |

ND = no detectable activity
*PLUS Reagent is available from Life Technologies, Inc., Rockville, Maryland.
**Reference: S. L. HART, et al (1998), Human Gene Therapy, 9:575–585.

The results show that these cationic lipid formulations can deliver DNA molecules alone, but also that delivery, and ultimately gene expression, may be enhanced when the lipids are used in conjunction with peptides or proteins that bind DNA and/or act as ligands for cell surface receptors, or otherwise enhance cellular and/or nuclear uptake.

Having now fully described the present invention in some detail by way of illustration and examples for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A compound having the formula:

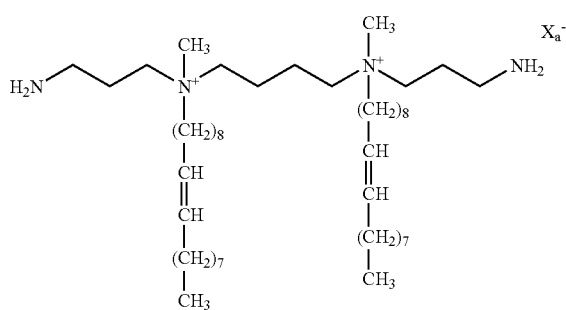

wherein
  $X^-$ is a physiologically acceptable anion; and a is the number of anions which is equal to the number of positive charges in the compound divided by the valence of the anion.

2. A compound having the formula:

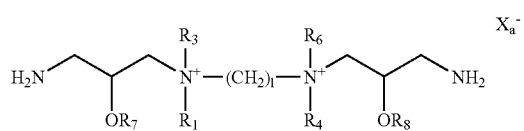

wherein
  $X^-$ is a physiologically acceptable anion;
  a is the number of anions which is equal to the number of positive charges in the compound divided by the valence of the anion;
  $R_1$, $R_3$, $R_4$, and $R_6$, independently of one another, are selected from the group consisting of H, an alkyl group, an alkenyl group, an alkynyl group, and an aryl group, wherein any one of $R_1$, $R_3$, $R_4$, and $R_6$ are optionally substituted by one or more of an alcohol, an amine, an amide, an ether, a polyether, a polyamide, an ester, a mercaptan, a urea, a thiourea, a guanidyl, or a carbamoyl group, and at least two of $R_1$, $R_3$, $R_4$, and $R_6$, are straight-chain, branched, or cyclic alkyl, alkynyl, or alkenyl or aryl groups having from 8 to 24 carbon atoms attached to each N and $R_1$, $R_3$, $R_4$ and $R_6$ may optionally be covalently linked with each other;
  $R_7$ and $R_8$ are independently H or a carbohydrate; and
  l is an integer from 1 to about 4.

3. The compound as claimed in claim 2, which is:

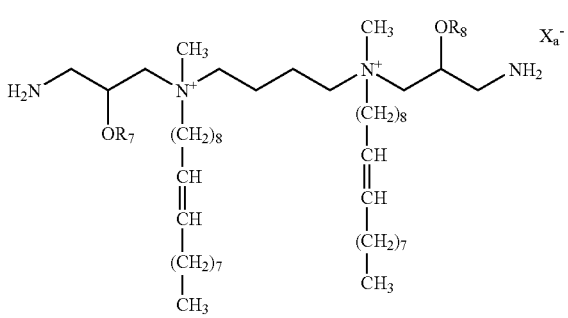

wherein $R_7$ and $R_8$ are independently H or a carbohydrate.

4. The compound as claimed in claim 3, wherein $R_7$ and $R_8$ are H.

5. A compound having the formula:

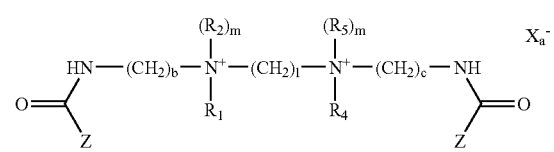

wherein
  $R_1$, $R_2$, $R_4$ and $R_5$, independently of one another, are selected from the group consisting of H, an alkenyl group, an alkynyl group, and an aryl group, and an alkyl group optionally substituted by one or more of an alcohol, an amine, an amide, an ether, a polyether, a polyamide, an ester, a mercaptan, a urea, a thiourea, a guanidyl, or a carbamoyl group, and at least two of $R_1$, $R_2$, $R_4$ and $R_5$ are a straight-chain, branched, or cyclic alkyl, alkenyl, alkynyl or aryl group having from about 8 to about 24 carbon atoms attached to each N;

Z is selected from the group consisting of spermiyl, spermidiyl, amino acid, peptidyl, diaminoalkyl, and polyamine;

$X^-$ is a physiologically acceptable anion;

m and n are 1;

l, b and c are integers independently selected from 1 to about 4; and a is the number of positive charges in the compound divided by the valence of the anion.

6. The compound as claimed in claim 5, which is:

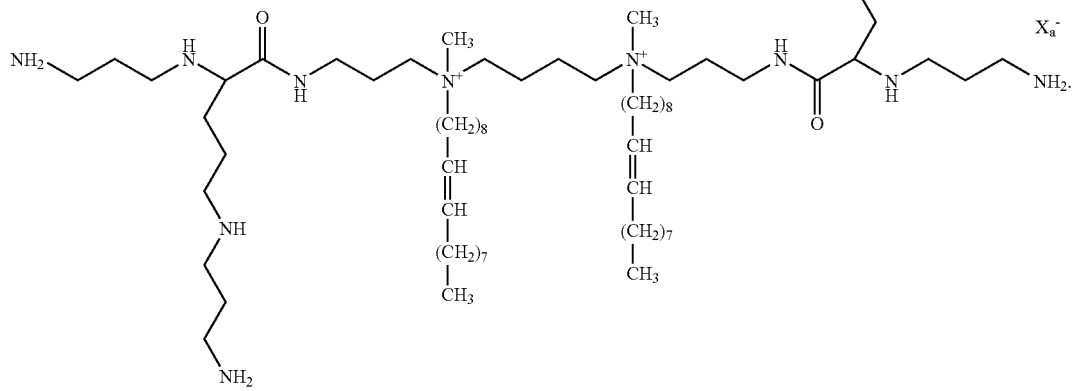

7. The compound which is:

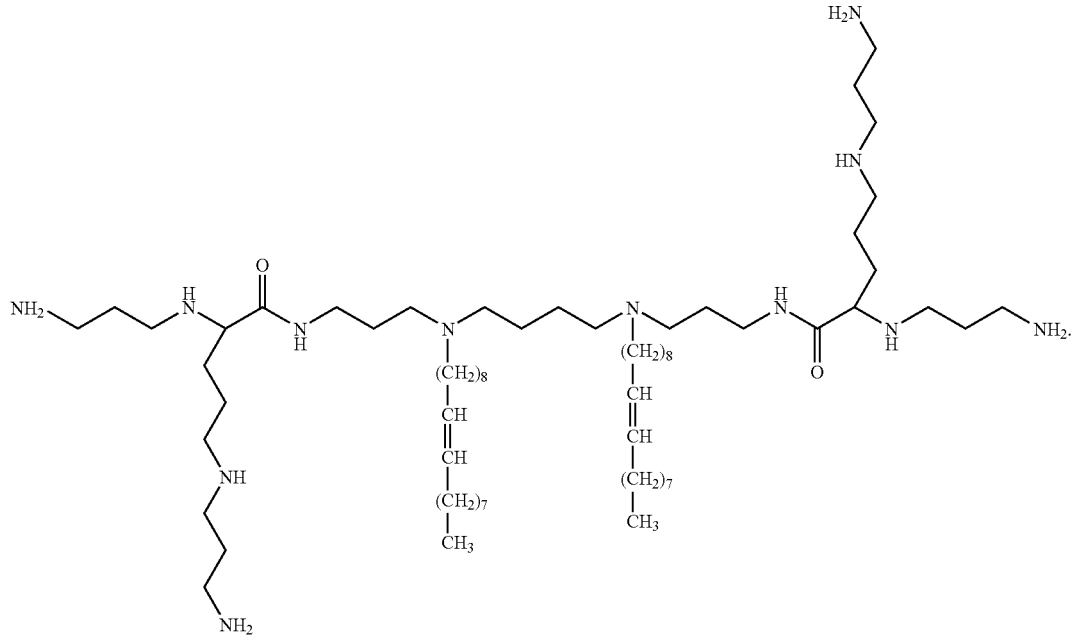

8. The compound which is:

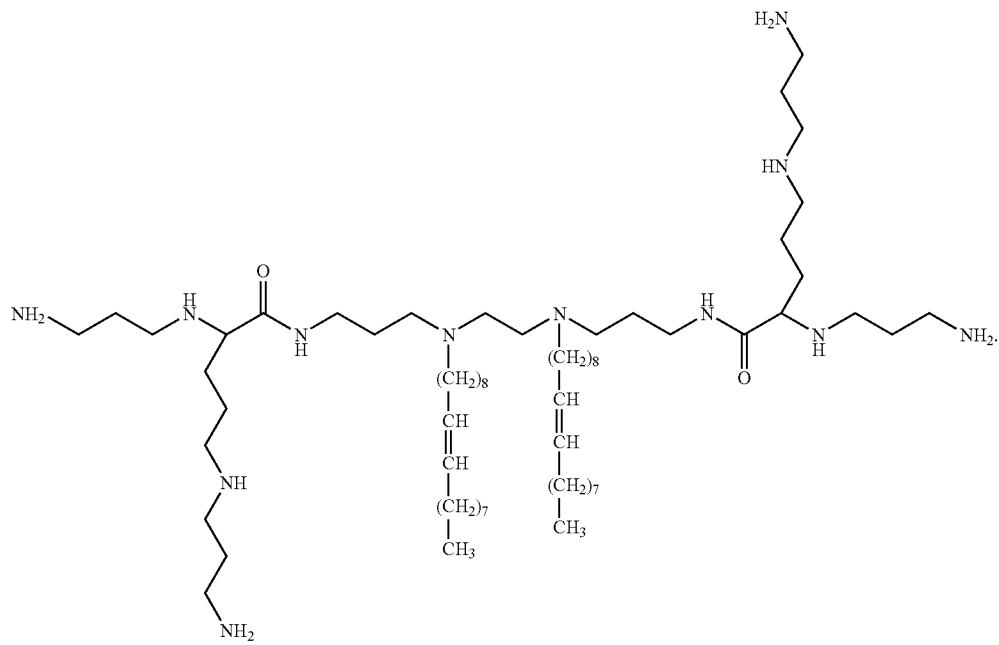

9. A compound having the formula:

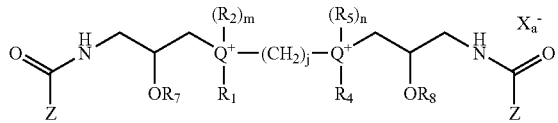

wherein

Q is N;

$X^-$ is a physiologically acceptable anion;

a is the number of anions which is equal to the number of positive charges in the compound divided by the valence of the anion;

$R_1$ and $R_4$, independently of one another, are selected from the group consisting of H, —$(CH_2)_p$—D—Z, an alkyl group, an alkyl ether group, an alkenyl group, an aryl group, and an alkyl or alkyl ether group substituted by one or more of an alcohol, an aminoalcohol, an amine, an amide, an ether, a polyether, a polyamide, an ester, a mercaptan, an alkylthio, a urea, a thiourea, a guanidyl, or a carbamoyl group, $R_1$ and $R_4$ may optionally be covalently linked with each other, to form a cyclic moiety; at least one of $R_1$ and $R_4$ is a straight-chain, branched, or cyclic alkyl, alkenyl, or alkynyl group having from 8 to 24 carbon atoms;

$R_2$ and $R_5$, independently of one another, are selected from the group consisting of H, an alkenyl group, an alkynyl group, an aryl group, and an alkyl group optionally substituted by one or more of an alcohol, an amine, an amide, an ether, a polyether, a polyamide, an ester, a mercaptan, a urea, a thiourea, a guanidyl, or a carbamoyl group;

Z is selected from the group consisting of spermiyl, spermidyl, aminoacid, peptidyl, diaminoalkyl, and polyamine;

D is N, O, S, or a bond;

$R_7$ and $R_8$ independently are H or a carbohydrate;

m and n are 1;

l is an integer selected from 1 to about 4; and p is an integer from 1 to about 10.

10. The compound as claimed in claim 9 wherein $R_7$ and $R_8$ are H.

11. The compound as claimed in claim 9 which is:
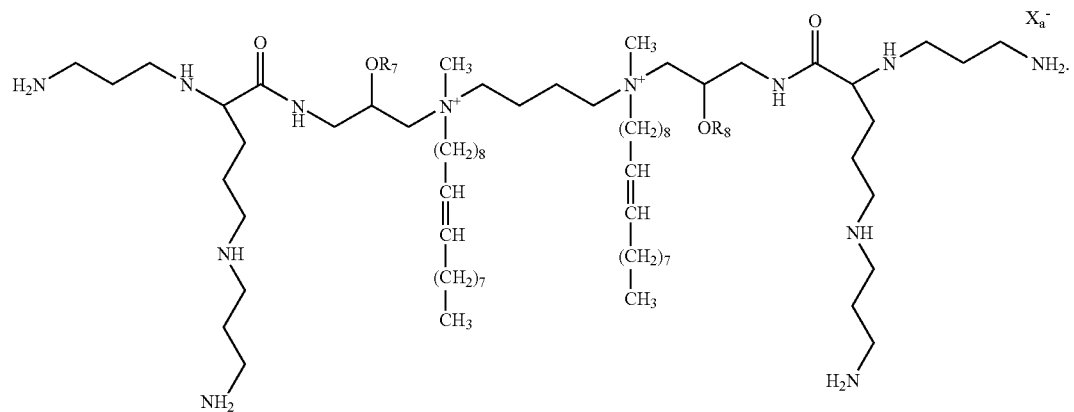
12. The compound according to claim 11, wherein $R_7$ and $R_8$ are H.
13. The compound which is
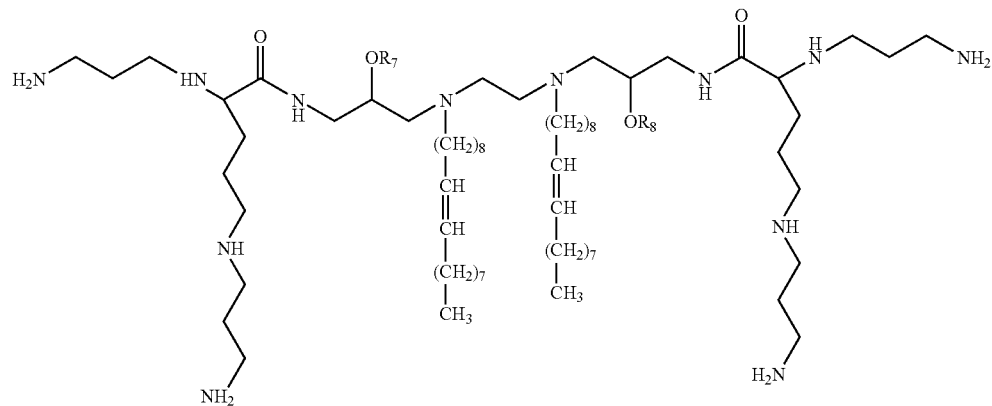
wherein $R_7$ and $R_8$ independently are H or a carbohydrate.
14. The compound as claimed in claim 13, wherein $R_7$ and $R_8$ are H.
15. The compound which is
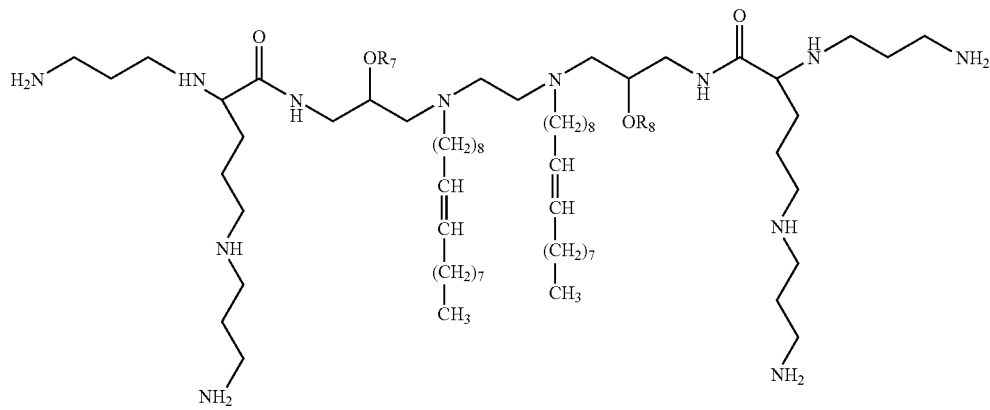
wherein $R_7$ and $R_8$ independently are H or a carbohydrate.

16. The compound as claimed in claim 15, wherein $R_7$ and $R_8$ are H.

17. A compound having the formula:

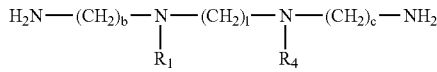

wherein each of $R_1$ and $R_4$ is a —$(CH_2)_8$—CH=CH—$(CH_2)_7$—$CH_3$ group; and l, b, and c are integers independently selected from 1 to about 4.

18. The compound as claimed in claim 17, which is:

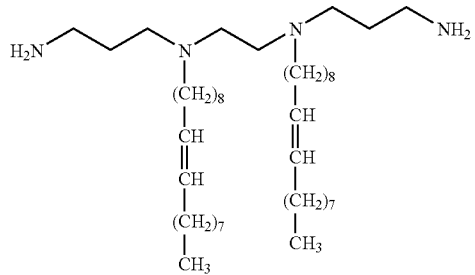

19. The compound as claimed in claim 17, which is:

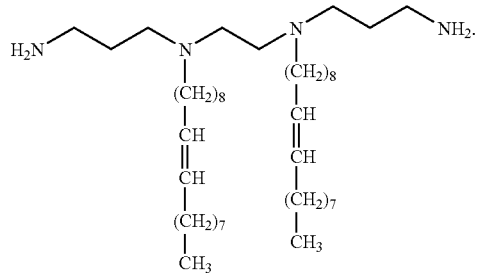

20. A compound having the formula:

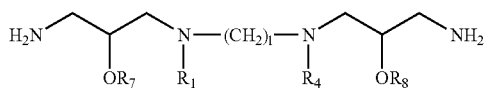

wherein
each of $R_1$ and $R_4$ is a straight-chain, branched, or cyclic alkenyl, or alkynyl group having 8 to 24 carbon atoms;
$R_7$ and $R_8$ are independently H or a carbohydrate; and
l is an integer independently selected from 1 to 4.

21. The compound as claimed in claim 20, which is:

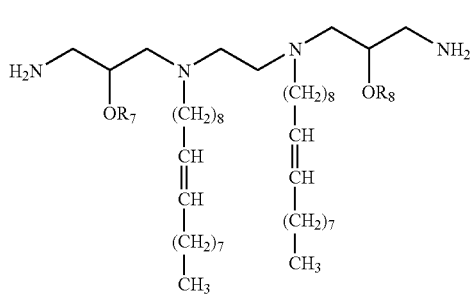

wherein $R_7$ and $R_8$ are independently H or a carbohydrate.

22. The compound as claimed in claim 21, wherein $R_7$ and $R_8$ are H.

23. The compound as claimed in claim 20, which is:

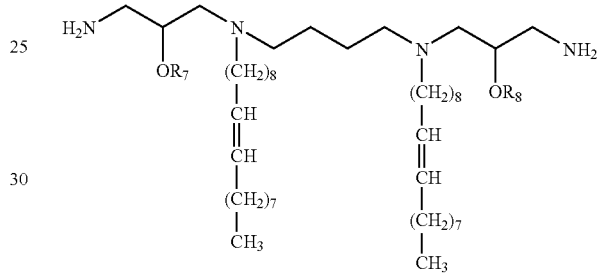

wherein $R_7$ and $R_8$ are independently H or a carbohydrate.

24. The compound as claimed in claim 23, wherein $R_7$ and $R_8$ are H.

25. A compound having the formula:

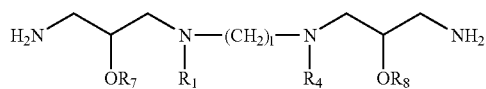

wherein
l is 4,
$R_1$ and $R_4$ are straight-chain alkyl groups having 14 or 16 carbon atoms, and
$R_7$ and $R_8$ are independently selected from H or a carbohydrate.

26. The compound as claimed in claim 25, wherein $R_7$ and $R_8$ are both H.

27. A compound having the formula:

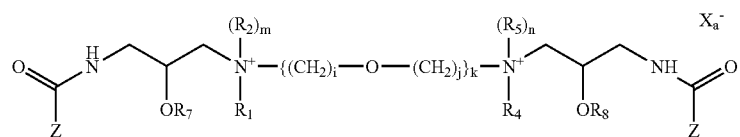

wherein
Z is selected from the group consisting of amine, spermiyl, carboxyspermiyl, guanidyl, spermidinyl, putricinyl, diaminoalkyl, pyridyl, piperidinyl, pyrrolidinyl, polyamine, amino acid, peptide and protein;
D is N, O, S, or a bond;
p is an integer from 1 to about 10;
$R_1$ and $R_4$, independently of one another, are selected from the group consisting of H, —$(CH_2)_p$—D—Z, an alkyl group, an alkenyl group, an aryl group, an alkynyl group, and an alkyl ether group wherein any one of $R_1$, and $R_4$ are optionally substituted by one or more of an alcohol, an aminoalcohol, an amine, an amide, an ether, a polyether, a polyamide, an ester, a mercaptan, an alkylthio, a urea, a thiourea, a guanidyl, or a carbamoyl group, $R_1$, and $R_4$ may optionally be covalently linked with each other to form a cyclic moiety; and at least one of $R_1$ and $R_4$ is a straight-chain, branched, or cyclic alkyl, alkenyl, alkynyl or aryl group having from 8 to about 24 carbon atoms; and
$R_2$ and $R_5$, independently of one another, are selected from the group consisting of H, an alkenyl group, an alkynyl group, an aryl group and an alkyl group optionally substituted by one or more of an alcohol, an amine, an amide, an ether, a polyether, a polyamide; an ester, a mercaptan, a urea, a thiourea, a guanidyl and a carbamoyl group;

$R_7$ and $R_8$ are independently H or a carbohydrate;
$X^-$ is a physiologically acceptable anion;
a is the number of positive charges in the compound divided by the valence of the anion;
m and n are 1;
i and j are integers selected from 2 to about 3; and
k is an integer selected from 1 to about 3.

28. A compound having the formula:

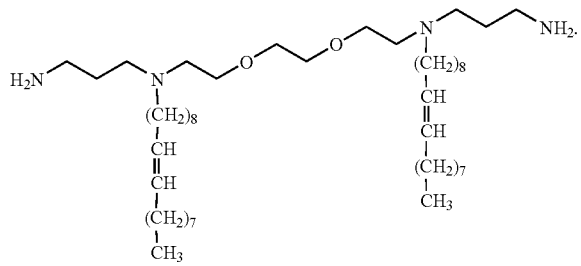

29. A compound having the formula:

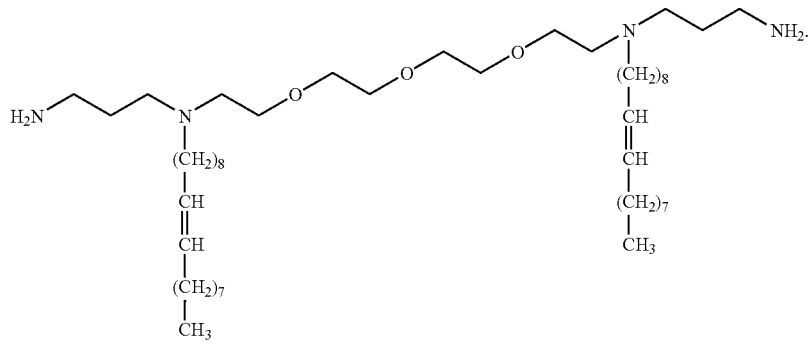

30. A compound having the formula:

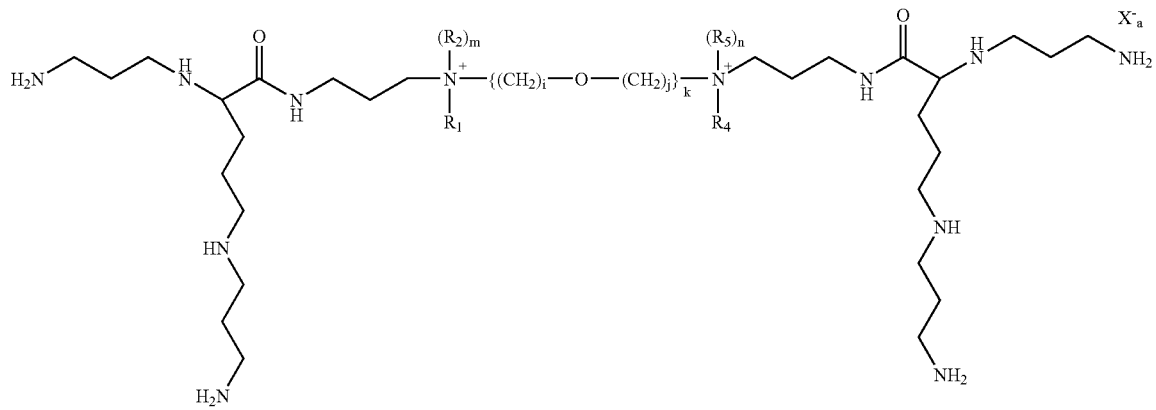

wherein
- each of $R_1$ and $R_4$ is a straight-chain, branched, or cyclic alkenyl, alkynyl or aryl group having from about 8 to about 24 carbon atoms;
- $R_2$ and $R_5$, independently of one another, are selected from the group consisting of a, an alkenyl group, an aryl group, and an alkyl group optionally substituted by one or more of an alcohol, an amine, an amide, an ether, a polyether, a polyamide, an ester, a mercaptan, a urea, a thiourea, a guanidyl, or a carbamoyl group;
- $X^-$ is a physiologically acceptable anion;
- a is the number of positive charges in the compound divided by the valence of the anion;
- m and n are 1;
- i and j are integers selected from about 2 to about 3; and
- k is an integer selected from 1 to about 3.

31. The compound which is:

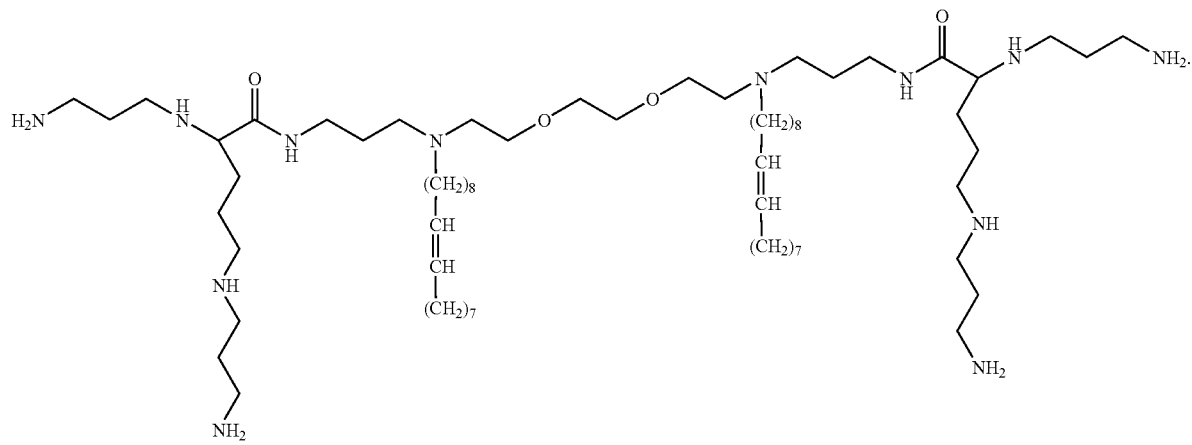

32. A compound having the formula:

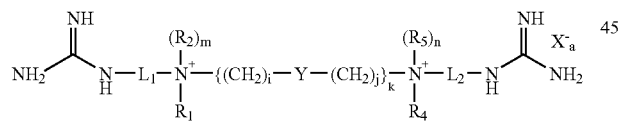

wherein
- each of $R_1$ and $R_4$ is a straight-chain, branched, or cyclic alkenyl, alkynyl or aryl group having from about 8 to about 24 carbon atoms;
- $R_2$ and $R_5$, independently of one another, are selected from the group consisting of an alkenyl group, an aryl group, and an alkyl group optionally substituted by one or more of an alcohol, an amine, an amide, an ether, a polyether, a polyamide, an ester, a mercaptan, a urea, a thiourea, a guanidyl, or a carbamoyl group;
- m and n are 1;
- i and j are integers from about 2 to about 3;
- k is an integer from 1 to about 3;
- $L_1$ and $L_2$, independently from one another, are an alkylene or an alkylene ether; and
- Y is selected from the group consisting of $CH_2$, O, S and NH.

33. The compound which is:

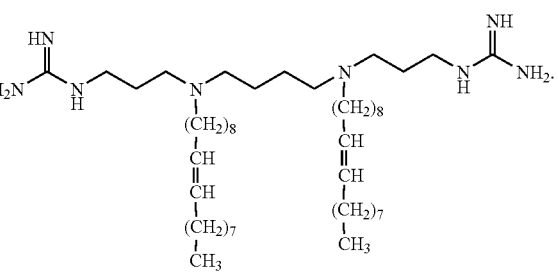

34. A compound having the formula:

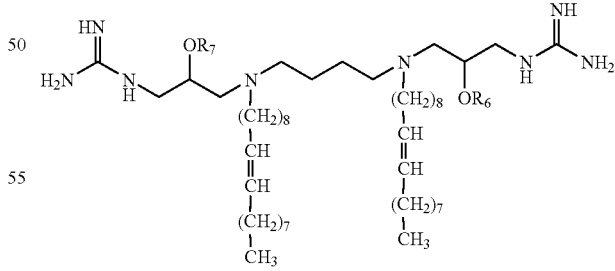

wherein $R_7$ and $R_8$ are independently H or a carbohydrate.

35. The compound as claimed in claim 34, wherein $R_7$ and $R_8$ are H.

36. A compound having the formula:

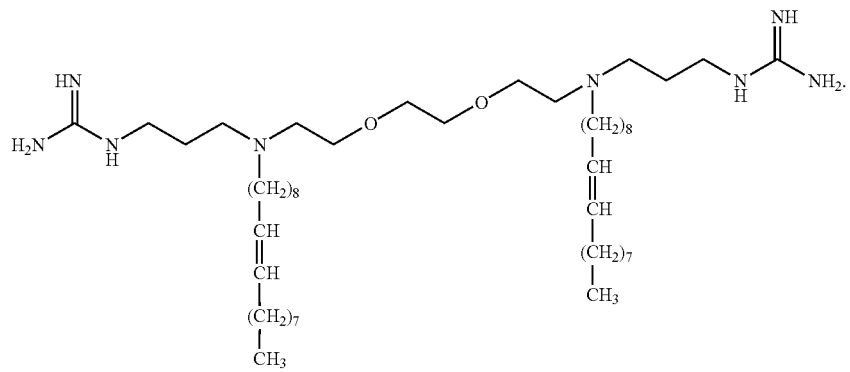

37. A compound having the formula:

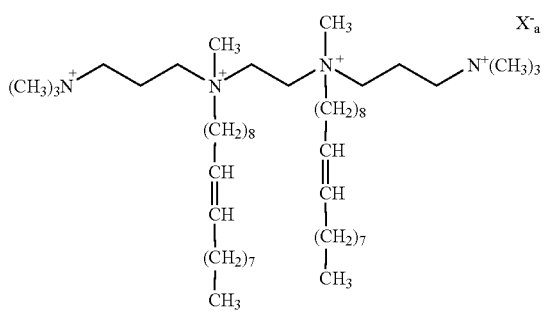

wherein

X⁻ is a physiologically acceptable anion; and a is the number of positive charges in the compound divided by the valence of the anion.

38. A compound having the formula:

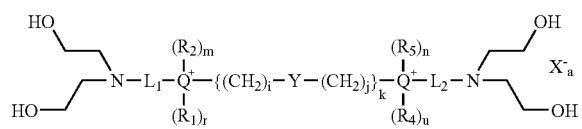

wherein

Q is N;

X⁻ is a physiologically acceptable anion;

a is the number of anions which is equal to the number of positive charges in the compound divided by the valence of the anion;

$R_1$ and $R_4$, independently of one another, are selected from the group consisting of H, —$(CH_2)_p$—D—Z, an alkyl group, an alkyl ether group, an alkenyl group, an aryl group, and an alkyl or alkyl ether group substituted by one or more of an alcohol, an aminoalcohol, an amine, an amide, an ether, a polyether, a polyamide, an ester, a mercaptan, an alkylthio, a urea, a thiourea, a guanidyl, or a carbamoyl group, $R_1$ and $R_4$ may optionally be covalently linked with each other, to form a cyclic moiety; and at least one of $R_1$ and $R_4$ is a straight-chain, branched, or cyclic alkyl, alkenyl, alkynyl or aryl group having from 8 to about 24 carbon atoms;

$R_2$ and $R_5$, independently of one another, are selected from the group consisting of H, an alkenyl group, an aryl group, and an alkyl group optionally substituted by one or more of an alcohol, an amine, an amide, an ether, a polyether, a polyamide, an ester, a mercaptan, a urea, a thiourea, a guanidyl, or a carbamoyl group;

Z is selected from the group consisting of amine, spermiyl, spermidyl, carboxyspermiyl, guanidyl, spermidinyl, putricinyl, pyridyl, piperidinyl, pyrrolidinyl, aminoacid, peptidyl, diaminoalkyl, and polyamine;

D is N, O, S, or a bond;

i and j are integers from about 2 to about 3;

k is an integer from 1 to about 3;

m, n, r and u are 1;

p is an integer from 1 to about 10;

$L_1$ and $L_2$, independently from one another, are an alkylene or an alkylene ether; and Y is selected from the group consisting of $CH_2$, O, S and NH.

39. The compound as claimed in claim 38 wherein $R_1$ and $R_4$, independently of one another, are straight-chain, branched, or cyclic alkyl, alkenyl, alkynyl or aryl groups having from about 8 to about 24 carbon atoms.

40. A compound having the formula:
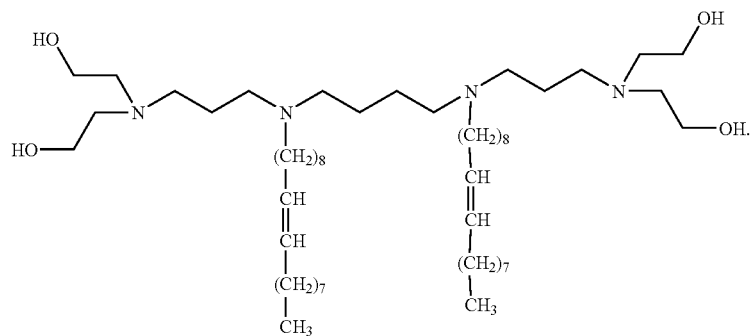
41. A compound having the formula:
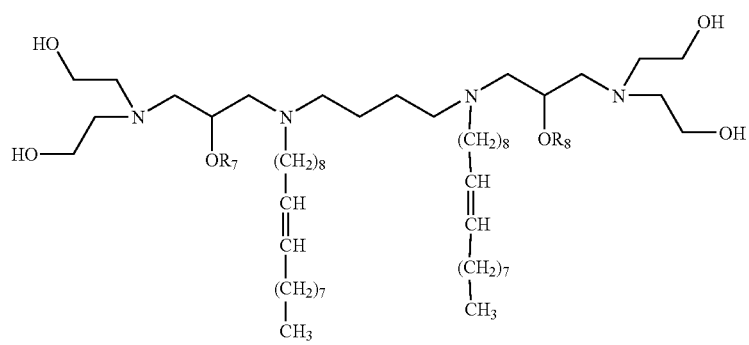
wherein $R_7$ and $R_8$ are independently H or a carbohydrate.
42. The compound as claimed in claim 41, wherein $R_7$ and $R_8$ are H.
43. A compound having the formula:
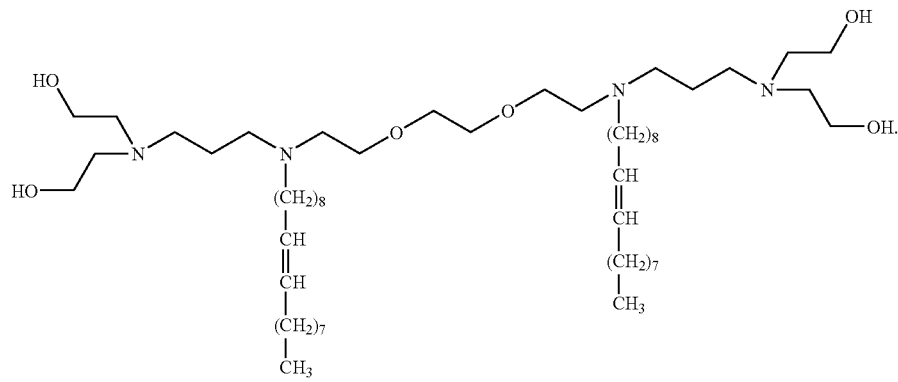

44. A compound having the formula:

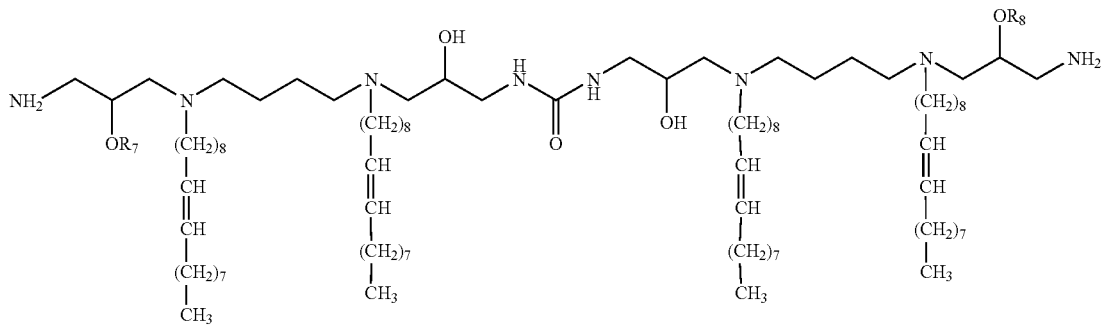

wherein $R_7$ and $R_8$ are independently H or a carbohydrate.

45. The compound as claimed in claim 44, wherein $R_7$ and $R_8$ are H.

46. A compound having the formula:

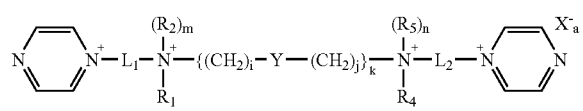

wherein $X^-$ is a physiologically acceptable anion;

a is the number of positive charges in the compound divided by the valence of the anion;

each of $R_1$ and $R_4$ is a straight-chain, branched, or cyclic alkenyl, alkynyl or aryl group having from about 8 to about 24 carbon atoms;

$R_2$ and $R_5$, independently of one another, are selected from the group consisting of an alkenyl group, an aryl group, and an alkyl group optionally substituted by one or more of an alcohol, an amine, an amide, an ether, a polyether, a polyamide, an ester, a mercaptan, a urea, a thiourea, a guanidyl, or a carbamoyl group;

m and n are 1;

i and j are integers from about 2 to about 3;

k is an integer from 1 to about 3;

$L_1$ and $L_2$, independently from one another, are an alkylene or an alkylene ether; and Y is selected from the group consisting of $CH_2$, O, S and NH.

47. The compound which is:

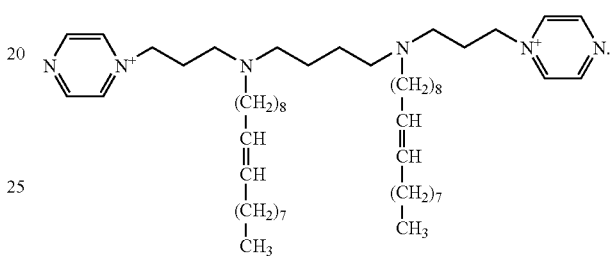

48. A compound having the formula:

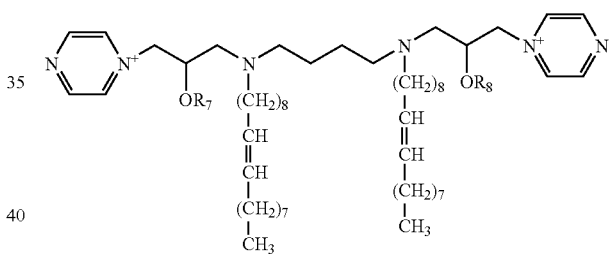

wherein $R_7$ and $R_8$ are independently H or a carbohydrate.

49. The compound as claimed in claim 48, wherein $R_7$ and $R_8$ are H.

50. A compound having the formula:

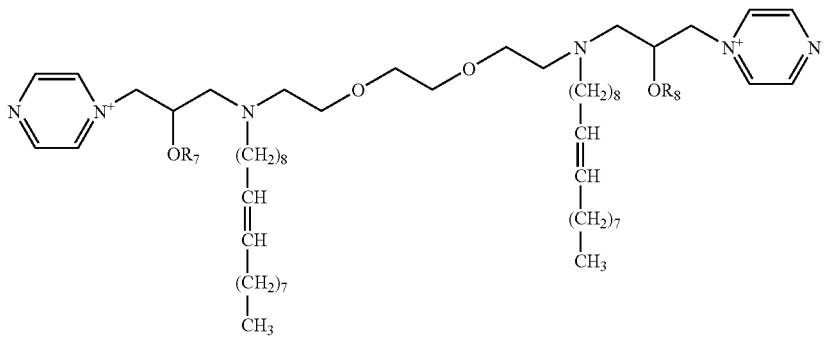

wherein $R_7$ and $R_8$ are independently H or a carbohydrate.

51. The compound as claimed in claim 50, wherein $R_7$ and $R_8$ are H.

52. A compound having the formula:

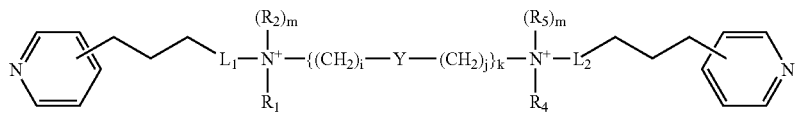

wherein
each of $R_1$ and $R_4$ is a straight-chain, branched, or cyclic alkenyl, alkynyl or aryl group having from about 8 to about 24 carbon atoms;
$R_2$ and $R_5$, independently of one another, are selected from the group consisting of an alkenyl group, an aryl group, and an alkyl group optionally substituted by one or more of an alcohol, an amine, an amide, an ether, a polyether, a polyamide, an ester, a mercaptan, a urea, a thiourea, a guanidyl, or a carbamoyl group;
m and n are 1;
i and j are integers from about 2 to about 3;
k is an integer from 1 to about 3;
$L_1$ and $L_2$ independently from one another, are an alkylene or an alkylene ether; and
Y is selected from the group consisting of $CH_2$, O, S and NH.

53. The compound which is:

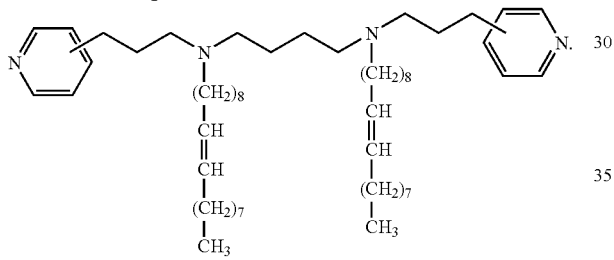

54. A compound having the formula:

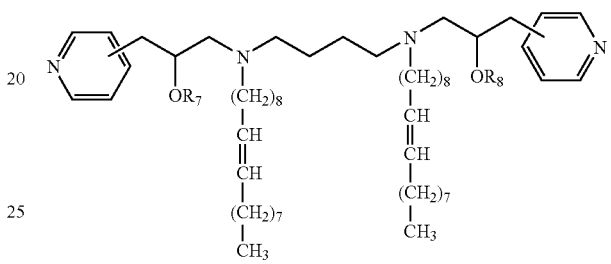

wherein $R_7$ and $R_8$ are independently H or a carbohydrate.

55. The compound according to claim 54, wherein $R_7$ and $R_8$ are H.

56. A compound having the formula:

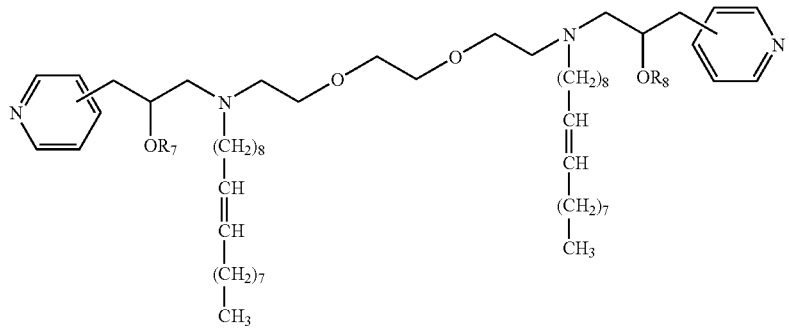

wherein $R_7$ and $R_8$ independently are H or a carbohydrate.

57. The compound as claimed in claim 56, wherein $R_7$ and $R_8$ are H.

58. A compound having the formula:

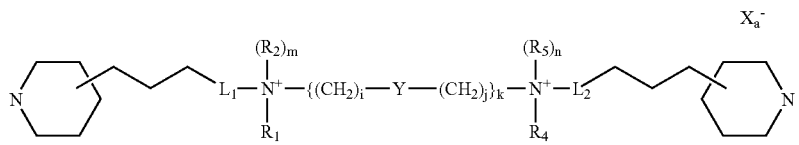

wherein
X⁻ is a physiologically acceptable anion;
a is the number of positive charges in the compound divided by the valence of the anion;
each of $R_1$ and $R_4$ is a straight-chain, branched, or cyclic alkenyl, alkynyl or aryl group having from about 8 to about 24 carbon atoms;
$R_2$ and $R_5$ independently of one another, are selected from the group consisting of an alkenyl group, an aryl group, and an alkyl group optionally substituted by one or more of an alcohol, an amine, an amide, an ether, a polyether, a polyamide, an ester, a mercaptan, a urea, a thiourea, a guanidyl, or a carbamoyl group;
m and n are 1;
i and j are integers from about 2 to about 3;
k is an integer from 1 to about 3;
$L_1$ and $L_2$, independently from one another, are an alkylene or an alkylene ether; and
Y is selected from the group consisting of $CH_2$, O, S and NH.

59. A compound having the formula:

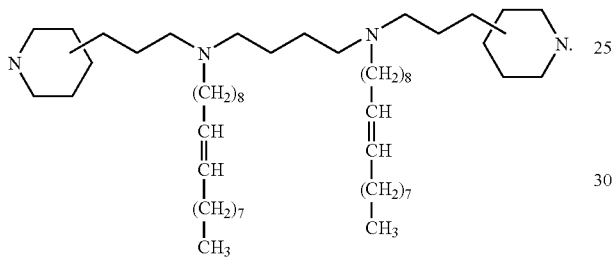

60. A compound having the formula:

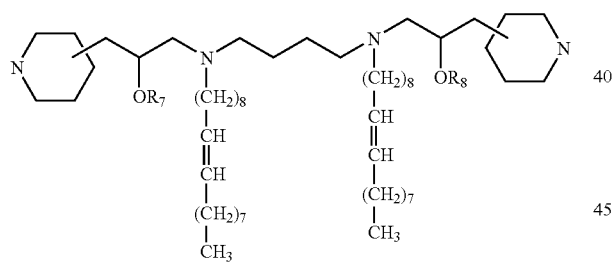

wherein $R_7$ and $R_8$ are independently H or a carbohydrate.

61. The compound as claimed in claim 60, wherein $R_7$ and $R_8$ are H.

62. A compound having the formula:

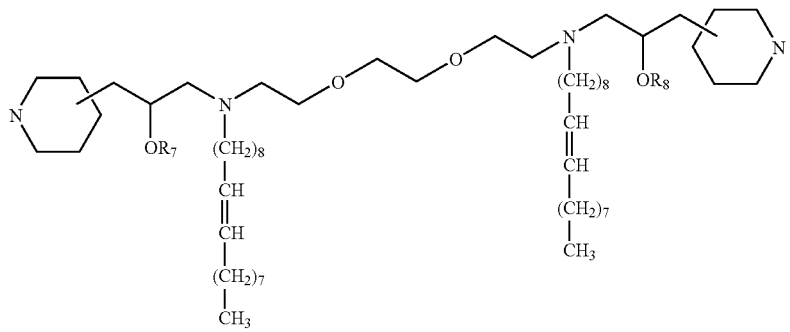

wherein $R_7$ and $R_8$ are independently H or a carbohydrate.

63. The compound as claimed in claim 62, wherein $R_7$ and $R_8$ are H.

64. A compound having the formula:

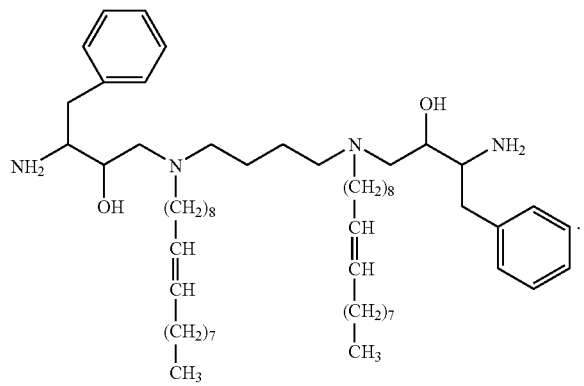

65. A compound having the formula:

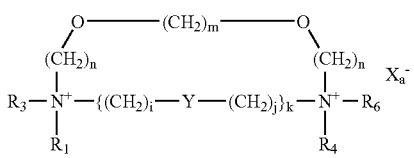

wherein
X⁻ is a physiologically acceptable anion;
a is the number of positive charges in the compound divided by the valence of the anion;
Y is selected from the group consisting of $CH_2$, an ether, a polyether, an amide, a polyamide, an ester, a sulfide, a urea, a thiourea, a guanidyl, a carbamoyl, a carbonate, a phosphate, a sulfate, a sulfoxide, an imine, a carbonyl, and a secondary amino group and wherein Y is optionally substituted by —$X_1$—L'—$X_2$—Z or —Z;
$R_1$, $R_3$, $R_4$, and $R_6$, independently of one another, are selected from the group consisting of H, —$(CH_2)_p$—D—Z, an alkyl group, an alkenyl group, an aryl group, an alkynyl group, and an alkyl ether group wherein any one of $R_1$, $R_3$, $R_4$, and $R_6$ are optionally substituted by one or more of an alcohol, an aminoalcohol, an amine, an amide, an ether, a polyether, a polyamide, an ester, a mercaptan, an alkylthio, a urea, a thiourea, a guanidyl, or a carbamoyl group, and at least one of $R_1$, $R_3$, $R_4$, and $R_6$ is a straight-chain, branched, or cyclic alkyl, alkenyl, alkynyl or aryl group having from 6 to about 64 carbon atoms; and $R_1$, $R_3$, $R_4$, and $R_6$ may optionally be covalently linked with each other or with Y, to form a cyclic moiety;

Z is selected from the group consisting of amine, spermiyl, carboxyspermiyl, guanidyl, spermidinyl, putricinyl, diaminoalkyl, pyridyl, piperidinyl, pyrrolidinyl, polyamine, amino acid, peptide, and protein;

$X_1$ and $X_2$, independently of one another, are selected from the group consisting of NH, O, S, alkylene, and arylene;

L' is selected from the group consisting of alkylene, alkenylene, alkynylene, arylene, alkylene ether, and polyether;

D is O, S, or a bond;

m and n are 1; and i, j, k, l and p are integers from 1 to about 10.

66. The compound as claimed in claim 65, wherein at least one of $R_1$ and $R_4$ is a straight-chain, branched, or cyclic alkyl, alkenyl, alkynyl or aryl group having from about 8 to about 24 carbon atoms.

67. The compound as claimed in claim 65, wherein the alkyl ether optionally substituted by one or more alcohol groups is a carbohydrate.

68. The compound as claimed in claim 67, wherein the carbohydrate is selected from the group consisting of galactose, fructose, glucose, maltose, sucrose, cellobiose, lactose, mannose, glucopyranose, mannopyranose and galactopyranose.

69. The compound as claimed in claim 65, wherein Y is selected from the group consisting of $CH_2$, an ether, a polyether, an amide, a polyamide, an ester, a sulfide, a urea, a thiourea, a guanidyl, a carbamoyl, a carbonate, and a secondary amino group.

70. The compound as claimed in claim 69, wherein at least one of $R_1$ and $R_4$ is a straight-chain, branched, or cyclic alkyl, alkenyl, alkynyl or aryl group having from about 8 to about 24 carbon atoms.

71. The compound as claimed in claim 69, wherein the alkyl ether optionally substituted by one or more alcohol groups is a carbohydrate.

72. The compound as claimed in claim 71, wherein the carbohydrate is selected from the group consisting of galactose, fructose, glucose, maltose, sucrose, cellobiose, lactose, mannose, glucopyranose, mannopyranose and galactopyranose.

73. A compound having the formula:

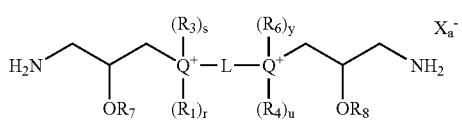

where:

Q is N;

L is a bivalent organic radical covalently linking each Q;

r, s, u and y are 1;

$X^-$ is a physiologically acceptable anion;

a is the number of anions which is equal to the number of positive charges in the compound divided by the valence of the anion;

$R_1$, $R_3$, $R_4$, and $R_6$, independently of one another, are selected from the group consisting of H, an alkyl group, an alkenyl group, an alkynyl group, and an aryl group, wherein any one of $R_1$, $R_3$, $R_4$, and $R_6$ are optionally substituted by one or more of an alcohol, an amine, an amide, an ether, a polyether, a polyamide, an ester, a mercaptan, a urea, a thiourea, a guanidyl, or a carbamoyl group, and at least two of $R_1$, $R_3$, $R_4$, and $R_6$, are straight-chain, branched, or cyclic alkyl, alkynyl, or alkenyl groups having from 8 to 24 carbon atoms attached to each N and $R_1$, $R_3$, $R_4$ and $R_6$ are optionally covalently linked with each other; and $R_7$ and $R_8$ are independently H or a carbohydrate.

74. A composition comprising one or more compounds of any one of claims 2, 5, 9, 17, 20, 21, 23, 25, 27, 30, 32, 38, 46, 52, 58, 65, or 73.

75. A composition comprising one or more compounds of any one of claims 2, 5, 9, 17, 20, 21, 23, 25, 27, 30, 32, 38, 46, 52, 58, 65, or 73 and at least one additional component selected from the group consisting of a cell, cells, a cell culture, a cell culture media, a neutral lipid, a nucleic acid, and a transfection enhancer.

76. A lipid aggregate comprising one or more compounds of any one of claims 2, 5, 9, 17, 20, 21, 23, 25, 27, 30, 32, 38, 46, 52, 58, 65, or 73.

77. A kit comprising one or more compounds of any one of claims 2, 5, 9, 17, 20, 21, 23, 25, 27, 30, 32, 38, 46, 52, 58, 65, or 73 and at least one additional component selected from the group consisting of a cell, cells, a cell culture medium, a nucleic acid, a transfection, enhancer and instructions for transfecting a cell or cells.

78. A method for introducing a polyanion into a cell or cells, said method comprising forming a lipid aggregate from a positively charged compound of any one of claims 2, 5, 9, 17, 20, 21, 23, 25, 27, 30, 32, 38, 46, 52, 58, 65, or 73, contacting the lipid aggregate with a polyanion to form a positively-charged polyanion-lipid aggregate complex and incubating the complex with a cell or cells.

79. A method for introducing a biologically active substance into a cell, said method comprising forming a lipid aggregate of a compound of any one of claims 1, 2, 5, 9, 17, 20, 21, 23, 25, 27, 30, 32, 38, 46, 52, 58, 65, or 73 and a biologically active substance and incubating the lipid aggregate with a cell or cell culture.

80. A compound which is:

$N^1,N^4$-dipalmitolyl-$N^1,N^4$-di-[2-hydroxy-3-(N-aminopropyl)]-diaminobutane;

$N^1,N^4$-distearyl-$N^1,N^4$-di-[2-hydroxy-3-(N-aminopropyl)]-diaminobutane;

$N^1,N^4$-dilauryl-$N^1,N^4$-di-[2-hydroxy-3-(N-aminopropyl)]-diaminobutane;

$N^1,N^2$-dimyristyl-$N^1,N^2$-di-[2-hydroxy-3-(N-aminopropyl)]-diaminoethane;

$N^1,N^2$-dipalmity-$N^1,N^2$-di-[2-hydroxy-3-(N-aminopropyl)]-diaminoethane;

$N^1,N^2$-dipalmitolyl-$N^1,N^2$-di-[2-hydroxy-3-(N-aminopropyl)]-diaminoethane;

$N^1,N^2$-distearyl-$N^1,N^2$-di-[2-hydroxy-3-(N-aminopropyl)]-diaminoethane;

$N^1,N^2$-dilauryl-$N^1$, $N^2$-di-[2-hydroxy-3-(N-aminopropyl)]-diaminoethane;

$N^1,N^8$-dimyristyl-$N^1,N^8$-di-[2-hydroxy-3-(N-aminopropyl)]-Jeffamine;

$N^1,N^8$-dipalmityl-$N^1,N^8$-di-[2-hydroxy-3-(N-aminopropyl)]-Jeffamine;

$N^1,N^8$-dipalmitolyl-$N^1,N^8$-di-[2-hydroxy-3-(N-aminopropyl)]-Jeffamine;

$N^1,N^8$-distearyl-$N^1,N^8$-di-[2-hydroxy-3-(N-aminopropyl)]-Jeffamine;

$N^1,N^8$-dilauryl-$N^1,N^8$-di-[2-hydroxy-3-(N-aminopropyl)]-Jeffamine;

$N^1,N^8$-dioleyl-$N^1,N^8$-di-[2-hydroxy-3-(N-aminopropyl)]-Jeffamine;

$N^1,N^4$-dimyristyl-$N^1,N^4$-di-[2-hydroxy-3-(N-sperminecarboxamido)aminopropyl]-diaminobutane;

$N^1,N^4$-dipalmityl-$N^1,N^4$-di-[2-hydroxy-3-(N-sperminecarboxamido)aminopropyl]-diaminobutane;

$N^1,N^4$-dipalmitolyl-$N^1,N^4$-di-[2-hydroxy-3-(N-sperminecarboxamido)aminopropyl]-diaminobutane;

$N^1,N^4$-distearyl-$N^1,N^4$-di-[2-hydroxy-3-(N-sperminecarboxamido)aminopropyl]-diaminobutane;

$N^1,N^4$-dilauryl-$N^1,N^4$-di-[2-hydroxy-3-(N-sperminecarboxamido)aminopropyl]-diaminobutane;

$N^1,N^8$-dimyristyl-$N^1,N^8$-di-[2-hydroxy-3-(N-sperminecarboxamido)aminopropyl]-Jeffamine;

$N^1,N^8$-dipalmityl-$N^1,N^8$-di-[2-hydroxy-3-(N-sperminecarboxamido)aminopropyl]-Jeffamine;

$N^1,N^8$-dipalmitolyl-$N^1,N^8$-di-[2-hydroxy-3-(N-sperminecarboxamido)aminopropyl]-Jeffamine;

$N^1,N^8$-distearyl-$N^1,N^8$-di-[2-hydroxy-3-(N-sperminecarboxamido)aminopropyl]-Jeffamine;

$N^1,N^8$-dilauryl-$N^1,N^8$-di-[2-hydroxy-3-(N-sperminecarboxamido)aminopropyl]-Jeffamine;

$N^1,N^8$-dioleyl-$N^1,N^8$-di-[2-hydroxy-3-(N-sperminecarboxamido)aminopropyl]-Jeffamine;

$N^1,N^2$-dimyristyl-$N^1,N^2$-di-[2-hydroxy-3-(N-sperminecarboxamido)aminopropyl]-diaminoethane;

$N^1,N^2$-dipalmityl-$N^1,N^2$-di-[2-hydroxy-3-(N-sperminecarboxamido)aminopropyl]-diaminoethane;

$N^1,N^2$-dipalmitolyl-$N^1,N^2$-di-[2-hydroxy-3-(N-sperminecarboxamido)aminopropyl]-diaminoethane;

$N^1,N^2$-distearyl-$N^1,N^2$-di-[2-hydroxy-3-(N-sperminecarboxamido)aminopropyl]-diaminoethane; or $N^1,N^2$-dilauryl-$N^1,N^2$-di-[2-hydroxy-3-(N-sperminecarboxamido)aminopropyl]-diaminoethane.

81. A compound which is:

83. A composition comprising one or more compounds of any one of claims 2, 5, 9, 17, 20, 21, 23, 25, 27, 30, 32, 38, 46, 52, 58, 65, or 73 and at least one additional lipid aggregating compound selected from DOPE, DOPC or cholesterol.

84. A composition comprising one or more compounds of any one of claims 2, 5, 9, 17, 20, 21, 23, 25, 27, 30, 32, 38, 46, 52, 58, 65, or 73 and at least one neutral lipid or at least one other cationic lipid.

85. A composition comprising one or more compounds of any one of claims 2, 5, 9, 17, 20, 21, 23, 25, 27, 30, 32, 38, 46, 52, 58, 65, or 73 and at least one cationic lipid selected from the group consisting of DOSPA, DOTMA, DMRIE, DOTAP, DOGS and TM-TPS.

86. A kit comprising one or more compounds of any one of claims 2, 5, 9, 17, 20, 21, 25, 27, 30, 32, 38, 46, 52, 58, 65, or 73.

87. A kit comprising one or more compounds of any one of claims 2, 5, 9, 17, 20, 21, 23, 25, 27, 30, 32, 38, 46, 52, 58, 65, or 73 and at least one additional lipid aggregating forming compound.

88. A kit comprising one or more compounds of any one of claims 2, 5, 9, 17, 20, 21, 23, 25, 27, 30, 32, 38, 46, 52, 58, 65, or 73 and at least one additional lipid aggregating forming compound selected from DOPE, DOPC or cholesterol.

89. A kit comprising one or more compounds of any one of claims 2, 5, 9, 17, 20, 21, 23, 25, 27, 30, 32, 38, 46, 52, 58, 65, or 73 and at least one neutral lipid or at least one other cationic lipid.

90. A kit comprising one or more compounds of any one of claims 2, 5, 9, 17, 20, 21, 23, 25, 27, 30, 32, 38, 46, 52, 58, 65, or 73 and at least one other cationic lipid selected from the group consisting of DOSPA, DOTMA, DMRIE, DOTAP, DOGS and TM-TPS.

91. A lipid aggregate comprising one or more compounds of any one of claims 2, 5, 9, 17, 20, 21, 23, 25, 27, 30, 32,

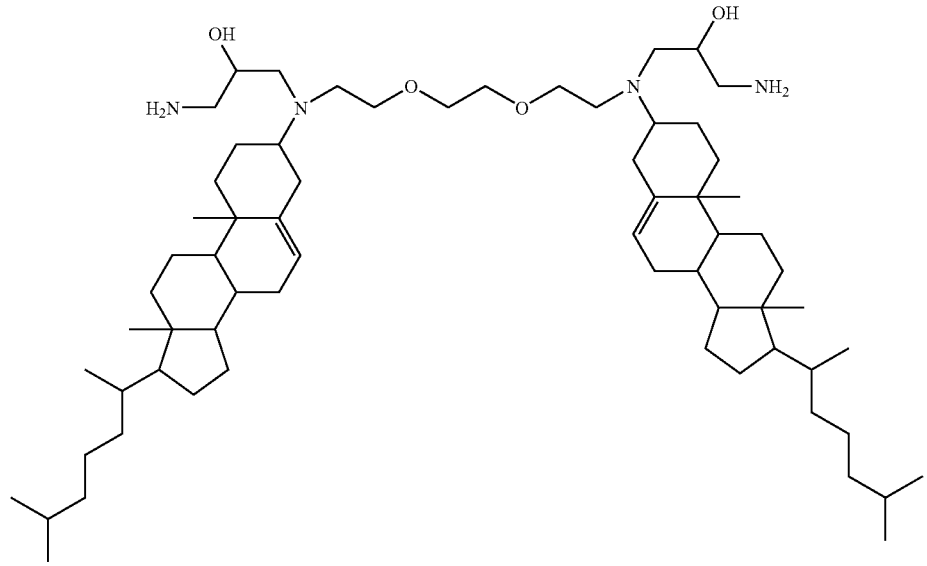

82. A composition comprising one or more compounds of any one of claims 2, 5, 9, 17, 20, 21, 23, 25, 27, 30, 32, 38, 46, 52, 58, 65, or 73 and at least one additional lipid aggregating compound.

38, 46, 52, 58, 65, or 73 and at least one additional lipid aggregating forming compound.

92. A lipid aggregate comprising one or more compounds of any one of claims 2, 5, 9, 17, 20, 21, 23, 25, 27, 30, 32,

38, 46, 52, 58, 65, or 73 and at least one additional lipid aggregating forming compound selected from DOPE, DOPC or cholesterol.

93. A lipid aggregate comprising one or more compounds of any one of claims 2, 5, 9, 17, 20, 21, 23, 25, 27, 30, 32, 38, 46, 52, 58, 65, 73 and at least one neutral lipid or at least one other cationic lipid.

94. A lipid aggregate comprising one or more compounds of any one of claims 2, 5, 9, 17, 20, 21, 23, 25, 27, 30, 32, 38, 46, 52, 58, 65 or 73 and at least one other cationic lipid selected from the group consisting of DOSPA, DOTMA, DMRIE, DOTAP, DOGS and TM-TPS.

95. A kit comprising a lipid aggregate comprising one or more compounds of any one of claims 2, 5, 9, 17, 20, 21, 23, 25, 27, 30, 32, 38, 46, 52, 58, 65, and 73 and at least one neutral lipid or at least one other cationic lipid.

96. The compound of claim 2 wherein $R_1$, $R_3$, $R_4$, and $R_6$, independently of one another, are selected from the group consisting of H, and an alkyl group and at least two of $R_1$, $R_3$, $R_4$, and $R_6$, are straight-chain alkyl groups having from 8 to 24 carbon atoms attached to each N.

97. The compound of claim 96 wherein at least two of $R_1$, $R_3$, $R_4$, and $R_6$, are straight-chain alkyl groups having 14 or 16 carbon atoms attached to each N.

98. The compound of claim 73 wherein $R_1$, $R_3$, $R_4$, and $R_6$, independently of one another, are selected from the group consisting of alkyl group, an alkenyl group, or an alkynyl group.

99. The compound of claim 73 wherein $R_1$, $R_3$, $R_4$, and $R_6$, independently of one another, are selected from the group consisting of H, and an alkyl group.

100. The compound of claim 73 wherein $R_7$ and $R_8$ are H.

101. The compound of claim 73 wherein two of $R_1$, $R_3$, $R_4$, and $R_6$ are alkyl groups having 14 or 16 carbons.

* * * * *

UNITED STATES PATENT AND TRADEMARK OFFICE
CERTIFICATE OF CORRECTION

PATENT NO. : 7,166,745 B1
APPLICATION NO. : 09/438365
DATED : January 23, 2007
INVENTOR(S) : Chu et al.

It is certified that error appears in the above-identified patent and that said Letters Patent is hereby corrected as shown below:

In Columns 69 and 70, lines 25-43, in Claim 13, delete
"

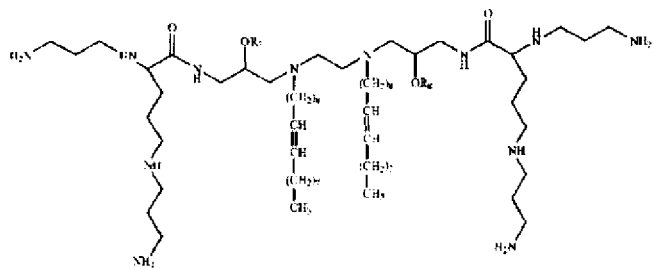

"

and insert therefor
--

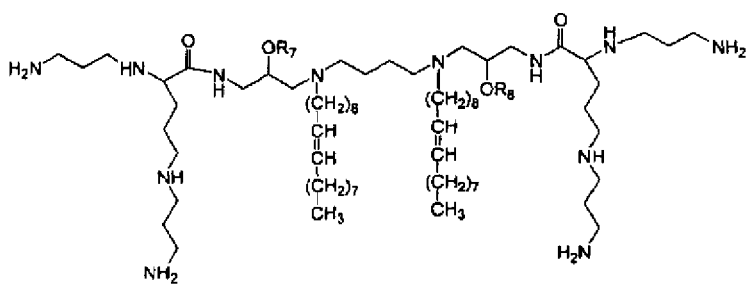

--.

In Column 71, lines 30-43, in Claim 19, delete
"

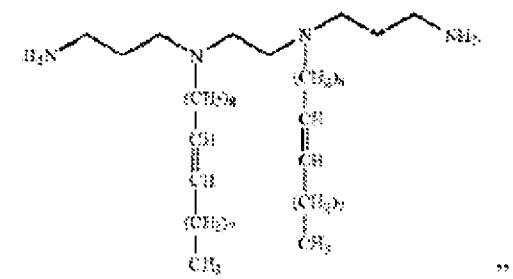

"

UNITED STATES PATENT AND TRADEMARK OFFICE
CERTIFICATE OF CORRECTION

PATENT NO. : 7,166,745 B1
APPLICATION NO. : 09/438365
DATED : January 23, 2007
INVENTOR(S) : Chu et al.

Page 2 of 3

It is certified that error appears in the above-identified patent and that said Letters Patent is hereby corrected as shown below:

and insert therefor
--

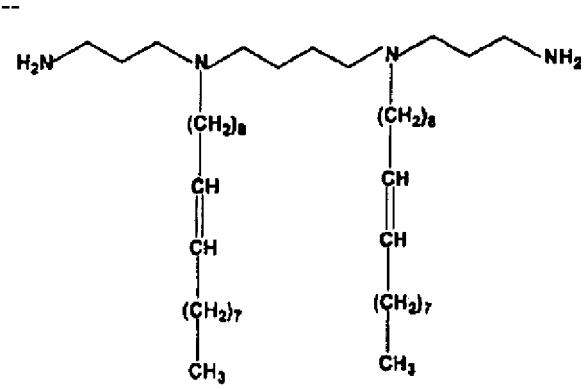

--.

In Column 76, lines 45-60, in Claim 34, delete
"

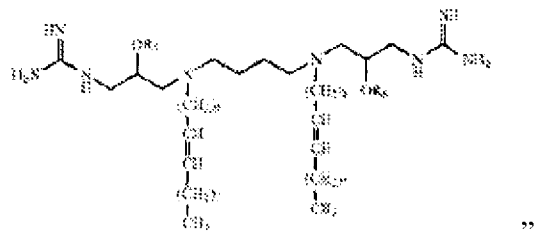

"

and insert therefor
--

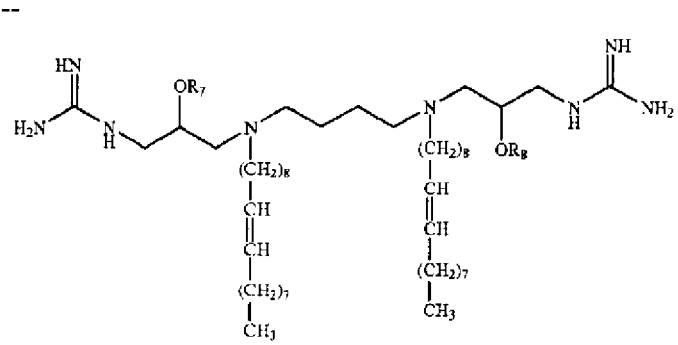

--.

UNITED STATES PATENT AND TRADEMARK OFFICE
CERTIFICATE OF CORRECTION

PATENT NO. : 7,166,745 B1
APPLICATION NO. : 09/438365
DATED : January 23, 2007
INVENTOR(S) : Chu et al.

It is certified that error appears in the above-identified patent and that said Letters Patent is hereby corrected as shown below:

In Column 92, line 9, in Claim 98, delete "consisting of alkyl group" and insert therefor -- consisting of H, an alkyl group --.

Signed and Sealed this

First Day of September, 2009

David J. Kappos
*Director of the United States Patent and Trademark Office*